United States Patent [19]
Henrie II et al.

[11] Patent Number: 5,874,579
[45] Date of Patent: *Feb. 23, 1999

[54] INSECTICIDAL SUBSTITUTED-2.4-DIAMINOQUINAZOLINES RELATED APPLICATIONS

[75] Inventors: Robert N. Henrie II, East Windsor; Clinton J. Peake, Trenton; Thomas G. Cullen, Milltown, all of N.J.; Walter H. Yeager, Yardley, Pa.

[73] Assignee: FMC Corporation, Philadelphia, Pa.

[*] Notice: The term of this patent shall not extend beyond the expiration date of Pat. No. 5,534,518.

[21] Appl. No.: 640,610

[22] Filed: May 1, 1996

Related U.S. Application Data

[63] Continuation of Ser. No. 267,340, Jun. 28, 1994, Pat. No. 5,534,518, which is a continuation-in-part of Ser. No. 149,491, Nov. 9, 1993, abandoned, which is a continuation-in-part of Ser. No. 19,389, Feb. 18, 1993, abandoned.

[51] Int. Cl.$^6$ .................. C07D 239/95; A61K 31/505
[52] U.S. Cl. .................. 544/291; 514/260; 544/284
[58] Field of Search .................. 544/291

[56] References Cited

U.S. PATENT DOCUMENTS

| | | | |
|---|---|---|---|
| 2,945,859 | 7/1960 | Hitchings et al. | 544/291 |
| 3,485,842 | 12/1969 | Davoll | 260/256 |
| 3,511,836 | 5/1970 | Hess | 544/292 |
| 3,546,224 | 12/1970 | Davoll | 260/256 |
| 3,560,502 | 2/1971 | Davoll | 280/256 |
| 3,635,979 | 1/1972 | Hess | 544/292 |
| 4,287,341 | 9/1981 | Hess et al. | 544/285 |
| 4,298,613 | 11/1981 | Lepone | 424/274 |
| 4,377,581 | 3/1983 | Hess et al. | 514/259 |
| 4,435,401 | 3/1984 | Campbell et al. | 544/292 |
| 4,451,466 | 5/1984 | Horne et al. | 424/251 |
| 4,672,116 | 6/1987 | Bandurco et al. | 544/286 |
| 4,677,219 | 6/1987 | Berman et al. | 558/419 |
| 4,818,753 | 4/1989 | Colwell | 514/155 |
| 5,064,833 | 11/1991 | Ife et al. | 514/260 |
| 5,411,963 | 5/1995 | Dreikorn et al. | 514/259 |

FOREIGN PATENT DOCUMENTS

| | | |
|---|---|---|
| 028473 | 5/1981 | European Pat. Off. . |
| 326329 | 5/1989 | European Pat. Off. . |
| 370704 | 6/1990 | European Pat. Off. . |
| 3103484 | 4/1977 | Japan . |
| 1078887 | 2/1966 | United Kingdom . |

OTHER PUBLICATIONS

"Comparative QSAR of Antibacterial Dihydrofolate Inhibitors", Coats et al. CA 103 (21): 17145c, (1984).

"Antifolate and Antibacterial Activities of G–Substituted 2,4–Diamino–qinazolines", Harris et al, Eur. J. Med Chem., 27; 07–18 (1992).

"Structure—Activity Relationships of Dihydrofolate Reductase Inhibitors", Blaney et al, Chemical Reviews, 84 (4), 333–407 (1984).

"Antifolate and Antibacterial Ac/tivities of 5–Substituted 2,4–Diaminoquinazolines", Harris et al, J. Med–Chem., 33, 434–444 (1990).

Primary Examiner—Matthew V. Grumbling
Attorney, Agent, or Firm—Stanford M. Back; Donald J. Silvert

[57] ABSTRACT

An insecticidal composition comprising, in admixture with an agriculturally acceptable carrier, an insecticidally effective amount of a 2,4-diaminoquinazoline compound of the formula:

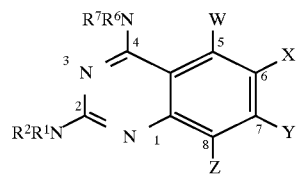

wherein $R^1$, $R^2$, $R^6$, $R^7$, W, X, Y, and Z are as defined herein; methods of using the same; novel 2,4-diaminoquinazolines per se; and intermediates in the preparation thereof.

2 Claims, No Drawings

INSECTICIDAL SUBSTITUTED-2.4-DIAMINOQUINAZOLINES RELATED APPLICATIONS

RELATED APPLICATIONS

This application is a continuation of U.S. application Ser. No. 08/267,340, filed Jun. 28, 1994, now U.S. Pat. No. 5,534,518 which in turn is a continuation-in-part of U.S. application Ser. No. 08/149,491, filed Nov. 9, 1993 in the names of Henrie et al, which in turn is a continuation-in-part of U.S. application Ser. No. 08/019,389, filed Feb. 18, 1993 in the names of Henrie et al. (now abandoned).

BACKGROUND OF THE INVENTION

This invention relates to quinazoline compounds and compositions containing the same which are useful for controlling insects in agricultural crops. Still more particularly, this invention relates to certain 2,4-diaminoquinazoline compounds and compositions, and their use as insecticides against a variety of insects, including larvae, such as the tobacco budworm. Numerous of these diaminoquinazoline compounds employed herein, and their preparation, have been described in the literature for use in a variety of fields, but not as insecticides.

SUMMARY OF THE INVENTION

In accordance with the present invention it has been found that substituted-2,4-diaminoquinazolines, and agriculturally acceptable salts thereof, when present in insecticidally effective amounts, and with a suitable agricultural carrier, are useful as active ingredients in the insecticidal compositions and methods of this invention. These quinazolines may be represented by the following structure:

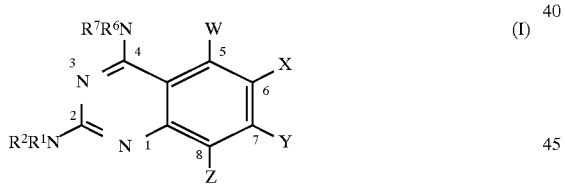

wherein $R^1$ and $R^6$ are independently hydrogen or lower alkyl;

$R^2$ and $R^7$ are hydrogen, lower alkyl, alkylcarbonyl [e.g., —C(=O)CH$_3$, —C(=O)C(CH$_3$)$_3$, or —C(=O)C$_{11}$H$_{23}$], lower alkoxycarbonyl [e.g., —C(=O)OC(CH$_3$)$_3$], lower haloalkylcarbonyl [e.g., —C(=O)C$_3$F$_7$], alkoxyalkylcarbonyl [e.g., —C(=O)CH$_2$OC$_2$H$_5$ or —C(=O)C$_2$H$_4$OC$_2$H$_5$], alkoxyalkoxyalkylcarbonyl (e.g., —C(=O)CH$_2$OC$_2$H$_4$OC$_2$H$_5$), alkoxyalkoxyalkoxyalkylcarbonyl [e.g., —C(=O)CH$_2$OC$_2$H$_4$OC$_2$H$_4$OCH$_3$], arylcarbonyl (e.g., phenylcarbonyl), substituted arylcarbonyl (e.g., 4-chlorophenylcarbonyl), or alkynylcarbonyl [e.g., —C(=O)C≡CCH$_3$];

or $R^1$ and $R^2$, taken together, form the group —R$^5$—O—R$^5$, wherein $R^5$ is lower alkylene;

or $R^1$ and $R^2$, taken together, and $R^6$ and $R^7$ taken together each form the group

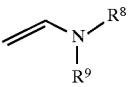

wherein $R^8$ and $R^9$ are independently straight or branched chain lower alkyl [e.g., —CH$_3$, —CH(CH$_3$)$_2$]; or $R^8$ and $R^9$ taken together with two to five methylene groups form an alkylene ring [e.g., —(CH$_2$)$_5$—];

W, Y, and Z are independently hydrogen, halogen, lower alkyl, lower alkoxy, lower haloalkyl, lower haloalkoxy, thienyl or substituted thienyl, (e.g., with substituents such as lower alkyl, halogen, or haloalkyl), aroyl or substituted aroyl, (e.g., with substituents such as hydrogen, halogen, haloalkyl, cyano, carboxy, lower alkoxycarbonyl, or phenyl substituted with halogen or lower haloalkyl), cyano, nitro, amino, lower dialkylamino, aryl (e.g., phenyl) or substituted aryl, (e.g., with substituents such as lower alkyl or lower haloalkyl), arylalkyl, arylalkenyl, arylalkynyl, arylthio, arylsulfinyl, arylsulfonyl, arylaminoalkyl, arylalkylamino, arylalkylimino, (aryl)(halo)alkenyl, substituted (aryl)(halo)alkenyl, (e.g., with substituents such as hydrogen, halogen, lower alkyl, lower haloalkyl, cyano, carboxy, lower alkylcarbonyl, or aminocarbonyl), (aryl)(alkyl)aminoalkyl, arylalkycarbonylamino, arylalkylthio, or arylthioalkyl; and X is (a) hydrogen, halogen, lower alkyl, lower alkoxy, lower haloalkyl, lower haloalkoxy, thienyl or substituted thienyl, (e.g., with substituents such as lower alkyl, halogen, or haloalkyl), aroyl or substituted aroyl, (e.g., with substituents such as hydrogen, halogen, haloalkyl, cyano, carboxy, lower alkoxycarbonyl, or phenyl substituted with halogen or lower haloalkyl), cyano, nitro, amino, lower dialkylamino, aryl (e.g., phenyl or naphthyl), arylalkyl, arylalkenyl, arylalkynyl, aryloxy, arylthio, arylsulfinyl, arylsulfonyl, arylaminoalkyl, arylalkylamino, arylalkylimino, (aryl)(halo)alkenyl, or substituted (aryl)(halo)alkenyl, (e.g., with substituents such as hydrogen, halogen, lower alkyl, lower haloalkyl, cyano, carboxy, lower alkylcarbonyl, or aminocarbonyl), (aryl)(alkyl)aminoalkyl, or arylalkycarbonylamino; or (b) substituted aryl, [e.g., phenyl] i.e., aryl substituted with one or more of halogens (e.g., Cl, F), lower alkyl (e.g., —CH$_3$), lower haloalkyl (e.g., —CF$_3$), lower alkoxy (e.g., —OCH$_3$), lower alkylthio (e.g., —SC$_4$H$_9$), lower alkylsulfonyl (e.g., —SO$_2$C$_2$H$_5$, or —SO$_2$C$_4$H$_9$), formyl, lower alkoxycarbonyl [e.g., —C(=O)OCH$_3$], phenyl or phenyl substituted with one or more halogens (e.g., Cl, F) or lower haloalkyl (e.g., —CF$_3$), phenoxy, or phenoxy substituted with one or more halogens (e.g., Cl, F), lower haloalkoxy, lower alkoxyalkyl, carboxy, cyano, nitro, aminocarbonyl, lower alkylcarbonylamino, lower alkylsulfonylamino; or substituted phenyl of the formula

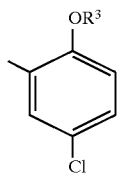

wherein R³ is hydrogen; alkyl, (e.g. methyl, 1-methylethyl, n-pentyl, or undecyl); tri(lower alkyl) silylalkyl; (4-halophenyl)lower alkyl; pentahalophenylalkyl; pyridin-2-ylalkyl; or 2-(4-alkylsulfonylphenoxy)ethyl; or (c) substituted aryloxy, [e.g., phenoxy] of the formula:

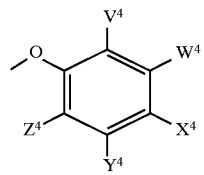

wherein $V^4$, $W^4$, $X^4$, $Y^4$, and $Z^4$ are selected from hydrogen, halogen, (e.g., Cl), or haloalkyl (e.g., —CF₃); or (d) a benzo-fused oxygen-containing heterocycle of the formula:

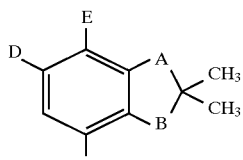

wherein A and B are independently selected from oxygen, methylene, and carbonyl, with the proviso that at least one of A or B is oxygen; D is hydrogen, halogen (e.g., Cl, F), lower alkyl (e.g., —CH₃), or lower haloalkyl (e.g., —CF₃); and E is hydrogen, hydroxy, or lower alkoxy (e.g., —OCH₃); to form, for example, the heterocycle 2,3-dihydro-2,2-dimethylbenzofuran-4-yl, 2,3-dihydro-2,2-dimethylbenzofuran-7-yl, 6-halo-2,3-dihydro-2,2-dimethylbenzofuran-4-yl, 5-halo-2,3-dihydro-2,2-dimethylbenzofuran-7-yl, or 2,3-dihydro-2,2-dimethyl-3-benzofuranon-4-yl; or (e) an arylalkylamino of the formula:

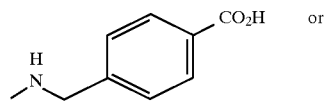

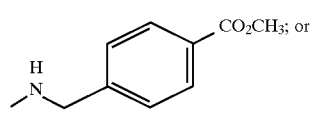

(f) an arylthioalkylcarbonylamino of the formula:

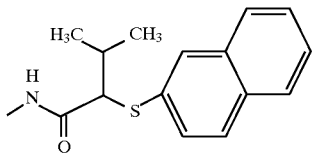

and agriculturally acceptable salts thereof.

Agriculturally acceptable salts of the diaminoquinazolines include, but are not limited to, for example, the salts of hydrochloric acid, ethanesulfonic acid, gluconic acid, and pamoic acid.

Of these compounds, among the more preferred ones for use in the compositions and methods of this invention are those wherein the diaminoquinazolines are of the structure (I) above, and wherein (a) $R^1$ is hydrogen, or lower alkyl;
$R^6$ is hydrogen;
$R^2$ and $R^7$ are independently hydrogen, lower alkyl, alkylcarbonyl [e.g., —C(=O)CH₃, —C(=O)C(CH₃)₃, or —C(=O)C₁₁H₂₃], lower alkoxycarbonyl [e.g., —C(=O)OC(CH₃)₃], lower haloalkylcarbonyl [e.g., —C(=O)C₃F₇], alkoxyalkylcarbonyl [e.g., —C(=O)CH₂OC₂H₅ or —C(=O)C₂H₄OC₂H₅], alkoxyalkoxyalkylcarbonyl (e.g., —C(=O)CH₂OC₂H₄OC₂H₅), or alkoxyalkoxyalkoxyalkylcarbonyl [e.g., —C(=O)CH₂OC₂H₄OC2H₄OCH₃];
Y and Z are hydrogen;
W is halogen, (e.g., chlorine), or lower alkyl, (e.g., methyl or isopropyl); and
X is phenyl, or substituted aryl, [e.g., phenyl] i.e., aryl substituted with one or more of halogens (e.g., Cl, F), lower alkyl (e.g., —CH₃), lower haloalkyl (e.g., —CF₃), lower alkoxy (e.g., —OCH₃), lower alkylthio (e.g., —SC₄H₉), lower alkylsulfonyl (e.g., —SO₂C₂H₅, or —SO₂C₄H₉), formyl, lower alkoxycarbonyl [e.g., —C(=O)OCH₃], phenyl or phenyl substituted with one or more halogens (e.g., Cl, F) or lower haloalkyl (e.g., —CF₃), phenoxy, or phenoxy substituted with one or more halogens (e.g., Cl, F), lower haloalkoxy, lower alkoxyalkyl, carboxy, cyano, nitro, aminocarbonyl, lower alkylcarbonylamino, lower alkylsulfonylamino; or substituted phenyl of the formula

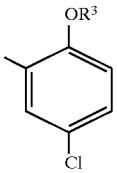

wherein R³ is hydrogen; alkyl, (e.g. methyl, 1-methylethyl, n-pentyl, or undecyl); tri(lower alkyl) silylalkyl; (4-halophenyl)lower alkyl; pentahalophenylalkyl; pyridin-2-ylalkyl; or 2-(4-alkylsulfonylphenoxy)ethyl;

(b) $R^1$ is hydrogen, or lower alkyl;
$R^6$ is hydrogen;
$R^2$ and $R^7$ are independently hydrogen, lower alkyl, alkylcarbonyl [e.g., —C(=O)CH₃, —C(=O)C(CH₃)₃, or —C(=O)C₁₁H₂₃], or lower alkoxycarbonyl [e.g., —C(=O)OC(CH₃)₃], lower haloalkylcarbonyl [e.g., —C(=O)C₃F₇], alkoxyalkylcarbonyl [e.g., —C(=O)CH₂OC₂H₅, or —C(=O)C₂H₄OC₂H₅], alkoxyalkoxyalkylcarbonyl (e.g., —C(=O)CH$_2$OC$_2$H$_4$OC$_2$H$_5$), or alkoxyalkoxy-alkoxyalkylcarbonyl [e.g., -C(=O)CH2OC2H4OC2H4OCH3];

Y and Z are hydrogen;

W is halogen, (e.g., chlorine), or lower alkyl, (e.g., methyl or isopropyl); and X is aroyl, (e.g., benzoyl or naphthoyl), or substituted aroyl of the formula:

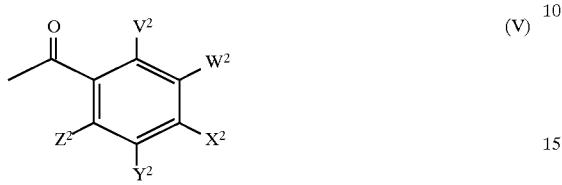

wherein $V^2$, $W^2$, $X^2$, $Y^2$, and $Z^2$ are independently selected from hydrogen, halogen, haloalkyl, cyano, carboxy, lower alkoxycarbonyl, and phenyl substituted with halogen or lower haloalkyl;

(c) $R^1$ is hydrogen, or lower alkyl;

$R^6$ is hydrogen;

$R^2$ and $R^7$ are independently hydrogen, lower alkyl, alkylcarbonyl [e.g., —C(=O)CH$_3$, —C(=O)C(CH$_3$)$_3$, or —C(=O)C$_{11}$H$_{23}$], or lower alkoxycarbonyl [e.g., —C(=O)OC(CH$_3$)$_3$], lower haloalkylcarbonyl [e.g., —C(=O)C$_3$F$_7$], alkoxyalkylcarbonyl [e.g., —C(=O)CH$_2$OC$_2$H$_5$, or —C(=O)C$_2$H$_4$OC$_2$H$_5$], alkoxyalkoxyalkylcarbonyl (e.g., —C(=O)CH$_2$OC$_2$H$_4$OC$_2$H$_5$), or alkoxyalkoxyalkoxyalkylcarbonyl [e.g., —C(=O)CH$_2$OC$_2$H$_4$OC$_2$H$_4$OCH$_3$];

Y and Z are hydrogen;

W is halogen (e.g., chlorine) or lower alkyl (e.g., methyl or isopropyl); and

X is (aryl)(halo)alkenyl of the formula:

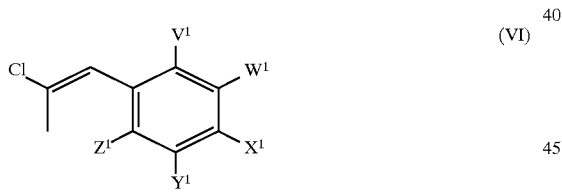

wherein $V^1$, $W^1$, $X^1$, $Y^1$, and $Z^1$ are independently selected from hydrogen, halogen, lower alkyl, lower haloalkyl, cyano, carboxy, lower alkoxycarbonyl, and aminocarbonyl; and (d) $R^1$ is hydrogen, or lower alkyl;

$R^6$ is hydrogen;

$R^2$ and $R^7$ are independently hydrogen, lower alkyl, alkylcarbonyl [e.g., —C(=O)CH$_3$, —C(=O)C(CH$_3$)$_3$, or —C(=O)C$_{11}$H$_{23}$], lower alkoxycarbonyl [e.g., —C(=O)OC(CH$_3$)$_3$], lower haloalkylcarbonyl [e.g., —C(=O)C$_3$F$_7$], alkoxyalkylcarbonyl [e.g., —C(=O)CH2OC$_2$H$_5$, or —C(=O)C$_2$H$_4$OC$_2$H$_5$], alkoxyalkoxyalkylcarbonyl (e.g., —C(=O)CH$_2$OC$_2$H$_4$OC$_2$H$_5$), or alkoxyalkoxyalkoxyalkylcarbonyl [e.g., —C(=O)CH$_2$OC$_2$H$_4$OC$_2$H$_4$OCH$_3$];

Y and Z are hydrogen;

W is halogen or lower alkyl (e.g., methyl); and

X is a benzo-fused oxygen-containing heterocycle of the formula:

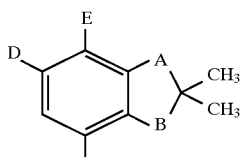

wherein A and B are independently selected from oxygen, methylene, and carbonyl; with the proviso that at least one of A or B is oxygen; D is hydrogen, halogen (e.g., Cl, F), lower alkyl (e.g., —CH$_3$), or lower haloalkyl (e.g., —CF$_3$); and E is hydrogen, hydroxy, or lower alkoxy (e.g., —OCH3); to form, for example, the heterocycle 2,3-dihydro-2,2-dimethylbenzofuran-4-yl, 2,3-dihydro-2,2-dimethylbenzofuran-7-yl, 6-halo-2,3-dihydro-2,2-dimethylbenzofuran-4-yl, 5-halo-2,3-dihydro-2,2-dimethylbenzofuran-7-yl, or 2,3-dihydro-2,2-dimethyl-3-benzofuranon-4-yl.

Other compounds of particular interest falling within the scope of this invention include compounds of Formula I wherein (i) $R^1$, $R^2$, $R^6$, and $R^7$ are hydrogen;

Y and Z are hydrogen;

W is hydrogen, halogen, (e.g., chlorine), or lower alkyl, (e.g., methyl);

X is arylaminoalkyl or arylalkylimino of the formula:

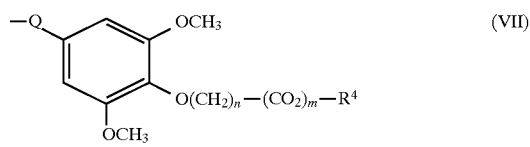

wherein Q is alkylimino of the formula —N=CH— (in which the left-hand portion of the moiety Q is attached to the quinazoline ring), or aminoalkyl of the formula —CH$_2$NH—;

n is 1, 2, or 3;

m is 0 or 1; and $R^4$ is hydrogen or lower alkyl;

with the proviso that when m is 0, $R^4$ must be hydrogen, and n must be 1; and (ii) $R^1$, $R^2$, $R^6$, and $R^7$ are hydrogen;

W, Y, and Z are hydrogen; and

X is an (aryl)(alkyl)aminoalkyl of the formula:

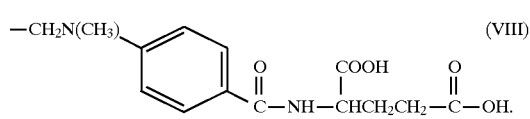

In a further embodiment, this invention is also directed to certain novel substituted quinazolines per se falling within the scope of formula (I) above. These compounds, as illustrated by Compounds 43–45, 47–74, 106–138, 142–173, and 176–182 of Table I below, include the following novel quinazolines, which may be prepared by methods that are provided in detail in Examples 1–3, 5, and 16–19:

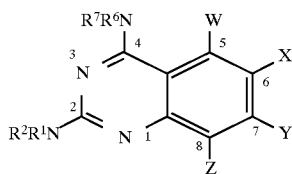 (IX)

wherein

R¹ is hydrogen, or lower alkyl;

R⁶ is hydrogen;

R² and R⁷ are independently hydrogen, lower alkyl, alkylcarbonyl [e.g., —C(=O)CH₃, —C(=O)C(CH₃)₃, or —C(=O)C₁₁H₂₃], lower alkoxycarbonyl [e.g., —C(=O)OC(CH₃)₃], lower haloalkylcarbonyl [e.g., —C(=O)C₃F₇], alkoxyalkylcarbonyl [e.g., —C(=O)CH₂OC₂H₅, or —C(=O)C₂H₄OC₂H₅], alkoxyalkoxyalkylcarbonyl (e.g., —C(=O)CH₂OC₂H₄OC₂H₅), or alkoxyalkoxyalkoxyalkylcarbonyl [e.g., —C(=O)CH₂OC₂H₄OC₂H₄OCH₃]; or R¹ and R², taken together, form the group —R⁵—O—R⁵, wherein R⁵ is lower alkylene;

W is selected from hydrogen, halogen, lower alkyl, lower haloalkyl, phenyl, and phenyl substituted with lower alkyl or lower haloalkyl, with the proviso that when X is phenyl, W is other than hydrogen;

Y and Z are selected from hydrogen, halogen, and phenyl; and

X is selected from
(a) phenyl;
(b) substituted aryl, [e.g., phenyl] i.e., aryl substituted with one or more of halogens (e.g., Cl, F), lower alkyl (e.g., —CH₃), lower haloalkyl (e.g., —CF₃), lower alkoxy (e.g., —OCH₃), lower alkylthio (e.g., —SC₄H₉), lower alkylsulfonyl (e.g., —SO₂C₂H₅, or —SO₂C₄H₉), formyl, lower alkoxycarbonyl [e.g., —C(=O)OCH₃], phenyl or phenyl substituted with one or more halogens (e.g., Cl, F) or lower haloalkyl (e.g., —CF₃), phenoxy, or phenoxy substituted with one or more halogens (e.g., Cl, F), lower haloalkoxy, lower alkoxyalkyl, carboxy, cyano, nitro, aminocarbonyl, lower alkylcarbonylamino, lower alkylsulfonylamino;
or substituted phenyl of the formula

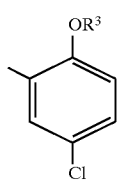 (X)

wherein R³ is hydrogen; alkyl, (e.g. methyl, 1-methylethyl, n-pentyl, or undecyl); tri(lower alkyl)silylalkyl; (4-halophenyl)lower alkyl; pentahalophenylalkyl; pyridin-2-ylalkyl; or 2-(4-alkylsulfonylphenoxy)ethyl;
(c) naphthyl;
(d) thienyl or thienyl substituted with halogen, lower alkyl, or haloalkyl;
(e) aroyl or substituted aroyl of the formula:

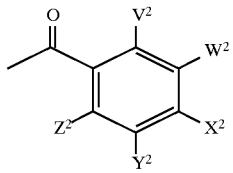 (XI)

wherein V², W², X², Y², and Z² are independently selected from hydrogen, halogen, haloalkyl, cyano, carboxy, lower alkoxycarbonyl, and phenyl substituted with halogen or haloalkyl;
(f) (aryl)(halo)alkenyl of the formula:

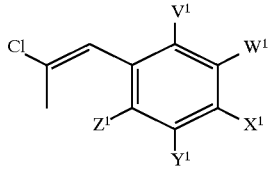 (XII)

wherein V¹, W¹, X¹, Y¹, and Z¹ are independently selected from hydrogen, halogen, lower alkyl, lower haloalkyl, cyano, carboxy, lower alkoxycarbonyl, and aminocarbonyl; and
(g) is a benzo-fused oxygen-containing heterocycle of the formula:

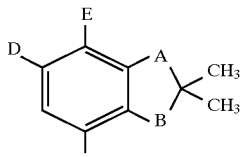

wherein A and B are independently selected from oxygen, methylene, and carbonyl; with the proviso that at least one of A or B is oxygen; D is hydrogen, halogen (e.g., Cl, F), lower alkyl (e.g., —CH₃), or lower haloalkyl (e.g., —CF₃); and E is hydrogen, hydroxy, or lower alkoxy (e.g., —OCH₃); to form, for example, the heterocycle 2,3-dihydro-2,2-dimethylbenzofuran-4-yl, 2,3-dihydro-2,2-dimethylbenzofuran-7-yl, 6-halo-2,3-dihydro-2,2-dimethylbenzofuran-4-yl, 5-halo-2,3-dihydro-2,2-diemthylbenzofuran-7-yl, or 2,3-dihydro-2,2-dimethyl-3-benzofuranon-4-yl.

Preferred amongst the above novel quinazolines are those of Formula IX wherein R¹, R², R⁶, R⁷, Y and Z are hydrogen; W is methyl; and X is
(i) phenyl substituted with one or more of fluoro, chloro, or trifluoromethyl;
(ii) compounds of the formula

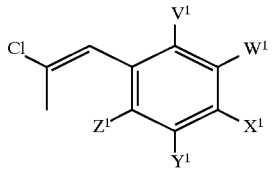 (XIII)

wherein V¹, W¹, X¹, Y¹, and Z¹ are independently selected from hydrogen, chloro, and trifluoromethyl; or
(iii) a benzo-fused oxygen containing heterocycle of the formula:

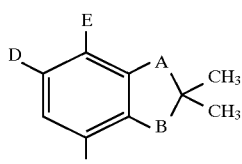

wherein A and B are independently selected from oxygen, methylene, and carbonyl; with the proviso that at least one of A or B is oxygen; D is hydrogen, halogen (e.g., Cl, F), lower alkyl (e.g., —CH$_3$), or lower haloalkyl (e.g., —CF$_3$); and E is hydrogen, hydroxy, or lower alkoxy (e.g., —OCH$_3$); to form, for example, the heterocycle 2,3-dihydro-2,2-dimethylbenzofuran-4-yl, 2,3-dihydro-2,2-dimethylbenzofuran-7-yl, 6-halo-2,3-dihydro-2,2-dimethylbenzofuran-4-yl, 5-halo-2,3-dihydro-2,2-dimethylbenzofuran-7-yl, or 2,3-dihydro-2,2-dimethyl-3-benzofuranon-4-yl.

Each of the above novel substituted phenyl quinazoline compounds per se falling within the scope of Formula (I) are preferred because of their high insecticidal activity, and thus may be used in controlling insects by applying to the locus where control is desired an insecticidal amount of these compounds admixed in a suitable agricultural carrier. When applied to insect-infected crops such as cotton, vegetables, fruits or other crops, these compounds are highly effective against an array of insects, particularly those shown in the tables below.

For the purposes of this invention, as regards the above substituent groups, the following definitions apply:

The term alkyl, alone or as part of a larger moiety, includes straight or branched chained alkyl groups of 1 to 14 carbon atoms, preferably lower straight or branched alkyl of 1 to 6 carbon atoms; while halogen includes chlorine, bromine, fluorine and iodine atoms. The terms haloalkyl and haloalkoxy include straight or branched chain alkyl of 1 to 14 carbon atoms, preferably lower straight or branched alkyl of 1 to 6 carbon atoms, wherein one or more hydrogen atoms have been replaced with halogen atoms, as, for example, trifluoromethyl and 2,2,2-trifluoroethoxy, respectively. The terms lower alkoxy and lower dialkylamino include those moieties having 1 to 6 carbon atoms, e.g., ethoxy and N,N-dimethylamino, respectively.

The terms aryl and substituted aryl include phenyl and naphthyl, preferably phenyl or substituted phenyl, while the terms aroyl and substituted aroyl include benzoyl and naphthoyl, preferably benzoyl or substituted benzoyl.

The term "substituted" as described above, when applied to the substituted aryl, aroyl, and thienyl moieties of W, X, Y, and Z in formula I, above, includes such substituents as lower alkyl, halogen, lower haloalkyl, lower alkoxy, lower haloalkoxy, lower alkoxyalkyl, carboxy, lower alkoxycarbonyl, cyano, nitro, aminocarbonyl, lower alkylsulfonyl, lower alkylcarbonylamino, lower alkylsulfonylamino, lower alkylthio, lower alkylsulfonyl, formyl, lower alkoxycarbonyl, phenyl, phenyl substituted with one or more halogens or lower haloalkyl, phenoxy, phenoxy substituted with one or more halogens, arylalkoxy, arylalkoxy substituted with halogen or lower alkyl, aryloxyalkoxy, aryloxyalkoxy substituted with lower alkylsulfonyl, or lower alkyl, or dialkylsilylalkoxy.

Groups other than aryl, aroyl, and thienyl which may also be substituted include arylalkylamino or arylaminoalkyl (where the aryl groups may be substituted with e.g., lower alkoxy or carboxyalkoxy); arylalkylimino (where the aryl group may be substituted with, e.g., lower alkoxy); aryla- lkycarbonylamino (where the aryl group may be substituted with, e.g. halogen); (aryl)(alkyl)aminoalkyl (where the aryl group may be substituted with, e.g. dicarboxyalkylaminocarbonyl); and (aryl)(halo)alkenyl (where the aryl group may be substituted with halogen, lower alkyl, lower haloalkyl, cyano, carboxy, lower alkoxycarbonyl, or aminocarbonyl).

Illustrations of the substituted phenyl groups further include such moieties as:

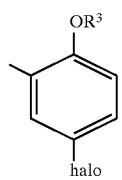

wherein R$^3$ is hydrogen; alkyl, (e.g. methyl, 1-methylethyl, n-pentyl, or undecyl); tri(lower alkyl)silylalkyl; (4-halophenyl)lower alkyl; pentahalophenylalkyl; pyridin-2-ylalkyl; or 2-(4-alkylsulfonylphenoxy)ethyl, or the like.

In addition, the term arylalkyl includes 2-(naphth-2-yl) ethyl; arylalkenyl includes 2-(naphth-2-yl)ethenyl; arylthio includes 3,4-dichlorophenylthio and naphth-2-ylthio; arylsulfinyl includes 3,4-dichlorophenylsulfinyl and naphth-2-ylsulfinyl; while arylsulfonyl includes 3,4-dichlorophenylsulfonyl and naphth-2-ylsulfonyl.

DETAILED DESCRIPTION OF THE INVENTION

Synthesis of The Compounds

The compounds employed as insecticides in accordance with this invention are generally known to those skilled in the art, including commercial preparations thereof, or may readily be prepared from these compounds by known methods. These and other methods are described in further detail in the description and examples below.

Thus, in general, the majority of the quinazoline products (formula I above) can be prepared by the cyclization of the appropriately substituted 2-aminobenzonitrile with chloroformamidine hydrochloride in diglyme, as taught by Harris et al, [J. Med. Chem., 33, 434–444 (1990)] and as further shown in Step 1 of Example 1, below. The starting 2-aminobenzonitriles are also generally available commercially, but may be prepared in accordance with the processes taught in each of Examples 2, 6, and 20–26. In these examples, the desired 2-aminobenzonitrile starting materials substituted with halogen may be prepared by the reaction of either 2-aminobenzonitrile, 2-amino-5-chlorobenzonitrile, or 2-amino-6-chlorobenzonitrile with 1 or 2 equivalents of N-bromosuccinimide or 1 equivalent of N-chlorosuccinimide in N,N-dimethylformamide. Intermediates prepared by this method include the following benzonitriles:

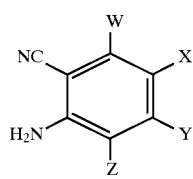

wherein, alternatively,
X and Z are Br;
X is Br;
X is Cl, and Z is Br;

X and Z are Cl;

W is Cl, and X is Br;

X is Br, and Z is Cl; or

W is Cl, and X and Z are Br;

with the proviso that unless otherwise specified, W, X, Y, and Z are hydrogen.

The halogenated 2-aminobenzonitrile intermediates thus prepared may then be either reacted to prepare the quinazolines (I) as previously described, or used to prepare other substituted 2-aminobenzonitrile intermediates, as described below.

For example, 2-amino-5-bromo-6-chlorobenzonitrile, or 2-amino-3,5-dibromobenzonitrile, can be further reacted with 1 or 2 equivalents of an optionally substituted-phenylboronic acid in the presence of tetrakis (triphenylphosphine)palladium(0) in aqueous sodium carbonate and toluene to form more complex substituted 2-aminobenzonitrile intermediates (B), as listed below. Substituted 2-aminobenzonitrile intermediates (B) prepared in this manner include, for example, 2-amino-6-chloro-5-(5-chloro-2-methoxyphenyl)benzonitrile and 2-amino-6-chloro-5-(3,5-dichlorophenyl)benzonitrile. These optionally substituted-phenylboronic acid intermediates are commercially available, or may be prepared by the method of Thompson and Gaudino [JOC., 49, 5237–5243 (1984)]. Step D of Example 1, Steps B–D of Example 2, and Step A of Example 5 provide detailed descriptions of how these reactions may be conducted.

Intermediates prepared by this foregoing method include those of the formula:

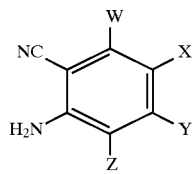

wherein Y is hydrogen and W, X and Z are as defined in the following table:

| W | X | Z |
|---|---|---|
| H | Phenyl | Phenyl |
| H | Phenyl | H |
| H | Cl | Phenyl |
| H | Phenyl | Cl |
| Cl | Phenyl | H |
| Cl | Phenyl | Phenyl |
| Cl | 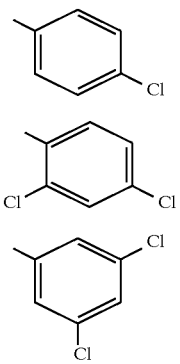 | H |
| Cl | (3,5-dichlorophenyl) | H |
| Cl | (3-chloro-5-chlorophenyl) | H |
| Cl | (2-chloro-4-fluorophenyl) | H |
| Cl | (4-fluorophenyl) | H |
| Cl | (2-methoxy-4-chlorophenyl) | H |
| H | (4-tert-butylphenyl) | H |
| H | (3,5-bis(trifluoromethyl)phenyl) | H |
| Cl | (3,5-bis(trifluoromethyl)phenyl) | H |
| (3,5-bis(trifluoromethyl)phenyl) | (3,5-bis(trifluoromethyl)phenyl) | H |
| Cl | (1-naphthyl) | H |

Alternatively, 2-aminobenzonitrile intermediates substituted with alkyl may be prepared by the method of Harris et al., J. Med. Chem., 33, 434–444 (1990) by the transfer hydrogenation of the alkyl-substituted 2-nitrobenzonitrile in the presence of 10% palladium on carbon in cyclohexene and ethanol, yielding the corresponding alkyl-substituted 2-aminobenzonitrile, for example, 6-methyl-2-aminobenzonitrile. The thus-prepared 6-methyl-2-aminobenzonitrile may then be halogenated with N-bromosuccinimide or N-iodosuccinimide in N,N-dimethylformamide, yielding the corresponding 2-amino-5-halo-6-methylbenzonitrile, which in turn can be reacted with 1 equivalent of, for example, a substituted-phenylboronic acid or a benzo-fused oxygen-containing heterocyclylboronic acid, affording the corresponding 2-amino-5-substituted-6-methylbenzonitrile, for example, 2-amino-5-[3,5-di(trifluoromethyl)phenyl]-6-methylbenzonitrile, or 2-amino-5-(2,3-dihydro-2,2,6-trimethyl-benzofuran-4-yl)-6-methylbenzonitrile. Steps B–D of Example 1, Step A of Example 17, and Steps A–F of Example 30 provide detailed descriptions of how these intermediates may be prepared.

Intermediates prepared by these latter methods include those having the formula:

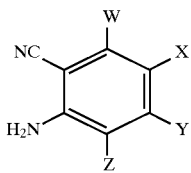

wherein Y and Z are hydrogen, and W and X are as follows:

| W | X |
|---|---|
| —CH₃ | 3,5-bis(CF₃)phenyl |
| —CH₃ | 4-C(CH₃)-phenyl |
| —CH₃ | 3-CH₃-phenyl |
| —CH₃ | 3,5-di-CH₃-phenyl |
| —CH₃ | Phenyl |
| —CH₃ | 3,5-di-Cl-phenyl |
| —CH₃ | 2,2-dimethyl-7-methylbenzofuran-type (H₃C, O, CH₃, CH₃) |
| —CH₃ | Cl-substituted 2,2-dimethylbenzofuran (Cl, O, CH₃, CH₃) |
| —CH₃ | F₃C-substituted 2,2-dimethylbenzofuran |

-continued

| W | X |
|---|---|
| —CH₃ | F-substituted 2,2-dimethylbenzofuran |
| —CH₃ | Cl-substituted 2,2-dimethylbenzofuran |

Other intermediates, as well as the qunizaoline products falling within formula (I) above and Table I below, may be prepared from the foregoing or analogous compounds by these or analogous methods known to those skilled in the art and/or those described below and in the examples.

For example, the 2-aminobenzonitrile intermediate, 2-amino-5-(2-phenylethyl)benzonitrile, may be prepared using the method of Taylor and Ray [JOC., 52, 3997–4000 (1987)], by the palladium-catalyzed coupling of 2-amino-5-bromobenzonitrile with phenylacetylene, yielding 2-amino-5-(2-phenylethynyl)benzonitrile. The thus-prepared ethynyl compound can then be hydrogenated in the presence of 10% palladium on carbon, yielding 2-amino-5-(2-phenylethyl)benzonitrile. Steps B and C of Example 6 provide a detailed description of how these reactions are conducted.

Other 2-aminobenzonitrile intermediates substituted with a sulfurbridging moiety, for example, naphth-2-ylthio, may be prepared by the method of Ashton and Hynes [J. Med. Chem., 16, 1233–1237 (1973)] by the alkylation of an appropriate arylthiol with a halogenated 2-nitrobenzonitrile in the presence of potassium carbonate, yielding, for example, 2-nitro-5-(naphth-2-ylthio)benzonitrile. Reduction of the nitro group with stannous chloride dihydrate affords the corresponding 2-aminobenzonitrile intermediates. Examples 7 and 9 provide detailed descriptions of how these reactions are conducted.

A number of the quinazolines (I), or modifications thereof, may be further reacted to obtain other quinazoline derivatives falling within the scope of formula I above. For example, 2,4,6-triamino-5-methylquinazoline is prepared in a step-wise manner by the nitration of 2-chloro-6-methylbenzonitrile, yielding the corresponding 2-chloro-6-methyl-5-nitrobenzonitrile. The 5-nitro compound may in turn be cyclyzed with guanidine carbonate in 2-ethoxyethanol, affording 2,4-diamino-5-methyl-6-nitroquinazoline. These two steps of the synthesis are described in detail in Example 12. The 6-nitroquinazoline can be reduced to the corresponding 2,4,6-triamino-5-methylquinazoline by hydrogenation in the presence of 10% palladium on carbon. Example 13 describes in detail this step in the reaction sequence.

In a similar manner 2,4,6-triaminoquinazoline and 2,4,6-triamino-5-chloroquinazoline can be prepared. This is accomplished by the nitration of, for example, 2,4-diamino-5-chloroquinazoline (above) with 90% nitric acid and sulfuric acid, yielding the corresponding 2,4-diamino-5-chloro-6-nitroquinazoline. The 6-nitroquinazoline is in turn reduced by either hydrogenation in the presence of 10% palladium on carbon or by treatment with stannous chloride dihydrate, affording the corresponding 2,4,6-triaminoquinazoline. Steps A and B of Example 15 describe in detail these two steps in the reaction sequence.

The 2,4,6-triaminoquinazoline derivatives described above may then optionally be treated with 2N hydrochloric acid, sodium nitrite, potassium cyanide, and copper(II) sulfate pentahydrate in water, affording the corresponding 2,4-diamino-6-cyanoquinazoline, for example, 2,4-diamino-6-cyano-5-methylquinazoline. Step A of Example 14 describes in detail this step in the reaction sequence.

The above 2,4-diamino-6-cyanoquinazoline intermediates may be further reacted with a substituted aniline, for example, 3,4,5-trimethoxyaniline, and hydrogen in the presence of Raney nickel in water and acetic acid, affording the corresponding 2,4-diamino-6-(substituted-aminomethyl) quinazolines. Step B of Example 14 describes in detail the preparation of this class of compounds.

In a similar manner, 2,4,6-triamino-5-chloroquinazoline can be reacted with 3,4,5-trimethoxybenzaldehyde and hydrogen in the presence of Raney nickel in 2-ethoxyethanol, affording the corresponding 2,4-diamino-6-[(3,4,5-trimethoxyphenylmethyl)imino]quinazoline. Step C of Example 15 describes in detail the preparation of this compound. In a similar manner there may also be prepared 2,4-diamino-6-(substituted-aminomethyl)quinazolines.

A series of quinazoline analogs may be prepared from the above 2,4-diamino-5-chloro-6-(5-chloro-2-methoxyphenyl) quinazoline. This is accomplished by the reaction of 2,4-diamino-5-chloro-6-(5-chloro-2-methoxyphenyl) quinazoline with 1M boron tribromide in methylene chloride, yielding the corresponding 2,4-diamino-5-chloro-6-(5-chloro-2-hydroxyphenyl)quinazoline. The hydroxy intermediate in turn is reacted with a halogen-containing compound and potassium carbonate in N,N-dimethylformamide, affording the appropriately 6-(5-chloro-2-substituted-phenyl)quinazoline, for example, 2,4-diamino-5-chloro-6-[5-chloro-2-(pyridin-2-ylmethoxy) phenyl]quinazoline. Example 3 describes in detail the preparation of this compound.

Other like analogs of quinazoline may be prepared in a similar manner. Quinazoline derivatives containing a sulphur bridge, for example those whose preparations are taught in Examples 7 and 9, can be oxidized to the corresponding sulfinyl derivatives using the method of Oae et al., [Bull. Chem. Soc. Japan, 39, 364–366 (1966)], by the treatment of, for example, 2,4-diamino-6-(3,4-dichlorophenylthio)quinazoline with the bromine complex of 1,4-diazabicyclo(2,2,2)-octane in aqueous 70% acetic acid. Example 11 describes in detail the preparation of 2,4-diamino-6-(3,4-dichlorophenylsulfinyl)quinazoline. The corresponding sulfonyl derivatives may then be prepared by treatment of these sulfur bridged quinazolines with potassium permanganate in acetic acid and water. Examples 8 and 10 describe in detail the preparation of these compounds.

Compounds of formula (I) above, wherein the 2,4-diamino moieties are substituted, e.g., Compounds 272–274 of Table 1, may be prepared by the reaction of a 2,4-diaminoquinazoline with an appropriately substituted formamidine dimethyl acetal, for example, dimethylformamidine dimethyl acetal, yielding the corresponding 2,4-di (substituted-amino)quinazoline, for example, 2,4-di (dimethylaminomethyleneamino)-5-methyl-6-[3,5-di (trifluoromethyl)phenyl]quinazoline. Example 28 describes in detail the preparation of these compounds.

Other 2,4-di(substituted-amino) compounds, e.g., Compounds 215–217 and 251–271 of Table 1, may also be prepared by the reaction of a 2,4-diaminoquinazoline with other reactants, such as an appropriately substituted anhydride, for example, 3,6,9-trioxadecanoic anhydride, under basic conditions in the presence of dimethylaminopyridine, yielding the corresponding 2,4-di (substituted-ami no)quinazoline, for example, 2,4-di(1-oxo-3,6,9-trioxadecaneamino)-5-methyl-6-[3,5-di (trifluoromethyl)phenyl]-quinazoline. Example 32 describes in detail the preparation of these compounds.

Compounds of formula (I) above, wherein X is aroyl or substituted aroyl, e.g. Compounds 149–173 of Table 1, may be prepared in a step-wise manner using methods known from the open literature. Using the method of Beletskaya et al., (Bumagin et. al., Dokl. Akad. Nauk SSSR, 320(3), 619–622 (1991)) an appropriately substituted aryl iodide, for example, 2-amino-5-iodo-6-methylbenzonitrile, may be carbonylated under about one atmosphere of pressure with carbon monoxide and tetramethylammonium tetra (optionally-substituted-phenyl)borate in the presence of a catalytic amount of palladium acetate, yielding the corresponding ketone, for example, 2-amino-5-(4-trifluoromethylphenylcarbonyl)-6-methylbenzonitrile. The ketone may then be cyclized with chloroformamidine hydrochloride in 2-methoxyethyl ether, a method previously described, affording the targeted quinazoline derivative, for example, 2,4-diamino-5-methyl-6-(4-trifluoromethyl-phenylcarbonyl)quinazoline. Example 19, discusses in detail this reaction sequence. Compounds of formula (I) above, wherein X is substituted aryloxy. e.g., Compounds 242–250 of Table 1, may also be prepared in a step-wise manner. For example, the sodium salt of an appropriately substituted phenol may be reacted with 5-chloro-2-nitrobenzonitrile, yielding the corresponding 5-(substituted-phenoxy)-2-nitrobenzonitrile. The so-prepared 2-nitrobenzonitrile may then be reduced with iron powder and hydrochloric acid in water and ethanol, affording 2-amino-5-(substituted-phenoxy)benzonitrile. The 2-aminobenzonitrile may then be cyclized with chloroformamidine hydrochloride in 2-methoxyethyl ether, a method previously described, affording the targeted quinazoline derivative, for example, 2,4-diamino-6-(4-chlorophenoxy)quinazoline. Example 28, discusses in detail this reaction sequence.

Compounds where X is arylalkylcarbonylamino, e.g., Compounds 174 and 175 of Table 1, may be prepared, by the reaction of a 2,4,6-triaminoquinazoline, for example, 2,4,6-triamino-5-chloroquinazoline (Compound 24) with an appropriate arylalkylcarbonyl halide under basic conditions, or they may be obtained commercially from Dr. John B. Hynes, Dept. of Pharmaceutical Sciences, Medical University of South Carolina, 171 Ashley Avenue, Charleston, S.C. 29425-2303.

Agriculturally acceptable salts, e.g., Compounds 275–278 of Table 1, may be prepared by methods known to those skilled in the art.

EXAMPLES

The following examples, which disclose the preparation of representative compounds of this invention (Table 1), are for the purpose of illustrating known methods for the preparation of the compounds employed in the methods and formulations of this invention, including certain novel quinazoline compounds per se (Compounds 43–45, 47–74, 106–138, 142–173, and 176–284).

Example 1

SYNTHESIS OF 2,4-DIAMINO-5-METHYL-6-[3,5-DI(TRIFLUOROMETHYL)PHENYL]QUINAZOLINE (COMPOUND 63)

Step A Synthesis of chloroformamidine hydrochloride as an intermediate

Diethyl ether, 600 mL, was cooled in an ice-bath and saturated with about 50 grams of hydrogen chloride gas. With vigorous stirring, a solution of 26.4 grams (0.628 mole) of cyanamide in 500 mL of diethyl ether was added during a 15 minute period. Upon completion of addition, the ice-bath was removed and the reaction mixture was allowed to stir for about 15 minutes. A white, solid precipitate was collected by filtration and washed with diethyl ether. The solid was dried under reduced pressure, yielding 50.3 grams of chloroformamidine hydrochloride.

Step B Synthesis of 2-amino-6-methylbenzonitrile as an intermediate

A stirred solution of 13.8 grams (0.085 mole) of 2-methyl-6-nitrobenzonitrile, 28 mL of cyclohexene, and 1.5 gram of 10% palladium on charcoal in 280 mL of ethanol was heated at reflux for about 3 hours. After this time, the reaction mixture was filtered to remove the catalyst. The filtrate was concentrated under reduced pressure to a solid residue. The solid was triturated with 50 mL of methylene chloride, and the insoluble material was collected by filtration. Upon standing, crystals formed in the filtrate. The crystals were collected by filtration and were washed quickly with a minimum amount of methylene chloride. An NMR spectrum of the crystals, 2.3 grams, mp 125°–126° C., indicated that they were sought-after product. A second crop of product, 1.8 grams, was collected from the methylene chloride-filtrate combination. The insoluble material from the trituration was dissolved in methylene chloride and methanol and passed through a pad of diatomaceous earth. The filtrate was concentrated under reduced pressure, yielding 4.5 grams of solid. The NMR spectrum of the solid indicated that it too was the sought-after product. The total yield of 2-amino-6-methylbenzonitrile was about 8.6 grams.

Step C Synthesis of 2-amino-5-bromo-6-methylbenzonitrile as an intermediate

A stirred solution of 8.3 grams (0.063 mole) of 2-amino-6-methylbenzonitrile in 125 mL of N,N-dimethylformamide was cooled in an ice bath, and a solution of 11.2 grams (0.063 mole) of N-bromosuccinimide in 125 mL of N,N-dimethylformamide was added dropwise during a 30 minute period, while maintaining the reaction mixture temperature at about 15°–25° C. Upon completion of addition, the reaction mixture was stirred at ambient temperature for about 20 hours. After this time, the reaction mixture was poured into 1 liter of aqueous 3N sodium hydroxide. The mixture was then diluted to a volume of about 1700 mL with distilled water. A solid precipitate was collected by filtration and dried under reduced pressure, yielding 12.3 grams of 2-amino-5-bromo-6-methylbenzonitrile, mp 111°–113° C. The NMR spectrum was consistent with the proposed structure.

Step D Synthesis of 2-amino-6-methyl-5-[3,5-di(trifluoromethyl)phenyl]-benzonitrile as an intermediate A stirred solution of 1.7 grams (0.008 mole) of 2-amino-5-bromo-6-methylbenzonitrile, 3.2 grams (0.012 mole) of 3,5-di(trifluoromethyl)-phenylboronic acid, 4.3 grams (0.031 mole) of potassium carbonate and 0.3 mL of tetrakis(triphenylphosphine)palladium(0) in 150 mL of toluene was heated at 90° C. for about 20 hours. After this time, the reaction mixture was stirred with 100 mL of water, and the organic layer was separated. The organic layer was concentrated under reduced pressure to a residue. The residue was subjected to column chromatography on silica gel, using 30/65/5 and 20/60/20 methylene chloride/petroleum ether/ethyl acetate as eluants. The product-containing fractions were combined and concentrated under reduced pressure, yielding about 1.0 gram of 2-amino-6-methyl-5-[3,5-di(trifluoromethyl)phenyl]benzonitrile. The NMR spectrum was consistent with the proposed structure.

Step E Synthesis of 2,4-diamino-6-methyl-5-[3,5-di(trifluoromethly)-phenyl]quinazoline (Compound 63)

A stirred mixture of 0.9 gram (0.003 mole) of 2-amino-6-methyl-5-[3,5-di(trifluoromethyl)phenyl]benzonitrile and 0.3 gram (0.003 mole) of chloroformamidine hydrochloride (prepared in Step A of this Example) in 11 mL of 2-methoxyethyl ether was gradually warmed to 165° C. during a 1.5 hour period. The heterogeneous mixture was maintained at 165° C. for about 4.5 hours. After this time, the reaction mixture was cooled and diluted with 200 mL of diethyl ether. The resultant precipitate, which was the hydrochloride salt of the sought-after product, was collected by filtration. The hydrochloride salt was recrystallized from n-propanol and water. The solid was converted to the free base by cooling it in an ice-water bath and stirring it with 30 mL of concentrated ammonium hydroxide during a one hour period. The resultant solid was collected by filtration, yielding 0.4 gram of 2,4-diamino-6-methyl-5-[3,5-di(trifluoromethyl)phenyl]quinazoline, mp 222°–225° C. The NMR spectrum was consistent with the proposed structure. NOTE: The compound of Example 1 was prepared by the method of Harris et al, [J. Med. Chem., 33, 434–444 (1990)]

Example 2

SYNTHESIS OF 2,4-DIAMINO-5-CHLORO-6-(5-CHLORO-2-METHOXYPHENYL)QUINAZOLINE (COMPOUND 66)

Step A Synthesis of 2-amino-5-bromo-6-chlorobenzonitrile as an intermediate

This compound was prepared in a manner analogous to that of Step C of Example 1, using 18.0 grams (0.010 mole) of N-bromosuccinimide, and 15.2 grams (0.010 mole) of 2-amino-6-chlorobenzonitrile in 200 mL of N,N-dimethylformamide. The yield of 2-amino-5-bromo-6-chlorobenzonitrile was 22.5 grams. The NMR spectrum was consistent with the proposed structure Step B Synthesis of 3-bromo-4-methoxychlorobenzene as an intermediate A rapidly stirred solution of 15.5 grams (0.074 mole) of 2-bromo-4-chlorophenol, 20.0 grams (0.145 mole) of anhydrous powdered potassium carbonate, and 10 mL (0.106 mole) of dimethyl sulfate in 150 mL of acetone was heated at reflux for about 18 hours. After this time, the reaction mixture was concentrated under reduced pressure to a residue. The residue was partitioned between 100 mL each of water and methylene chloride. The organic layer was removed and washed with an aqueous solution saturated with sodium chloride. The organic layer was then dried with magnesium sulfate and filtered. The filtrate was passed through a short column of silica gel. Elution was accomplished with 500 mL of methylene chloride. The eluate was concentrated under reduced pressure, yielding 16.3 grams of 3-bromo-4-methoxychlorobenzene. The NMR spectrum was consistent with the proposed structure.

Step C Synthesis of 5-chloro-2-methoxyphenylboronic acid as an intermediate

A stirred solution of 5.8 grams (0.026 mole) of 3-bromo-4-methoxychlorobenzene in 150 mL of tetrahydrofuran was cooled to −80° C., and 11.5 mL of n-butyllithium in hexanes (2.5 Molar–0.029 mole) was added dropwise during a 15 minute period, while maintaining the reaction mixture temperature at about −70° C. The initial reaction was very exothermic, which required cooling the reaction mixture to about −100° C. Upon completion of the addition, the reaction mixture was stirred at −80° C. for 15 minutes. After this time, 17.5 mL (0.076 mole) triisopropyl borate was added during a 1 minute period. The reaction mixture was then allowed to warm slowly to ambient temperature during a 3 hour period, where it was stirred for an additional 1 hour. After this time, the reaction mixture was concentrated under reduced pressure to a volume of about 50 mL. The concentrate was then poured into 500 mL of ice-water. The mixture was then made acidic with about 26 mL of aqueous 2N hydrochloric acid. The mixture was then filtered to collect a solid, which was dried, yielding 3.9 grams of 5-chloro-2-methoxyphenylboronic acid. The NMR spectrum was consistent with the proposed structure.

NOTE: A modification of the method of Thompson and Gaudino was used to prepare 5-chloro-2-methoxyphenylboronic acid, as shown above in Step C. [JOC., 49, 5237–5243 (1984)]

Step D Synthesis of 2-amino-6-chloro-5-(5-chloro-2-methoxyphenyl)benzonitrile as an intermediate A stirred mixture of 5.7 grams (0.020 mole) of 5-chloro-2-methoxyphenylboronic acid, 3.3 grams (0.014 mole) of 2-amino-5-bromo-6-chlorobenzonitrile (prepared in Step A of this Example), 21 mL of aqueous 2M sodium carbonate, and 0.15 gram (catalyst) of tetrakis(triphenylphosphine)palladium(0) in 50 mL of toluene was heated at reflux for about 17 hours. After this time, 50 mL of ethyl acetate was added to the reaction mixture. The organic layer was separated and washed with 50 mL of water and then with 50 mL of an aqueous solution saturated with sodium chloride. The organic layer was then dried with magnesium sulfate and filtered. The filtrate was concentrated under reduced pressure to a residue. The residue was subjected to column chromatography on silica gel. Elution was accomplished using methylene chloride. The product-containing fractions were combined and concentrated under reduced pressure, yielding 3.8 grams of 2-amino-6-chloro-5-(5-chloro-2-methoxyphenyl)benzonitrile. The NMR spectrum was consistent with the proposed structure.

Step E Synthesis of 2,4-diamino-5-chloro-6-(5-chloro-2-methoxyphenyl)quinazoline (Compound 66)

This compound was prepared in a manner analogous to that of Step E of Example 1, using 3.8 grams (0.013 mole) of 2-amino-6-chloro-5-(5-chloro-2-methoxyphenyl)benzonitrile and 1.8 grams (0.016 mole) of chloroformamidine hydrochloride in 13 mL of 2-methoxyethyl ether. The yield of 2,4-diamino-5-chloro-6-(5-chloro-2-methoxyphenyl)quinazoline was 2.8 grams. The NMR spectrum was consistent with the proposed structure.

Example 3

SYNTHESIS OF 2,4-DIAMINO-5-CHLORO-6-[5-CHLORO-2-(PYRIDIN-2-YLMETHOXY)PHENYL]QUINAZOLINE (COMPOUND 73)

Step A Synthesis of 2,4-diamino-5-chloro-6-(5-chloro-2-hydroxyphenyl)quinazoline (Compound 65) as an intermediate A solution of 2.8 grams (0.084 mole) of 2,4-diamino-5-chloro-6-(5-chloro-2-methoxyphenyl)quinazoline (prepared in Example 2) in 300 mL of methylene chloride was stirred, and 35 mL of 1.0M boron tribromide in methylene chloride was added. Upon completion of addition, the reaction mixture was stirred at ambient temperature for about 21 hours. Thin layer chromatographic analysis of the reaction mixture indicated that the reaction was not complete. The reaction mixture was heated at reflux for about 6 hours, then it was allowed to cool to ambient temperature where it was stirred for about 60 hours. After this time, the reaction mixture was poured into 500 mL of ice containing 100 mL of concentrated ammonium hydroxide. The mixture was filtered to collect a solid. The solid was washed with water and dried at 70° C. under reduced pressure, yielding 2.4 grams of 2,4-diamino-5-chloro-6-(5-chloro-2-hydroxyphenyl)quinazoline. The NMR spectrum was consistent with the proposed structure.

Step B Synthesis of 2,4-diamino-5-chloro-6-[5-chloro-2-(pyridin-2-yl-methoxy)phenyl]quinazoline (Compound 73)

Under a nitrogen atmosphere, a stirred solution of 0.5 gram (0.002 mole) of 2,4-diamino-5-chloro-6-(5-chloro-2-hydroxyphenyl)quinazoline, 0.3 gram (0.002 mole) of pyridin-2-ylmethyl chloride hydrochloride, and 0.5 gram (0.004 mole) of potassium carbonate in 5 mL of N,N-dimethylformamide was heated at 60° C. for about 24 hours. After this time, the reaction mixture was concentrated under reduced pressure to a residue. The residue was taken up in 100 mL of water and was stirred for about 2 hours. The resultant solid was collected by filtration, yielding 0.6 gram of 2,4-diamino-5-chloro-6-[5-chloro-2-(pyridin-2-ylmethoxy)phenyl]quinazoline. The NMR spectrum was consistent with the proposed structure.

Example 4

SYNTHESIS OF 2,4-DIAMINO6-BROMO-5-CHLOROQUINAZOLINE (COMPOUND 20)

This compound was prepared in a manner analogous to that of Step E of Example 1, using 2.4 grams (0.010 mole) of 2-amino-5-bromo-6-chlorobenzonitrile (prepared as in Step A of Example 2) and 1.4 grams (0.012 mole) of chloroformamidine hydrochloride in 10 mL of 2-methoxyethyl ether. The yield of 2,4-diamino-6-bromo-5-chloroquinazoline was 2.4 grams. The NMR spectrum was consistent with the proposed structure.

Example 5

SYNTHESIS OF 2,4-DIAMINO-5-CHLORO-6-(3,5-DICHLOROPHENYL)QUINAZOLINE (COMPOUND 51)

Step A Synthesis of 2-amino-6-chloro-5-(3,5-dichlorophenyl)benzonitrile as an intermediate This compound was prepared in a manner analogous to that of Step D of Example 1, using 2.3 grams (0.010 mole) of 2-amino-5-bromo-6-chlorobenzonitrile (prepared as in Step A of Example 2), 2.9 grams (0.015 mole) of 3,5-dichlorophenylboronic acid, 0.1 gram (catalyst) of tetrakis(triphenylphosphine)palladium(0), and 30 mL of aqueous 2M sodium carbonate in 75 mL of toluene. The solid product was recrystallized from toluene, yielding 1.9 grams of 2-amino-6-chloro-5-(3,5-dichlorophenyl)benzonitrile. The NMR spectrum was consistent with the proposed structure.

Step B Synthesis of 2,4-diamino-5-chloro-6-(3,5-dichlorophenyl)quinazoline (Compound 51)

This compound was prepared in a manner analogous to that of Step E of Example 1, using 1.5 grams (0.005 mole) of 2-amino-6-chloro-5-(3,5-dichlorophenyl)benzonitrile and 0.7 gram (0.006 mole) of chloroformamidine hydrochloride in 10 mL of 2-methoxyethyl ether. The solid was recrystallized from methanol, yielding 0.5 gram of 2,4-diamino-5-chloro-6-(3,5-dichlorophenyl)quinazoline. The NMR spectrum was consistent with the proposed structure; however, methanol was present in the sample.

Example 6
SYNTHESIS OF 2,4-DIAMINO-6-(2-PHENYLETHYL) QUINAZOLINE (COMPOUND 79)
Step A Synthesis of 2-amino-5-bromobenzonitrile as an intermediate This compound was prepared in a manner analogous to that of Step C of Example 1, using 6.0 grams (0.051 mole) of 2-aminobenzonitrile and 9.0 grams (0.051 mole) of N-bromosuccinimide in 75 mL of N,N-dimethylformamide. The yield of 2-amino-5-bromobenzonitrile was 8.6 grams. The MR spectrum was consistent with the proposed structure.

Step B Synthesis of 2-amino-5-(2-phenylethynyl) benzonitrile as an intermediate

A solution of 3.00 grams (0.015 mole) of 2-amino-5-bromobenzonitrile and 2.3 mL (0.021 mole) of phenylacetylene in 50 mL of acetonitrile was stirred, and 10.6 mL of triethylamine, 0.13 gram of copper iodide, and 0.29 gram of bis(triphenylphosphine)palladium(II) chloride were added in order. Upon completion of addition, the reaction mixture was stirred at ambient temperature for about 20 hours. After this time, thin layer chromatographic (TLC) analysis of the reaction mixture indicated that no reaction had taken place. The reaction mixture was warmed to 70° C., where it was stirred for about 7.5 hours. An additional 0.38 gram of phenylacetylene was added, and the reaction mixture was warmed to reflux temperature where it was stirred during about an additional 16.5 hour period. After this time, TLC analysis of the reaction mixture indicated that it contained about a 1 to 1 mixture of starting bromobenzonitrile and product. An additional 5.0 mL of triethylamine and 0.09 gram of bis(triphenylphosphine)palladium(II) chloride catalyst was added to the reaction mixture, and the heating at reflux was continued during an additional 24 hour period. After this time, the reaction mixture was concentrated under reduced pressure to a residue. The residue was dissolved in ethyl acetate, and the solution was washed with 50 mL of aqueous, dilute hydrochloric acid. The organic layer was dried with magnesium sulfate and filtered. The filtrate was concentrated under reduced pressure to a residue. The residue was subjected to column chromatography on silica gel. Elution was accomplished using 15/10/75 tetrahydrofuran/methylene chloride/petroleum ether. The product-containing fractions were combined and concentrated under reduced pressure, yielding 0.85 gram of 2-amino-5-(2-phenylethynyl)benzonitrile. The NMR spectrum was consistent with the proposed structure.
NOTE: The method of Taylor and Ray was used to prepare 2-amino-5-(2-phenylethynyl)benzonitrile, as shown above in Step B. [JOC., 52, 3997–4000 (1987)]
Step C Synthesis of 2-amino-5-(2-phenylethyl)benzonitrile as an intermediate A solution of 0.85 gram (0.004 mole) of 2-amino-5-(2-phenylethynyl)benzonitrile in 150 mL of ethanol was prepared, and 0.2 gram (catalyst) of 10% palladium on carbon was added. The mixture was then hydrogenated using a Parr hydrogenator. Upon completion of the uptake of the theoretical amount of hydrogen, the reaction mixture was filtered and concentrated under reduced pressure to a residue. The residue was dried under reduced pressure, yielding 0.74 gram of 2-amino-5-(2-phenylethyl) benzonitrile. The NMR spectrum was consistent with the proposed structure.
Step D Synthesis of 2,4-diamino-6-(2-phenylethyl) quinazoline (Compound 79)

This compound was prepared in a manner analogous to that of Step E of Example 1, using 0.74 gram (0.003 mole) of 2-amino-5-(2-phenylethyl)benzonitrile and 0.41 gram (0.004 mole) of chloroformamidine hydrochloride in 11 mL of 2-methoxyethyl ether. The yield of 2,4-diamino-6-(2-phenylethyl)quinazoline was 0.66 gram, mp 178°–180° C., sl. decomp. The NMR spectrum was consistent with the proposed structure.

Example 7
SYNTHESIS OF 2,4-DIAMINO-6-(NAPHTH-2-YLTHIO) QUINAZOLINE (COMPOUND 88)
Step A Synthesis of 2-nitro-5-(naphth-2-ylthio)benzonitrile as an intermediate A stirred solution of 10.0 grams (0.055 mole) of 5-chloro-2-nitrobenzonitrile and 8.8 grams (0.055 mole) of 2-naphthalenethiol in 80 mL of N,N-dimethylformamide was cooled to 0° C., and 7.6 grams (0.055 mole) of potassium carbonate was added. Upon completion of addition, the reaction mixture was stirred at 0° C. for 1 hour. Thin layer chromatographic (TLC) analysis of the reaction mixture after this time indicated that the reaction had not gone to completion. The reaction mixture was then allowed to warm to ambient temperature, where it was stirred for about 18 hours. The reaction mixture was stirred with 80 mL of pyridine and then was diluted with water until a solid precipitate formed. The solid was collected by filtration and was washed in turn with an aqueous solution of 10% pyridine, water, an aqueous solution of 1 % hydrochloric acid, and finally with water. The solid was then dissolved in ethyl acetate and dried with magnesium sulfate. The mixture was filtered, and the filtrate was concentrated under reduced pressure to a residual solid. The solid was subjected to column chromatography on silica gel. Elution was accomplished with 10% ethyl acetate in heptane. The product-containing fractions were combined and concentrated under reduced pressure, yielding 13.5 grams of 2-nitro-5-(naphth-2-ylthio)benzonitrile. A small sample was recrystallized from ethyl acetate/hexane, mp 139°–140° C. The NMR spectrum was consistent with the proposed structure.
Step B Synthesis of 2-amino-5-(naphth-2-ylthio) benzonitrile as an intermediate A stirred solution of 13.0 grams (0.042 mole) of 2-nitro-5-(naphth-2-ylthio)benzonitrile in 200 mL of 2-methoxyethyl ether was cooled to 0° C., and a solution of 30.3 grams (0.134 mole) of stannous chloride dihydrate in 91 mL of concentrated hydrochloric acid was added. Upon completion of addition, the reaction mixture was allowed to warm to ambient temperature, where it was stirred during a 2 hour period. After this time, the reaction mixture was poured, with stirring, into a mixture of 260 grams of aqueous 50% potassium hydroxide in 300 grams of ice. An oily material, which dropped out of the solution, ultimately solidified. The solid was collected by filtration and was washed with water. The solid was dissolved in methylene chloride and was dried with magnesium sulfate. The mixture was filtered, and the filtrate was concentrated under reduced pressure, yielding 12.0 grams of 2-amino-5-(naphth-2-ylthio)benzonitrile. The NMR spectrum was consistent with the proposed structure.
Step C Synthesis of 2,4-diamino-6-(naphth-2-ylthio) quinazoline (Compound 88)

This compound was prepared in a manner analogous to that of Step E of Example 1, using 12.0 grams (0.043 mole) of 2-amino-5-(naphth-2-ylthio)benzonitrile and 5.5 grams (0.048 mole) of chloroformamidine hydrochloride in 25 mL of 2-methoxyethyl ether. The yield of 2,4-diamino-6-(naphth-2-ylthio)quinazoline was 12.7 grams. The NMR spectrum was consistent with the proposed structure.
NOTE: The compound of Example 7 was prepared by the method of Ashton and Hynes. [J. Med. Chem., 16, 1233–1237 (1973)]

Example 8
SYNTHESIS OF 2,4-DIAMINO-6-(NAPHTH-2-YLSULFONYL)QUINAZOLINE (COMPOUND 90)

A solution of 2.0 grams (0.006 mole) of 2,4-diamino-6-(naphth-2-ylthio)quinazoline (prepared in Example 7) in 80 mL of acetic acid was stirred, and a solution of 2.0 grams (0.013 mole) of potassium permanganate in 75 mL of water was added dropwise during a 1 hour period. Upon completion of addition, the reaction mixture was stirred at ambient temperature for about 18 hours. After this time, the reaction mixture was filtered through diatomaceous earth. The filtrate was made basic by adding an excess amount of concentrated ammonium hydroxide. The resultant precipitate was collected by filtration and was washed in turn with water, methanol, and acetone. The precipitate was stirred in hot N,N-dimethylformamide and treated with decolorizing carbon. The mixture was filtered hot, and the filtrate was set aside. The residue collected by the filtration was again stirred with hot N,N-dimethylformamide and filtered. The two filtrates were combined and poured into 500 grams of ice. The resultant solid was collected by filtration, yielding 0.9 gram of 2,4-diamino-6-(naphth-2-ylsulfonyl)quinazoline, mp 300°–302° C. The NMR spectrum was consistent with the proposed structure.

Example 9
SYNTHESIS OF 2,4-DIAMINO-6-(3,4-DICHLOROPHENYLTHIO)QUINAZOLINE (COMPOUND 80)

Step A Synthesis of 2-nitro-5-(3,4-dichlorophenylthio)benzonitrile as an intermediate This compound was prepared in a manner analogous to that of Step A of Example 7, using 10.1 grams (0.006 mole) of 5-chloro-2-nitrobenzonitrile, 9.9 grams (0.006 mole) of 3,4-dichlorobenzenethiol, 7.7 grams (0.006 mole) of potassium carbonate in 80 mL of N,N-dimethylformamide. The yield of 2-nitro-5-(3,4-dichlorophenylthio)benzonitrile was 15.9 grams, mp 136°–138° C. The NMR spectrum was consistent with the proposed structure.

Step B Synthesis of 2-amino-5-(3,4-dichlorophenylthio)benzonitrile as an intermediate This compound was prepared in a manner analogous to that of Step B of Example 7, using 15.9 grams (0.049 mole) of 2-nitro-5-(3,4-dichlorophenylthio)benzonitrile, 34.6 grams (0.153 mole) of stannous chloride dihydrate, and 100 mL of concentrated hydrochloric acid in 245 mL of diglyme. The yield of 2-amino-5-(3,4-dichlorophenylthio)benzonitrile was 15.2 grams, mp 126°–128° C. The NMR spectrum was consistent with the proposed structure.

Step C Synthesis of 2,4-diamino-6-(3,4-dichlorophenylthio)quinazoline (Compound 80)

This compound was prepared in a manner analogous to that of Step E of Example 1, using 14.7 grams (0.050 mole) of 2-amino-5-(2,4-dichlorophenylthio)benzonitrile and 6.3 grams (0.055 mole) of chloroformamidine hydrochloride in 30 mL of 2-methoxyethyl ether. The yield of 2,4-diamino-6-(3,4-di-chlorophenylthio)quinazoline was 12.2 grams, mp 232°–234° C. The NMR spectrum was consistent with the proposed structure.

Example 10
SYNTHESIS OF 2,4-DIAMINO-6-(3,4-DICHLOROPHENYLSULFONYL)QUINAZOLINE (COMPOUND 82)

This compound was prepared in a manner analogous to that of Example 8, using 2.0 grams (0.006 mole) of 2,4-diamino-6-(3,4-dichloro-phenylthio)quinazoline and 1.9 grams (0.012 mole) of potassium per-manganate in 80 mL of acetic acid and 75 mL of water. The yield of 2,4-diamino-6-(3,4-dichlorophenylsulfonyl)quinazoline was 0.6 gram, mp 286°–289° C. The NMR spectrum was consistent with the proposed structure.

Example 11
SYNTHESIS OF 2,4-DIAMINO-5-(3,4-DICHLOROPHENYLSULFINYL)QUINAZOLINE (COMPOUND 81)

Step A Synthesis of the bromine complex of 1,4-diazabicyclo(2,2,2)-octane as an intermediate A stirred solution of 2.2 grams (0.02 mole) of 1,4-diazabicyclo(2,2,2)octane in 10 mL of carbon tetrachloride was warmed to 40° C., and a solution of 3.2 grams (0.02 mole) of bromine in 15 mL of carbon tetrachloride was added dropwise. The resultant precipitate was collected by filtration, washed with carbon tetrachloride, and air-dried, yielding 5.0 grams of the bromine complex of 1,4-diazabicyclo(2,2,2)octane.

NOTE: The method of Oae et al. was used to prepare the bromine complex of 1,4-diazabicyclo(2,2,2)octane, as shown above in Step A. [Bull. Chem. Soc. Japan, 39, 364–366 (1966)]

Step B Synthesis of 2,4-diamino-6-(3,4-dichlorophenylsulfinyl)quinazoline (Compound 81)

A suspension of 5.0 grams (0.011 mole) of the bromine complex of 1,4-diazabicyclo(2,2,2)octane in 200 mL of aqueous 70% acetic acid was stirred, and 3.4 grams (0.01 mole) of 2,4-diamino-6-(3,4-dichlorophenylthio)quinazoline was added portionwise during about a 1 hour period. Upon completion of addition, the reaction mixture was stirred at ambient temperature for about 20 hours. After this time, the reaction mixture was neutralized with concentrated ammonium hydroxide. The resultant solid was collected by filtration and triturated with methanol. The solid was collected by filtration and dried, yielding 2,4-diamino-6-(3,4-dichlorophenylsulfinyl)quinazoline, mp 200° C., dec. The NMR spectrum was consistent with the proposed structure.

Example 12
SYNTHESIS OF 2,4-DIAMINO-5-METHYL-6-NITROQUINAZOLINE (COMPOUND 30)

Step A Synthesis of 2-chloro-6-methyl-5-nitrobenzonitrile as an intermediate

Under a nitrogen atmosphere, a stirred solution of aqueous 90% nitric acid was cooled to −35° C., and 40.0 grams (0.264 mole) of 2-chloro-6-methylbenzonitrile was added in one portion. The reaction mixture was then allowed to warm to ambient temperature, where it was stirred for about 18 hours. After this time, the reaction mixture was poured into 3000 mL of ice-water. After the ice melted, the resultant solid was collected by filtration and dried. The NMR spectrum of the solid indicated that it was about 75% pure product. The solid was recrystallized twice from methanol, yielding 13.9 grams of 2-chloro-6-methyl-5-nitrobenzonitrile, mp 85.5°–87.5° C. The NMR spectrum was consistent with the proposed structure. The filtrates from the recrystallizations were combined and concentrated under reduced pressure to a residue. The residue was subjected to column chromatography on silica gel. Elution was accomplished using 10% ethyl acetate in petroleum ether. The product-containing fractions were combined and concentrated under reduced pressure, yielding an additional 20.4 grams of 2-chloro-6-methyl-5-nitrobenzonitrile, mp 87.5°–89.5° C. The NMR spectrum was consistent with the proposed structure.

Step B Synthesis of 2,4-diamino-6-methyl-5-nitroquinazoline (Compound 30)

Under a nitrogen atmosphere, a stirred solution 29.5 grams (0.150 mole) of 2-chloro-6-methyl-5-nitrobenzonitrile and 54.0 grams (0.300 mole) of guanidine carbonate in 1500 mL of 2-ethoxyethanol was heated at reflux during a 3.5 hour period. After this time, the reaction mixture was concentrated under reduced pressure to a residue. The residue was stirred with 300 mL of water, and the resultant solid was collected by filtration. The solid was washed with 50 mL of water and dried under reduced pressure, yielding 27.2 grams of 2,4-diamino-5-methyl-6-nitroquinazoline. The NMR spectrum was consistent with the proposed structure. The reaction was repeated again.

Example 13

SYNTHESIS OF 2,4,6-TRIAMINO-5-METHYLQUINAZOLINE (COMPOUND 32)

A mixture of 5.0 grams (0.023 mole) of 2,4-diamino-5-methyl-6-nitroquinazoline (prepared in Example 12) and 0.5 gram (catalyst) of 10% palladium on carbon in 200 mL of ethanol was hydrogenated at 45°–50° C. using a Parr hydrogenator. The theoretical uptake of hydrogen required about 2.5 hours. The hydrogenation was repeated twice more, using 15.0 grams (0.068 mole) and 11.0 grams (0.050 mole), respectively, of 2,4-diamino-5-methyl-6-nitroquinazoline. The total yield of 2,4,6-triamino-5-methylquinazoline was 19.5 grams. The NMR spectra were consistent with the proposed structure.

Example 14

SYNTHESIS OF 2,4-DIAMINO-5-METHYL-6-[(3,4,5-TRIMETHOXYPHENYLAMINO)METHYL]QUINAZOLINE (COMPOUND 93)

Step A Synthesis of 2,4-diamino-6-cyano-5-methylquinazoline as an intermediate

Under a nitrogen atmosphere, a stirred solution of 2.5 grams (0.013 mole) of 2,4,6-triamino-5-methylquinazoline (prepared in Example 13) and 25 mL of 2N hydrochloric acid (0.050 mole) was cooled to 5° C., and a solution of 1.1 grams (0.016 mole) of sodium nitrite in 4 mL of water was added dropwise. Upon completion of addition, the reaction mixture was stirred at 5° C. during a 10 minute period. In a separate reaction vessel, a stirred solution of 14.7 grams (0.225 mole) of potassium cyanide in 70 mL of water was cooled to 5° C., and a solution of 1.4 grams (0.056 mole) of copper(II) sulfate pentahydrate in 100 mL of water was added dropwise. To this solution was added, portionwise, the reaction mixture containing the quinazoline diazonium salt prepared above. Upon completion of addition, the reaction mixture was allowed to warm to ambient temperature as it stirred during a 2 hour period. After this time, the reaction mixture was diluted with 60 mL of aqueous 50% potassium carbonate and was extracted with four 700 mL portions of tetrahydrofuran. The combined extracts were acidified with 50 mL of acetic acid, and the mixture was concentrated under reduced pressure to a residual solid. The solid was subjected twice to column chromatography on silica gel. Elution was accomplished in each case with 20% N,N-dimethylformamide in ethyl acetate. The product-containing fractions were combined and concentrated under reduced pressure, yielding 1.1 grams of 2,4-diamino-6-cyano-5-methylquinazoline. The NMR spectrum was consistent with the proposed structure; however, it showed that the product was in the form of the acetate salt.

Step B Synthesis of 2,4-diamino-5-methyl-6-[(3,4,5-trimethoxyphenylamino)methyl]quinazoline (Compound 93)

A mixture of 1.1 grams (0.005 mole) of 2,4-diamino-6-cyano-5-methylquinazoline, 4.6 grams (0.025 mole) 3,4,5-trimethoxyaniline and 2.0 grams (catalyst) of Raney nickel (50% slurry in water) in 30 mL of water and 70 mL of acetic acid was hydrogenated at 50 psi of hydrogen for 6 hours using a Parr hydrogenator. After this time the reaction mixture was filtered. The filter cake was slurried with a boiling mixture of 15 mL of water and 35 mL of acetic acid and was then filtered. The filtrates were combined and subjected to thin layer chromatography (TLC). The TLC analysis indicated that a small amount of the starting quinazoline remained unreacted. The filtrate was combined with 1.0 gram of Raney nickel and the mixture was again hydrogenated for an additional 1.5 hours using the Parr hydrogenator. After this time the reaction mixture was filtered and concentrated under reduced pressure to a residual oil. The residual oil was subjected to column chromatography on silica gel. Elution was accomplished initially using 25% N,N-dimethylformamide in ethyl acetate and, finally 40% N,N-dimethylformamide in ethyl acetate. The product-containing fractions were combined and concentrated under reduced pressure to a residual solid. The solid was recrystallized from water, yielding 0.5 gram of 2,4-diamino-5-methyl-6-[(3,4,5-trimethoxyphenylamino)methyl]quinazoline, mp 95°–210° C. The NMR analysis was consistent with the proposed structure; however, it indicated that the compound was a complex with acetic acid and water.

NOTE: The compound of Example 14 is known in the literature as Trimetrexate®, for use in treatments of certain kinds of cancers. [J. Med. Chem., 26, 1753–1760 (1983)]

Example 15

SYNTHESIS OF 2,4-DIAMINO-5-CHLORO-6-[(3,4,5-TRIMETHOXYPHENYLMETHYL)IMINO]QUINAZOLINE COMPOUND 91

Step A Synthesis of 2,4-diamino-5-chloro-6-nitroquinazoline as an intermediate

Nitric acid (90%), 125 mL, was stirred and cooled to −10° C., and 125 mL of 98% sulfuric acid was added dropwise. Upon completion of addition, the reaction mixture temperature was brought to 0° C., and 19.7 grams (0.10 mole) of 2,4-diamino-5-chloroquinazoline (Compound 2, prepared in a manner analogous to that of Step E of Example 1) was added. Upon completion of addition, the reaction mixture was allowed to warm to ambient temperature where it was stirred for about 18 hours. The reaction mixture was then poured into 1500 mL of ice. The resultant mixture was made basic with 700 mL of aqueous 30% ammonia, keeping the temperature below 30° C. The mixture was cooled in an ice-bath, and the resultant solid was collected by filtration. The solid was stirred with 1000 mL of tetrahydrofuran and 500 mL of water. The mixture was filtered to remove a solid. The filtrate was diluted with 500 mL of ethyl acetate and then was concentrated under reduced pressure to a solid residue. The two solids were combined, washed with ethyl acetate, and dried, yielding 22.2 grams of 2,4-diamino-5-chloro-6-nitroquinazoline. The NMR spectrum was consistent with the proposed structure.

Step B Synthesis of 2,4,6-triamino-5-chloroquinazoline (Compound 24) as an intermediate This compound was prepared in a manner analogous to that of Example 13, using 11.0 grams (0.049 mole) of 2,4-diamino-5-chloro-6-nitroquinazoline and 1.0 gram of 10% platinum on carbon in 70 mL of 2-methoxyethanol and 130 mL of ethanol, yielding 2,4,6-triamino-5-chloroquinazoline.

Step C Synthesis of 2,4-diamino-5-chloro-6-[(3,4,5-trimethoxyphenylmethyl)imino]quinazoline (Compound 91)

Under a nitrogen atmosphere, a stirred solution of 3.0 grams (0.014 mole) of 2,4,6-triamino-5-chloroquinazoline and 2.9 grams (0.029 mole) of 3,4,5-trimethoxybenzaldehyde in 30 mL of ethanol was heated at reflux during a 5 hour period. After this time, the resultant slurry was mixed with 50 mL of 2-ethoxyethanol, 70 mL of ethanol, and 2.0 grams (catalyst) of Raney nickel. The mixture was then hydrogenated at 50 psi of hydrogen during a 5 hour period using a Parr hydrogenator. The mixture was then filtered, and the filter cake was slurried with 50 mL of ethanol. The ethanol was decanted from the catalyst. The remaining solid and catalyst were slurried with an additional 50 mL of ethanol which was then decanted from the catalyst. The decantates were combined with 100 mL of dioxane and 2.0 grams of Raney nickel and hydrogenated during a four hour period, as described above: The reaction mixture was then diluted with 200 mL of dioxane and heated to reflux, at which time complete solution was obtained. The solution was filtered to remove the catalyst. The filtrate was concentrated under reduced pressure to a solid residue. The solid was recrystallized from dioxane and water, yielding 2.4 grams of solid platelets, mp 234°–235° C. The NMR spectrum indicated the solid to be 2,4-diamino-5-chloro-6-[(3,4,5-trimethoxyphenylmethyl)imino]quinazoline.

Example 16
SYNTHESIS OF 2,4-DIAMINO-5-METHYL-6-(3,5-DICHLOROPHENYL)QUINAZOLINE (COMPOUND 116)
Step A Synthesis of 3,5-dichlorophenylboronic acid as an intermediate This compound was prepared in a manner analogous to that of Step C of Example 2, using 20.0 grams (0.073 mole) of 3,5-dichlorophenyl iodide, 32.0 mL of n-butyllithium (0.080 mole–2.5M in hexanes) and 48.6 mL (0.220 mole) of triisopropyl borate. The yield of 3,5-dichlorophenyl-boronic acid was 6.7 grams; mp >250° C. The NMR spectrum was consistent with the proposed structure.

Step B Synthesis of 2-amino-6-methyl-5-(3,5-dichlorophenyl)benzonitrile as an intermediate This compound was prepared in a manner analogous to that of Step D of Example 2, using 4.3 grams (0.024 mole) of 3,5-dichlorophenylboronic acid, 4.8 grams (0.023 mole) of 2-amino-5-bromo-6-methylbenzonitrile, about 22 mL of aqueous 2M sodium carbonate, and about 0.15 gram (catalyst) of tetrakis(triphenylphosphine)palladium(0) in 50 mL of toluene. The yield of 2-amino-6-methyl-5-(3,5-dichlorophenyl)benzonitrile was 4.4 grams, mp 182° C. The NMR spectrum was consistent with the proposed structure.

Step C Synthesis of 2,4-diamino-5-methyl-6-(3,5-dichlorophenyl)quinazoline (Compound 116)

This compound was prepared in a manner analogous to that of Step E of Example 1, using 4.2 grams (0.015 mole) of 2-amino-6-methyl-5-(3,5-dichlorophenyl)benzonitrile and 2.0 grams (0.017 mole) of chloroformamidine hydrochloride in about 15 mL of 2-methoxyethyl ether. The yield of 2,4-diamino-5-methyl-6-(3,5-dichlorophenyl)quinazoline was 2.7 grams, mp >250° C. The NMR spectrum was consistent with the proposed structure.

Example 17
SYNTHESIS OF 2,4-DIAMINO-5-METHYL-6-[1-CHLORO-2-(4-TRIFLUOROMETHYLPHENYL)ETHENYL]QUINAZOLINE (COMPOUND 143)
Step A Synthesis of 2-amino-5-iodo-6-methylbenzonitrile as an intermediate This compound was prepared in a manner analogous to that of Step C of Example 1, using 17.5 grams (0.132 mole) of 2-amino-6-methylbenzonitrile (prepared as in Step B of Example 1) and 29.8 grams (0.132 mole) of N-iodosuccinimide in 325 mL of N,N-dimethylformamide. The yield of 2-amino-5-iodo-6-methylbenzonitrile was 28.5 grams. The NMR spectrum was consistent with the proposed structure.

Step B Synthesis of 2-amino-5-(trimethylsilylethynyl)-6-methylbenzonitrile as an intermediate This compound was prepared in a manner analogous to that of Step B of Example 6, using 10.0 grams (0.039 mole) of 2-amino-5-iodo-6-methylbenzonitrile, 8.3 mL (0.059 mole) of (trimethylsilyl)acetylene, 0.5 gram (catalyst) of bis(triphenylphosphine)palladium(ll) chloride, 0.2 gram (catalyst) of copper(I) iodide, and 21 mL (0.156 mole) of triethylamine in 75 mL of acetonitrile. The yield of 2-amino-5-(trimethylsilylethynyl)-6-methylbenzonitrile was 6.6 grams. The NMR spectrum was consistent with the proposed structure.

Step C Synthesis of 2-amino-5-ethynyl-6-methylbenzonitrile as an intermediate

A mixture of 1.4 grams (0.006 mole) of 2-amino-5-(trimethylsilylethynyl)-6-methylbenzonitrile and 0.9 gram (0.006 mole) of potassium carbonate in 50 mL of methanol was stirred at ambient temperature for one hour. The reaction mixture was then concentrated under reduced pressure to a residue. The residue was taken up in about 75 mL of water, and the solution was extracted with two 200 mL portions of diethyl ether. The combined extracts were dried with magnesium sulfate and filtered. The filtrate was concentrated under reduced pressure, yielding 1.0 gram of 2-amino-5-ethynyl-6-methylbenzonitrile. The NMR spectrum was consistent with the proposed structure. This reaction was repeated several times.

Step D Synthesis of 2-amino-6-methyl-5-[(4-trifluoromethylphenyl)ethynyl]benzonitrile as an intermediate A solution of 3.5 grams (0.022 mole) of 2-amino-5-ethynyl-6-methylbenzonitrile, 8.4 grams (0.031 mole) of 4-trifluoromethylphenyl iodide, 10.7 grams (0.077 mole) of triethylamine, 0.5 gram (catalyst) of bis(triphenylphosphine) palladium(II) chloride, and 0.5 gram (catalyst) of copper(l) iodide in 100 mL of acetonitrile was stirred at ambient temperature for about 18 hours. After this time the reaction mixture was concentrated under reduced pressure to a residue. The residue was partitioned between ethyl acetate and aqueous 1N hydrochloric acid. The two-layered mixture was filtered to remove a solid. The aqueous layer and the organic layer were separated, and the aqueous layer was washed with ethyl acetate. The ethyl acetate wash was combined with the organic layer, and the combination was washed with an aqueous solution of 10% lithium chloride. The organic layer was dried with magnesium sulfate and filtered. The filtrate was concentrated under reduced pressure to a residue. The residue was triturated with methylene chloride and filtered. The filtrate was subjected to column chromatography on silica gel. Elution was accomplished using methylene chloride. The product-containing fractions were combined and concentrated under reduced pressure, yielding 4.8 grams of 2-amino-6-methyl-5-[(4-trifluoromethylphenyl)

ethynyl]benzonitrile, mp 136°–138° C. The NMR spectrum was consistent with the proposed structure.

Step E Synthesis of 2,4-diamino-5-methyl-6-[1-chloro-2-(4-trifluoromethylphenyl)ethenyl]quinazoline (Compound 143)

This compound was prepared in a manner analogous to that of Step E of Example 1, using 2.7 grams (0.009 mole) of 2-amino-6-methyl-5-[(4-trifluoromethylphenyl)ethynyl]benzonitrile and 1.2 grams (0.011 mole) of chloroformamidine hydrochloride in 10 mL of 2-methoxyethyl ether. Upon completion of the reaction, the reaction mixture was diluted with 200 mL of diethyl ether. The resultant solid was collected by filtration, and was dissolved in a hot mixture of 300 mL of water and 100 mL of n-propanol. The solution was filtered hot through a sintered glass funnel to remove some insoluble material. The filtrate was then made basic with 100 mL of concentrated ammonium hydroxide. The resultant solid was collected by filtration, and dried at 60° C. under vacuum. The solid was then dissolved in a solution of 10% methanol in methylene chloride, and the solution was subjected to column chromatography on silica gel. Elution was accomplished using 10% methanol in methylene chloride. The product-containing fractions were combined and concentrated under reduced pressure, yielding 1.6 grams of 2,4-diamino-5-methyl-6-[1-chloro-2-(4-trifluoromethylphenyl)ethenyl]quinazoline, mp >300° C. The NMR spectrum was consistent with the proposed structure.

Example 18
SYNTHESIS OF 2,4-DIAMINO-5-METHYL-6-(5-CHLOROTHIEN-2-YL)QUINAZOLINE (COMPOUND 146)

Step A Synthesis of (5-chlorothien-2-yl)tributyl tin as an intermediate

A stirred solution of 5.1 mL (0.046 mole) of 2-bromo-5-chlorothiophene in 200 mL of tetrahydrofuran was cooled to -85°C., and 19.7 mL (0.049 mole) of n-butyllithium (0.049 mole–2.5M in hexanes) was added dropwise during a 15 minute period. The reaction mixture temperature was maintained at -85° C. to -80° C. throughout the addition. Upon completion of addition, the reaction mixture temperature was maintained at about -80° C. for one hour. After this time, a solution of 12.5 mL (0.046 mole) of tributyltin chloride in 50 mL of tetrahydrofuran was added to the cold reaction mixture during a 10 minute period. Upon completion of addition, the reaction mixture was stirred at -80° C. for one hour, then it was allowed to warm gradually to ambient temperature. The reaction was quenched with an aqueous solution saturated with ammonium chloride, and then the reaction mixture was extracted with three 150 mL portions of diethyl ether. The combined extracts were dried with magnesium sulfate and filtered. The filtrate was concentrated under reduced pressure, yielding 18.4 grams of (5-chlorothien-2-yl)tributyl tin. The NMR spectrum was consistent with the proposed structure.

Step B Synthesis of 2-amino-6-methyl-5-(5-chlorothien-2-yl)benzonitrile as an intermediate A solution of 5.9 grams (0.015 mole) of (5-chlorothien-2-yl)tributyl tin and 3.0 grams (0.015 mole) of 2-amino-5-iodo-6-methylbenzonitrile in 150 mL of toluene was stirred, and 0.2 gram (catalyst) of tetrakis(triphenylphosphine)palladium(0) was added. The reaction vessel was evacuated, and then back-filled with dry nitrogen gas. This process was repeated two more times. The reaction mixture was then heated to reflux where it was stirred for about 18 hours. After this time the reaction mixture was concentrated under reduced pressure to a residue. The residue was dissolved in methylene chloride, and the solution was filtered through a fiber-glass pad to remove the catalyst. The filtrate was subjected to column chromatography on silica gel. Elution was accomplished using methylene chloride. The product-containing fractions were combined and concentrated under reduced pressure, yielding 2.0 grams of 2-amino-6-methyl-5-(5-chlorothien-2-yl)benzonitrile, mp 108°–110° C. The NMR spectrum was consistent with the proposed structure.

Step C Synthesis of 2,4-diamino-5-methyl-6-(5-chlorothien-2-yl)quinazoline (Compound 146)

This compound was prepared in a manner analogous to that of Step E of Example 1, using 1.6 grams (0.007 mole) of 2-amino-6-methyl-5-(5-chlorothien-2-yl)benzonitrile and 0.8 gram (0.008 mole) of chloroformamidine hydrochloride in 10 mL of 2-methoxyethyl ether. The yield of 2,4-diamino-5-methyl-6-(5-chlorothien-2-yl)quinazoline was 1.1 grams, mp 270°–272° C., dec. The NMR spectrum was consistent with the proposed structure.

Example 19
SYNTHESIS OF 2,4-DIAMINO-5-METHYL-6-(4-TRIFLUOROMETHYLPHENYLCARBONYL)QUINAZOLINE (COMPOUND 158)

Step A Synthesis of 2-amino-5-(4-trifluoromethylphenylcarbonyl)-6-methylbenzonitrile as an intermediate A mixture of 2.6 grams (0.01 mole) of 2-amino-5-iodo-6-methylbenzonitrile (prepared in Step A of Example 17), 8.3 grams (0.0125 mole) of tetramethylammonium tetra(4-trifluoromethylphenyl)borate, and 0.1 gram (0.0005 mole) of palladium(II) acetate in 50 mL of N,N-dimethylformamide is placed in a high pressure reaction vessel. The stirring reaction mixture is then placed under 1 atmosphere of carbon monoxide gas, where it is maintained at about 60° C. for a 30 hour period. After this time, the cooled reaction mixture is removed from the reaction vessel and is filtered to remove catalyst and salts. The filtrate is concentrated under reduced pressure to a residue. The residue is partitioned between methylene chloride and water. The methylene chloride-product solution is then subjected to column chromatography on silica gel. Elution is accomplished with methylene chloride. The product-containing fractions are combined and concentrated under reduced pressure, yielding about 2.0 grams of 2-amino-5-(4-trifluoromethylphenylcarbonyl)-6-methylbenzonitrile.

Step B Synthesis of 2,4-diamino-5-methyl-6-(4-trifluorophenylcarbonyl)quinazoline (Compound 158)

This compound is prepared in a manner analogous to that of Step E of Example 1, using 2.0 grams (0.009 mole) of 2-amino-5-(4-trifluoromethylphenylcarbonyl)-6-methylbenzonitrile and 0.9 gram (0.009 mole) chloroformamidine hydrochloride in 20 mL of 2-methoxyethyl ether, yielding 2,4-diamino-5-methyl-6-(4-trifluorophenylcarbonyl)quinazoline.

Example 20
SYNTHESIS OF 2,4-DIAMINO-5-METHYL-6-(3-FLUORO-5-TRIFLUOROMETHYLPHENYL)QUINAZOLINE (COMPOUND 188)

Step A Synthesis of 3-fluoro-5-trifluoromethylphenylboronic acid as an intermediate A crystal of iodine and 0.5 gram (0.021 mole) of magnesium turnings were placed in a reaction vessel containing 10 mL of tetrahydrofuran. To this was added dropwise 2 mL of a solution of 5.0 grams (0.021 mole) of 3-fluoro-5-trifluoromethylphenyl bromide in 65 mL of tetrahydrofuran. The Grignard formation was initiated by warming the reaction vessel to about 45° C. The remaining 3-fluoro-5-trifluoromethylphenyl bromide—tetrahydrofuran solution was added portionwise at a rate which maintained gentle reflux of the reaction mixture.

In a second reaction vessel, 40 mL of tetrahydrofuran was cooled to −78° C., and 2.3 mL (0.021 mole) of trimethyl borate was added dropwise as the Grignard reagent of 3-fluoro-5-trifluoromethylphenyl bromide prepared above was transferred into the second reaction vessel using a cannula. The temperature of the reaction mixture was maintained below −60° C. during the additions. Upon completion of the additions, the reaction mixture was again cooled to −78° C., where it was stirred for about 45 minutes. After this time, the reaction mixture was allowed to warm to ambient temperature. The reaction mixture was then poured into about 200 mL of water and was made acidic with aqueous 5% hydrochloric acid. The mixture was extracted with four 100 mL portions of ethyl acetate. The combined extracts were dried with magnesium sulfate and filtered. The filtrate was concentrated under reduced pressure, yielding 3.3 grams of 3-fluoro-5-trifluoromethylphenylboronic acid, mp 167°–168° C. The NMR spectrum was consistent with the proposed structure.

Step B Synthesis of 2-amino-6-methyl-5-(3-fluoro-5-trifluoromethylphenyl)benzonitrile as an intermediate Under a dry nitrogen atmosphere, 0.5 gram (0.0004 mole) of tetrakis(triphenylphosphine)palladium(0) was added to a stirred mixture of 2.8 grams (0.0132 mole) of 2-amino-5-bromo-6-methylbenzonitrile (prepared as in Step C of Example 1), 35 mL of aqueous 2M sodium carbonate and 50 mL of toluene. To this was then added dropwise a solution of 3.3 grams (0.0159 mole) of 3-fluoro-5-trifluoromethylphenylboronic acid in 10 mL of ethanol. Upon completion of addition, the reaction mixture was warmed to about 80° C., where it was stirred for seven hours. After this time the reaction mixture was poured into 200 mL of water. The mixture was then extracted with four 100 mL portions of ethyl acetate. The combined extracts were dried with magnesium sulfate and filtered. The filtrate was concentrated under reduced pressure to a residue. The residue was subjected to column chromatography on silica gel. Elution was accomplished with methylene chloride. The product-containing fractions were combined and concentrated under reduced pressure, yielding 4.0 grams of 2-amino-6-methyl-5-(3-fluoro-5-trifluoromethylphenyl)benzonitrile, mp 96°–97° C. The NMR spectrum was consistent with the proposed structure.

Step C Synthesis of 2,4-diamino-5-methyl-6-(3-fluoro-5-trifluoromethylphenyl)quinazoline (Compound 188)

This compound was prepared in a manner analogous to that of Step E of Example 1, using 3.7 grams (0.013 mole) of 2-amino-6-methyl-5-(3-fluoro-5-trifluoromethylphenyl-benzonitrile and 1.7 grams (0.015 mole) of chloroformamidine hydrochloride in 25 mL of 2-methoxyethyl ether. The yield of 2,4-diamino-5-methyl-6-(3-fluoro-5-trifluoromethylphenyl)quinazoline was 2.8 grams, mp 225°–226° C. The NMR spectrum was consistent with the proposed structure.

Example 21
SYNTHESIS OF 2,4-DIAMINO-5-METHYL-6-[3-(4-FLUOROPHENYL)PHENYL]QUINAZOLINE (COMPOUND 196)
Step A Synthesis of 3-(4-fluorophenyl)phenyl bromide as an intermediate This compound was prepared in a manner analogous to that of Step D of Example 2, using 6.2 grams (0.044 mole) of 4-fluorophenylboronic acid (commercially available), 25.0 grams (0.100 mole) of 1,3-dibromobenzene, 0.2 gram (catalyst) of tetrakis(triphenylphosphine)palladium(0), 75 mL of aqueous 2M sodium carbonate, and 75 mL of toluene. The yield of 3-(4-fluorophenyl)phenyl bromide was 7.1 grams. The NMR spectrum was consistent with the proposed structure.

Step B Synthesis of 3-(4-fluorophenyl)phenylboronic acid as an intermediate

This compound was prepared in a manner analogous to that of Step C of Example 2, using 7.1 grams (0.028 mole) of 3-(4-fluorophenyl)phenyl bromide, 17 mL (0.034 mole) of n-butyllithium (2.0M in hexanes), and 9.5 mL (0.084 mole) of trimethyl borate in 100 mL of tetrahydrofuran. The yield of 3-(4-fluorophenyl)phenylboronic acid was about 3.5 grams. The NMR spectrum was consistent with the proposed structure.

Step C Synthesis of 2-amino-6-methyl-5-[3-(4-fluorophenyl)phenyl]benzonitrile as an intermediate This compound was prepared in a manner analogous to that of Step D of Example 2, using 3.4 grams (0.016 mole) of 3-(4-fluorophenyl)phenylboronic acid, 3.3 grams (0.016 mole) of 2-amino-5-bromo-6-methylbenzonitrile, 0.2 gram (catalyst) of tetrakis(triphenylphosphine)palladium(0), 50 mL of aqueous 2M sodium carbonate, and 50 mL of toluene. The yield of 2-amino-6-methyl-5-[3-(4-fluorophenyl) phenyl]benzonitrile was 4.8 grams. The NMR spectrum was consistent with the proposed structure.

Step D Synthesis of 2,4-diamino-5-methyl-6-[3-(4-fluorophenyl)phenyl]-quinazoline (Compound 196)

This compound was prepared in a manner analogous to that of Step E of Example 1, using 2.0 grams (0.007 mole) of 2-amino-6-methyl-5-[3-(4-fluorophenyl)phenyl] benzonitrile and 0.8 gram (0.007 mole) of chloroformamidine hydrochloride in 10 mL of 2-methoxyethyl ether. The yield of 2,4-diamino-5-methyl-6-[3-(4-fluorophenyl) phenyl]quinazoline was 0.5 gram. The NMR spectrum was consistent with the proposed structure.

Example 22
SYNTHESIS OF 2,4-DIAMINO-5-METHYL-6-[3-(4-CHLOROPHENOXY)PHENYL]QUINAZOLINE (COMPOUND 205)
Step A Synthesis of 3-(4-chlorophenoxy)phenyl bromide as an intermediate Under a nitrogen atmosphere, a solution of 13.6 grams (0.106 mole) of 4-chlorophenol in 50 mL of diglyme was stirred, and 24.1 mL (0.106 mole) of methanolic 25% sodium methoxide was added dropwise. Upon completion of addition, the reaction mixture was heated to about 165° C. to remove methanol. After the methanol was removed, the heating was ceased, and 25.0 grams (0.106 mole) of 1,3-dibromobenzene and 1.3 grams of cuprous bromide were added. Upon completion of the additions, the reaction mixture was heated to reflux where it was stirred for about 21 hours. The reaction mixture was then cooled and filtered. The filter cake was washed with diethyl ether, and the wash was combined with the filtrate. The combination was extracted with two 20 mL portions of aqueous 20% sodium hydroxide and then with two 75 mL portions of an aqueous solution saturated with sodium chloride. The organic layer was dried with magnesium sulfate and filtered.

The filtrate was concentrated under reduced pressure to a residual oil. The oil was distilled under vacuum, yielding about 9.0 grams of 3-(4-chlorophenoxy)phenyl bromide, bp 110° C./0.5 mm Hg. The NMR spectrum was consistent with the proposed structure.

Step B Synthesis of 3-(4-chlorophenoxy)phenylboronic acid as an intermediate

This compound was prepared in a manner analogous to that of Step C of Example 2, using 9.0 grams (0.032 mole)

of 3-(4-chlorophenoxy)phenyl bromide, 14 mL (0.035 mole) of n-butyllithium (2.5M in hexanes), and 10.4 mL (0.095 mole) of trimethyl borate in 100 mL of tetrahydrofuran. The yield of 3-(4-chlorophenoxy)phenylboronic acid was about 7.6 grams. The NMR spectrum was consistent with the proposed structure.

Step D Synthesis of 2-amino-6-methyl-5-[3-(4-chlorophenoxyphenyl]-benzonitrile as an intermediate This compound was prepared in a manner analogous to that of Step D of Example 2, using 7.6 grams (0.031 mole) of 3-(4-chlorophenoxy)phenylboronic acid, 6.5 grams (0.031 mole) of 2-amino-5-bromo-6-methylbenzonitrile, about 0.2 gram (catalyst) of tetrakis(triphenylphosphine)palladium(0), about 30 mL of aqueous 2M sodium carbonate, and about 50 mL of toluene. The yield of 2-amino-6-methyl-5-[3-(4-chlorophenoxy)phenyl]-benzonitrile was 2.0 grams. The NMR spectrum was consistent with the proposed structure.

Step E Synthesis of 2,4-diamino-5-methyl-6-[3-(4-chlorophenoxy)phenyl]-quinazoline (Compound 205)

This compound was prepared in a manner analogous to that of Step E of Example 1, using 1.8 grams (0.005 mole) of 2-amino-6-methyl-5-[3-(4-chlorophenoxy)phenyl] benzonitrile and 0.6 gram (0.005 mole) of chloroformamidine hydrochloride in about 10 mL of 2-methoxyethyl ether. The yield of 2,4-diamino-5-methyl-6-[3-(4-chlorophenoxy) phenyl]quinazoline was 0.9 gram. The NMR spectrum was consistent with the proposed structure.

Example 23
SYNTHESIS OF 2,4-DIAMINO-5-METHYL-6-(6-CHLORO-2,3-DIHYDRO-2,2-DIMETHYLBENZOFURAN-4-YL)QUINAZOLINE (COMPOUND 210)

Step A Synthesis of 2-methyl-3-(3-chloro-2-cyanophenoxy)-1-propene as an intermediate A solution of 30.0 grams (0.174 mole) of 2,6-dichlorobenzonitrile and 14.7 mL (0.174 mole) of 2-methyl-2-propen-1-ol in 200 mL of dimethyl sulfoxide was stirred, and 12.7 grams (0.191 mole) of 85% potassium hydroxide was added portionwise during a 5 minute period. During the addition, the reaction mixture temperature rose from 20° C. to about 35° C. Upon completion of the addition, the reaction mixture was stirred at ambient temperature for about 18 hours. After this time the reaction mixture was poured into 600 mL of water. The mixture was filtered to collect a solid. The solid was washed with water and dried under vacuum, yielding 33.9 grams of 2-methyl-3-(3-chloro-2-cyanophenoxy)-1-propene. The NMR spectrum was consistent with the proposed structure.

Step B Synthesis of 6-chloro-7-cyano-2,3-dihydro-2,2-dimethylbenzofuran as an intermediate A stirred mixture of 33.9 grams (0.163 mole) of 2-methyl-3-(3-chloro-2-cyanophenoxy)-1-propene and 0.2 gram (0.0017 mole) of magnesium chloride was warmed to 180° C. during a one hour period, where it was stirred for about six hours. The product, which sublimed to the top of the reaction vessel, was subjected to column chromatography on silica gel. Elution was accomplished using 1:1 methylene chloride and petroleum ether. The product-containing fractions were combined and concentrated under reduced pressure, yielding 25.8 grams of 6-chloro-7-cyano-2,3-dihydro-2,2-dimethylbenzofuran. The NMR spectrum was consistent with the proposed structure.

Step C Synthesis of 7-aminocarbonyl-6-chloro-2,3-dihydro-2,2-dimethylbenzofuran as an intermediate A stirred solution of 10.0 grams (0.048 mole) of 6-chloro-7-cyano-2,3-dihydro-2,2-dimethylbenzofuran in 200 mL of 2-methyl-2-propanol was warmed to reflux, and 9.5 grams (0.17 mole) of 85% potassium hydroxide was added in one portion. Upon completion of addition, the reaction mixture was heated at reflux for about 75 minutes. The reaction mixture was then cooled and poured into 400 mL of water that was cooled in an ice bath. The resultant solid was collected by filtration and dried under vacuum, yielding 8.2 grams of 7-aminocarbonyl-6-chloro-2,3-dihydro-2,2-dimethylbenzofuran. The NMR spectrum was consistent with the proposed structure.

Step D Synthesis of 7-amino-6-chloro-2,3-dihydro-2,2-dimethylbenzofuran as an intermediate A stirred solution of 5.8 grams (0.145 mole) of sodium hydroxide in 100 mL of water was cooled to 0° C., and 7.3 grams (0.045 mole) of bromine was added dropwise during a 5 minute period. Upon completion of addition, the mixture was stirred for 5 minutes, and an emulsion of 8.2 grams (0.036 mole) of 7-aminocarbonyl-6-chloro-2,3-dihydro-2,2-dimethylbenzofuran in 75 mL of dioxane was added portionwise during a 15 minute period. Upon completion of addition, the reaction mixture was stirred at 0° C. for one hour. The reaction mixture was warmed to 75° C. during a two hour period, where it was stirred for 19 hours. After this time the reaction mixture was cooled and poured into 300 mL of water. The mixture was then extracted with two 200 mL portions of ethyl acetate. The combined extracts were washed with an aqueous solution saturated with sodium chloride and dried with magnesium sulfate. The mixture was filtered and concentrated under reduced pressure to a residue. The residue was subjected to column chromatography on silica gel. Elution was accomplished using methylene chloride. The product containing fractions were combined and concentrated under reduced pressure, yielding 4.5 grams of 7-amino-6-chloro-2,3-dihydro-2,2-dimethylbenzofuran. The NMR spectrum was consistent with the proposed structure.

Step E Synthesis of 7-amino-4-bromo-6-chloro-2,3-dihydro-2,2-dimethylbenzofuran as an intermediate This compound was prepared in a manner analogous to that of Step C of Example 1, using 4.5 grams (0.023 mole) of 7-amino-6-chloro-2,3-dihydro-2,2-dimethylbenzofuran and 4.1 grams (0.023 mole) of N-bromosuccinimide in 50 mL of N,N-dimethylformamide. The yield of 7-amino-4-bromo-6-chloro-2,3-dihydro-2,2-dimethylbenzofuran was 5.1 grams. The NMR spectrum was consistent with the proposed structure.

Step F Synthesis of 4-bromo-6-chloro-2,3-dihydro-2,2-dimethylbenzofuran as an intermediate A stirred solution of 5.1 grams (0.018 mole) of 7-amino-4-bromo-6-chloro-2,3-dihydro-2,2-dimethylbenzofuran and 25 mL of toluene in 100 mL of ethanol was cooled in an ice bath, and 2 mL (0.036 mole) of concentrated sulfuric acid was added slowly. Upon completion of addition, 2.0 grams (0.029 mole) of sodium nitrite was then added. The ice bath was then removed, and the reaction mixture was warmed to 75° C., where it stirred for minutes. After this time the reaction mixture was warmed to 95° C., where it stirred for one hour. The reaction mixture was then cooled and poured into 200 mL of water. The mixture was extracted with two 150 mL portions of diethyl ether. The combined extracts were dried with magnesium sulfate and filtered. The filtrate was concentrated under reduced pressure to a residue. The residue was subjected to column chromatography on silica gel. Elution was accomplished using petroleum ether. The product-containing fractions were combined and concentrated under reduced pressure, yielding 3.6 grams of 4-bromo-6-chloro-2,3-dihydro-2,2-dimethylbenzofuran. The NMR spectrum was consistent with the proposed structure.

Step G Synthesis of 6-chloro-2,3-dihydro-2,2-dimethylbenzofuran-4-ylboronic acid as an intermediate This compound was prepared in a manner analogous to that of Step C of Example 2, using 3.6 grams (0.014 mole) of 4-bromo-6-chloro-2,3-dihydro-2,2-dimethylbenzofuran, 5.5 mL (0.014 mole) of n-butyllithium (2.5M in hexanes), and 4.7 mL (0.042 mole) of trimethyl borate in 75 mL of tetrahydrofuran. The yield of 6-chloro-2,3-dihydro-2,2-dimethylbenzofuran-4-ylboronic acid was 3.0 grams. The NMR spectrum was consistent with the proposed structure.

Step H Synthesis of 2-amino-6-methyl-5-(6-chloro-2,3-dihydro-2,2-dimethylbenzofuran-4-yl)benzonitrile as an intermediate This compound was prepared in a manner analogous to that of Step D of Example 2, using 3.0 grams (0.013 mole) of 6-chloro-2,3-dihydro-2,2-dimethylbenzofuran-4-yl-boronic acid, 2.1 grams (0.031 mole) of 2-amino-5-iodo-6-methylbenzonitrile (prepared as in Step A of Example 17), 0.12 gram (catalyst) of tetrakis(triphenylphosphine) palladium(0), 10 mL of aqueous 2M sodium carbonate, and 100 mL of toluene. The yield of 2-amino-6-methyl-5-(6-chloro-2,3-dihydro-2,2-dimethylbenzofuran-4-yl) benzonitrile was 1.9 grams. The NMR spectrum was consistent with the proposed structure.

Step I Synthesis of 2,4-diamino-5-methyl-6-(6-chloro-2,3-dihydro-2,2-dimethylbenzofuran-4-yl)quinazoline (Compound 210)

This compound was prepared in a manner analogous to that of Step E of Example 1, using 1.7 grams (0.005 mole) of 2-amino-6-methyl-5-(6-chloro-2,3-dihydro-2,2-dimethylbenzofuran-4-yl)benzonitrile and 0.8 gram (0.006 mole) of chloroformamidine hydrochloride in 15 mL of 2-methoxyethyl ether. The yield of 2,4-diamino-5-methyl-6-(6-chloro-2,3-dihydro-2,2-dimethylbenzofuran-4-yl) quinazoline was 1.2 grams. The NMR spectrum was consistent with the proposed structure.

Example 24
SYNTHESIS OF 2,4-DIAMINO-7-FLUORO-5-METHYL-6-[3,5-DI(TRIFLUOROMETHYL)PHENYL] QUINAZOLINE (COMPOUND 214)

Step A Synthesis of 5-fluoro-2-methylcarbonylamino-3-methylnitrobenzene as an intermediate Stirred acetic anhydride, 300 mL, was cooled to about 70° C., and 25.1 grams (0.20 mole) of 4-fluoro-2-methylaniline was added dropwise during a 30 minute period. Upon completion of addition, the reaction mixture was stirred at about 10° C. for an additional 15 minutes. In a separate reaction vessel, acetyl nitrate was prepared by the dropwise addition of 14.9 mL of 90% nitric acid to 30 mL of stirred, cold (0°–15° C.) acetic anhydride during a 15 minute period. The so-prepared acetyl nitrate was cooled to about −5° C., placed in a dropping funnel, and added dropwise during a 30 minute period to the 2-methylaniline solution. Upon completion of addition, the reaction mixture was stirred an additional 5 hours. After this time the reaction mixture was poured into 400 grams of ice. The resultant solid was collected by filtration, washed with water, and dried at 60° C. under vacuum, yielding 23.0 grams of 5-fluoro-2-methylcarbonylamino-3-methylnitrobenzene, mp 167°–172° C. The NMR spectrum was consistent with the proposed structure.

Step B Synthesis of 4-fluoro-2-nitro-6-methylaniline as an intermediate

A stirred solution of 22.4 grams (0.106 mole) of 5-fluoro-2-methylcarbonylamino-3-methyinitrobenzene, 100 mL of concentrated hydrochloric acid, and 100 mL of ethanol was heated at reflux for about 17 hours. The reaction mixture was cooled and poured into 500 grams of ice. The mixture was made basic with aqueous 50% sodium hydroxide. The resultant solid was collected by filtration and was thoroughly washed with water. The solid was dried at about 60° C. under vacuum, yielding 17.0 grams of 4-fluoro-2-nitro-6-methylaniline, mp 111°–113°C. The NMR spectrum was consistent with the proposed structure. The reaction was repeated to obtain more product.

Step C Synthesis of 4-fluoro-2-nitro-6-methylphenyl iodide as an intermediate

A mixture of 4.4 grams (0.026 mole) of 4-fluoro-2-nitro-6-methylaniline, 13.2 grams (0.052 mole) of iodine, and 5.5 grams (0.029 mole) of copper(I) iodide in 125 mL of acetonitrile was stirred, and a solution of 4.6 mL (0.039 mole) of tert-butyl nitrite in 25 mL of acetonitrile was added dropwise during a 10 minute period. Upon completion of addition, the reaction mixture was stirred at ambient temperature for about 16 hours. After this time the reaction mixture was poured into 300 mL of water. Excess iodine was destroyed using sodium meta-bisulfite. The mixture was then extracted with two 250 mL portions of diethyl ether. The combined extracts were dried with magnesium sulfate and filtered. The filtrate was concentrated under reduced pressure to a residue. The residue was subjected to column chromatography on silica gel. Elution was accomplished using 1:3 methylene chloride:petroleum ether. The product-containing fractions were combined and concentrated under reduced pressure, yielding 3.4 grams of 4-fluoro-2-nitro-6-methylphenyl iodide. The NMR spectrum was consistent with the proposed structure. The reaction was repeated to obtain more product.

Step D Synthesis of 4-fluoro-2-nitro-6-methylbenzonitrile as an intermediate

A stirred mixture of 19.0 grams (0.068 mole) of 4-fluoro-2-nitro-6-methylphenyl iodide and 7.0 grams (0.078 mole) of copper(I) cyanide in 100 mL of N,N-dimethylformamide was heated at 150°–155° C. for 30 minutes. The reaction mixture was then diluted with 400 mL of water and 100 mL of ethyl acetate. The mixture was filtered, and the filtrate was placed in a separatory funnel. The organic layer was separated, and the aqueous layer was washed with 200 mL of ethyl acetate. The combined wash and organic layer was then washed with three 150 mL portions of aqueous 5% lithium chloride. The mixture was dried with magnesium sulfate and filtered. The filtrate was concentrated under reduced pressure to a residue. The residue was subjected to column chromatography on silica gel. Elution was accomplished using 1:1 methylene chloride: petroleum ether. The product-containing fractions were combined and concentrated under reduced pressure, yielding 12.8 grams of 4-fluoro-2-nitro-6-methylbenzonitrile, mp 61°–63° C. The NMR spectrum was consistent with the proposed structure.

Step E Synthesis of 2-amino-4-fluoro-6-methylbenzonitrile as an intermediate

This compound was prepared in a manner analogous to that of Step B of Example 1, using 12.5 grams (0.069 mole) of 4-fluoro-2-nitro-6-methylbenzonitrile, 25.4 mL (0.251 mole) of cyclohexene, 1.9 grams (catalyst) of 10% palladium on charcoal, and 10 mL of water in 200 mL of ethanol. The yield of 2-amino-4-fluoro-6-methylbenzonitrile was 2.0 grams. The NMR spectrum was consistent with the proposed structure.

Step F Synthesis of 2-amino-5-bromo-4-fluoro-6-methylbenzonitrile as an intermediate This compound was prepared in a manner analogous to that of Step C of Example 1, using 0.5 gram (0.003 mole) of 2-amino-4-fluoro-6-methylbenzonitrile and 0.6 gram (0.004 mole) of N-bromosuccinimide in 30 mL of N,N-dimethylformamide. The yield of 2-amino-5-bromo-4-fluoro-6-methylbenzonitrile was 0.7 gram. The NMR spectrum was consistent with the proposed structure.

Step G Synthesis of 2-amino-4-fluoro-6-methyl-5-[3,5-di(trifluoromethyl)phenyl]benzonitrile as an intermediate This compound was prepared in a manner analogous to that of Step D of Example 2, using 1.3 grams (0.005 mole) of 3,5-di(trifluoromethyl)phenylboronic acid, (commercially available) 0.7 gram (0.003 mole) of 2-amino-5-bromo-4-fluoro-6-methylbenzonitrile, 0.2 gram (catalyst) of tetrakis(triphenylphosphine)palladium(0), 4.7 mL (0.009 mole) of aqueous 2M sodium carbonate, and 50 mL of toluene. The yield of 2-amino-4-fluoro-6-methyl-5-[3,5-di(trifluoromethyl)phenyl]benzonitrile was 0.9 gram. The NMR spectrum was consistent with the proposed structure.

Step H Synthesis of 2,4-diamino-7-fluoro-5-methyl-6-[3,5-di(trifluoromethyl)phenyl]quinazoline (Compound 214)

This compound was prepared in a manner analogous to that of Step E of Example 1, using 0.9 gram (0.002 mole) of 2-amino-4-fluoro-6-methyl-5-[3,5-di(trifluoromethyl)phenyl]benzonitrile and 0.3 gram (0.003 mole) of chloroformamidine hydrochloride in 6 mL of 2-methoxyethyl ether. The yield of 2,4-diamino-7-fluoro-5-methyl-6-[3,5-di(trifluoromethyl)phenyl]quinazoline was 0.4 grams, mp 224°–225° C. The NMR spectrum was consistent with the proposed structure.

Example 25
SYNTHESIS OF 2,4-DI[(1,1-DIMETHYLETHOXY) CARBONYLAMINO]-5-METHYL-6-[3,5-DI(TRIFLUOROMETHYL)PHENYL]QUINAZOLINE (COMPOUND 217)

A stirred mixture of 2.00 grams (0.0050 mole) of 2,4-diamino-5-methyl-6-[3,5-di(trifluoromethyl)phenyl]quinazoline (Compound 63), 0.06 gram (0.0005 mole) of dimethylaminopyridine, and 10.00 grams (0.0458 mole) of di-tert-butyl dicarbonate was heated at 75° C. for about 6 hours. The reaction mixture was cooled and dissolved in ethyl acetate. The solution was passed through a column of silica gel. Elution was accomplished using ethyl acetate. The eluate was concentrated under reduced pressure to a residue. The residue was triturated with hexane to remove unreacted di-tert-butyl dicarbonate. The yield of 2,4-di[(1,1-dimethylethoxy)carbonylamino]-5-methyl-6-[3,5-di(trifluoromethyl)phenyl]quinazoline was 1.2 grams. The NMR spectrum was consistent with the proposed structure.

Example 26
SYNTHESIS OF 2,4-DIAMINO-5-(1-METHYLETHYL)-6-[3,5-35 DI(TRIFLUOROMETHYL)PHENYL]QUINAZOLINE (COMPOUND 219)

Step A Synthesis of 2-methylcarbonylamino-3-(1-methylethyl)-nitrobenzene as an intermediate This compound was prepared in a manner analogous to that of Step A of Example 24, using 19.1 grams (0.141 mole) of 2-(1-methylethyl)aniline and 7.9 mL (0.169 mole) of 90% nitric acid in about 85 mL of acetic anhydride. The yield of 2-methylcarbonylamino-3-(1-methylethyl)nitrobenzene was 30.0 grams. The NMR spectrum was consistent with the proposed structure.

Step B Synthesis of 2-nitro-6-(1-methylethyl)aniline as an intermediate

This compound was prepared in a manner analogous to that of Step B of Example 24, using 30.0 grams (0.135 mole) of 2-methylcarbonylamino-3-(1-methylethyl)nitrobenzene, 50 mL of concentrated hydrochloric acid, and 50 mL of ethanol. The yield of 2-nitro-6-(1-methylethyl)aniline was 12.8 grams. The NMR spectrum was consistent with the proposed structure.

Step C Synthesis of 2-nitro-6-(1-methylethyl)phenyl iodide as an intermediate

This compound was prepared in a manner analogous to that of Step C of Example 24, using 10.7 grams (0.059 mole) 2-nitro-6-(1-methylethyl)aniline, 10.5 mL (0.089 mole) of tert-butyl nitrite, and 15.0 grams (0.059 mole) of iodine in 250 mL of acetonitrile. The yield of 2-nitro-6-(1-methylethyl)phenyl iodide was 15.2 grams. The NMR spectrum was consistent with the proposed structure.

Step D Synthesis of 2-nitro-6-(1-methylethyl)benzonitrile as an intermediate

This compound was prepared in a manner analogous to that of Step D of Example 24, using 15.0 grams (0.052 mole) of 2-nitro-6-(1-methylethyl)phenyl iodide and 5.4 mL (0.060 mole) of copper(l) cyanide in 75 mL of N,N-dimethylformamide. The yield of 2-nitro-6-(1-methylethyl)benzonitrile was 9.3 grams. The NMR spectrum was consistent with the proposed structure.

Step E Synthesis of 2-amino-6-(1-methylethyl)benzonitrile as an intermediate

This compound was prepared in a manner analogous to that of Step B of Example 1, using 9.3 grams (0.049 mole) of 2-nitro-6-(1-methylethyl)benzonitrile 18.0 mL (0.178 mole) of cyclohexene, 2.0 grams (catalyst) of 10% palladium on charcoal, and 10 mL of water in 250 mL of ethanol. The yield of 2-amino-6-(1-methylethyl)benzonitrile was 7.4 grams. The NMR spectrum was consistent with the proposed structure.

Step F Synthesis of 2-amino-5-bromo-6-(1-methylethyl)benzonitrile as an intermediate This compound was prepared in a manner analogous to that of Step C of Example 1, using 7.0 grams (0.044 mole) of 2-amino-6-(1-methylethyl)benzonitrile and 7.8 grams (0.044 mole) of N-bromosuccinimide in 150 mL of N,N-dimethylformamide. The yield of 2-amino-5-bromo-6-(1-methylethyl)benzonitrile was 8.4 grams, mp 82°–85° C. The NMR spectrum was consistent with the proposed structure.

Step G Synthesis of 2-amino-6-(1-methylethyl)-5-[3,5-di(trifluoromethyl)phenyl]benzonitrile as an intermediate This compound was prepared in a manner analogous to that of Step D of Example 2, using 3.1 grams (0.011 mole) of 3,5-di(trifluoromethyl)phenylboronic acid, 1.8 grams (0.008 mole) of 2-amino-5-bromo-6-(1-methylethyl)benzonitrile, 0.3 gram (catalyst) of tetrakis(triphenylphosphine)palladium(0), 12.0 mL (0.024 mole) of aqueous 2M sodium carbonate, and 200 mL of toluene. The yield of 2-amino-6-(1-methylethyl)-5-[3,5-di-(trifluoromethyl)phenyl]benzonitrile was 2.2 grams. The NMR spectrum was consistent with the proposed structure.

Step H Synthesis of 2,4-diamino-5-(1-methylethyl)-6-[3,5-di(trifluoromethyl)phenyl]quinazoline (Compound 219)

This compound was prepared in a manner analogous to that of Step E of Example 1, using 1.9 grams (0.005 mole) of 2-amino-6-(1-methylethyl)-5-[3,5-di(trifluoromethyl)phenyl]benzonitrile and 0.7 gram (0.006 mole) of chloroformamidine hydrochloride in 25 mL of 2-methoxyethyl ether. The yield of 2,4-diamino-5-(1-methylethyl)-6-[3,5-di(trifluoromethyl)phenyl]quinazoline was 0.4 grams, mp 212°–214° C. The NMR spectrum was consistent with the proposed structure.

Example 27

SYNTHESIS OF 2,4-DIAMINO-5-METHYL-6-(2,3-DIHYDRO-2,2-DIMETHYL-3-BENZOFURANON-4-YL)QUINAZOLINE (COMPOUND 212)

Step A Synthesis of 7-amino-4-bromo-2,3-dihydro-2,2-dimethylbenzofuran as an intermediate A stirred solution of 10.0 grams (0.061 mole) of 7-amino-2,3-dihydro-2,2-dimethylbenzofuran in 150 mL of N,N-dimethylformamide was cooled in an ice-water bath, and a solution of 10.9 grams (0.061 mole) of N-bromosuccinimide in 50 mL of N,N-dimethylformamide was added in one portion. Upon completion of addition, the reaction mixture was maintained in the ice-water bath for about one hour. After this time the reaction mixture was poured into about 600 mL of water. The mixture was then extracted with two 200 mL portions of diethyl ether. The combined extracts were washed with two 100 mL portions of an aqueous 10% lithium chloride solution. The organic layer was dried with magnesium sulfate and filtered. The filtrate was concentrated under reduced pressure, yielding 12.3 grams of 7-amino-4-bromo-2,3-dihydro-2,2-dimethylbenzofuran. The NMR spectrum was consistent with the proposed structure.

Step B Synthesis of 4-bromo-2,3-dihydro-2,2-dimethylbenzofuran as an intermediate A stirred solution of 12.3 grams (0.051 mole) of 7-amino-4-bromo-2,3-dihydro-2,2-dimethylbenzofuran and 30 mL of toluene in 200 mL of ethanol was cooled in an ice-bath, and 5.6 mL (0.102 mole) of concentrated sulfuric acid was added slowly, followed by 5.6 grams (0.082 mole) of sodium nitrite. Upon completion of addition, the ice-bath was removed, and the reaction mixture was warmed to 50° C. The reaction mixture temperature was then brought to about 75° C., where it was stirred for 30 minutes. After this time the reaction mixture was heated at reflux for one hour and then was poured into 200 mL of water. The mixture was extracted with two 150 mL portions of diethyl ether. The combined extracts were dried with magnesium sulfate and filtered. The filtrate was concentrated under reduced pressure to a residual oil. The oil was subjected to column chromatography on silica gel. Elution was accomplished using petroleum ether. The product-containing fractions were combined and concentrated under reduced pressure, yielding 3.6 grams of 4-bromo-2,3-dihydro-2,2-dimethylbenzofuran. The NMR spectrum was consistent with the proposed structure.

Step C Synthesis of 4-bromo-2,3-dihydro-2,2-dimethyl-3-benzofuranone as an intermediate Under a nitrogen atmosphere, a stirred solution of 3.0 grams (0.013 mole) 4-bromo-2,3-dihydro-2,2-dimethylbenzofuran, 10.7 grams (0.039 mole) of potassium persulfate, and 3.3 grams (0.013 mole) of copper(II) sulfate pentahydrate in 30 mL of water and 30 mL of acetonitrile was heated at reflux for one hour. After this time the reaction mixture was poured into 200 mL of water. The mixture was then extracted with one 200 mL portion of diethyl ether. The extract was dried with magnesium sulfate and filtered. The filtrate was concentrated under reduced pressure to a residual oil. The oil was subjected to column chromatography on silica gel. Elution was accomplished using 1:1 petroleum ether and methylene chloride. The product-containing fractions were combined and concentrated under reduced pressure, yielding 2.1 grams of 4-bromo-2,3-dihydro-2,2-dimethyl-3-benzofuranone. The NMR spectrum was consistent with the proposed structure. Steps A through C were repeated.

Step D Synthesis of 2,4-diamino-5-methylquinazoline (compound 27) as an intermediate This compound was prepared in a manner analogous to that of Step E of Example 1, using 1 0.0 grams (0.076 mole) of 2-amino-6-methylbenzonitrile (prepared as in Example 1, Step B), and 10.0 grams (0.087 mole) of chloroformamidine hydrochloride in 40 mL of 2-methoxyethyl ether, yielding 11.5 grams of 2,4-diamino-5-methylquinazoline. The NMR spectrum was consistent with the proposed structure.

Step E Synthesis of 2,4-diamino-6-acetoxymercurio-5-methylquinazoline as an intermediate A solution of 10.0 grams (0.057 mole) of 2,4-diamino-5-methylquinazoline and 18.2 grams (0.057 mole) of mercuric acetate in 125 mL of acetic acid is stirred at ambient temperature for about 18 hours. After this time the reaction mixture is poured into 1000 mL of water. The resultant precipitate is collected by filtration and dried, yielding 2,4-diamino-6-acetoxymercurio-5-methylquinazoline.

Step F Synthesis of (2,4-diamino-5-methylquinazolin-6-yl)boronic acid as an intermediate A solution of 17.3 grams (0.040 mole) of 2,4-diamino-6-acetoxymercurio-5-methylquinazoline and 38.3 mL (0.400 mole) of boranetetrahydrofuran complex (1.0M in tetrahydrofuran). in 1000 mL of tetrahydrofuran is stirred at ambient temperature for about 30 minutes. The reaction mixture is then poured into water. The resultant precipitate is collected by filtration and dried, yielding (2,4-diamino-5-methylquinazolin-6-yl)boronic acid.

NOTE: The method of S.W. Breuer and F.G. Thorpe (Tetrahedron Lett.No. 42, pp 3719–3720, 1974) is used to prepare 2,4-diamino-5-methylquinazolin-6-yl)boronic acid from its 6-acetoxymercurio derivative.

Step G Synthesis of 2,4-diamino-5-methyl-6-(2,3-dihydro-2,2-dimethyl-3-benzofuranon-4-yl)quinazoline (Compound 212)

A solution of 2.1 grams (0.010 mole) of (2,4-diamino-5-methylquinazolin-6-yl)boronic acid in 25 mL of N,N-dimethylformamide is stirred, and 2.1 grams (0.009 mole) of 4-bromo-2,3-dihydro-2,2-dimethyl-3-benzofuranone (prepared in Step C of this Example), 2.8 grams (0.020 mole) of potassium carbonate, and 0.31 gram (catalyst-3 mole %) of tetrakis(triphenylphosphine)palladium(0) are added. The reaction mixture is then warmed to 90° C., where it is stirred for about 16 hours. After this time the reaction mixture is poured into water. The resultant precipitate is collected by filtration and dried, yielding 2,4-diamino-5-methyl-6-(2,3-dihydro-2,2-dimethyl-3-benzofuranon-4-yl)quinazoline.

NOTE: The methods of A. Suzuki et al. (J. Am. Chem. Soc. 1989, 111, 314–321) and W. C. Shieh et al. (J. Org. Chem. 1992, 57, 379–381) are used to prepare 2,4-diamino-5-methyl-6-(2,3-dihydro-2,2-dimethyl-3-benzofuranon-4-yl)quinazoline.

Example 28

SYNTHESIS OF 2,4-DI(DIMETHYLAMINO-METHYLENEAMINO)-5-METHYL-6-[3,5-DI(TRIFLUOROMETHYL)PHENYL]QUINAZOLINE (COMPOUND 272)

Under a nitrogen atmosphere, a stirred solution of 1.0 gram (0.0026 mole) of 2,4-diamino-5-methyl-6-[3,5-di(trifluoromethyl)phenyl]quinazoline (Compound 63-prepared as in Example 1) in 20 mL of dimethylformamide dimethyl acetal was heated at 80° C. for about 18 hours. After this time, the reaction mixture was cooled and concentrated under reduced pressure to a residue. The residue was then triturated with petroleum ether, and the resulting solid was collected by filtration. The filter cake was washed with petroleum ether and dried, yielding about 1.1. grams of 2,4-di(dimethylaminomethyleneamino)-5-methyl-6-[3,5-di(trifluoromethyl)phenyl]quinazoline, mp 208°–210° C. The NMR spectrum was consistent with the proposed structure.

Example 29
SYNTHESIS OF 2,4-DIAMINO-6-(4-CHLOROPHENOXY)QUINAZOLINE (COMPOUND 242)
Step A Synthesis of 2-nitro-5-(4-chlorophenoxy) benzonitrile as an intermediate Sodium hydride (60% in mineral oil), 1.5 grams (0.038 mole) was washed in petroleum ether. The petroleum ether was decanted, and the sodium hydride was suspended in about 20 mL of N,N-dimethylformamide. The suspension was stirred, and solutions of 4.5 grams (0.035 mole) of 4-chlorophenol in 20 mL of N,N-dimethylformamide and 5.0 grams (0.027 mole) of 5-chloro-2-nitrobenzonitrile in 20 mL of N,N-dimethylformamide were added, respectively. Upon completion of addition, the reaction mixture was warmed to reflux where it stirred for about 18 hours. The reaction mixture was then cooled and poured into a mixture of 500 mL of water and 50 mL of aqueous 2N sodium hydroxide. The mixture was stirred for about 15 minutes, then it was allowed to stand for about 18 hours. The resultant solid was collected by filtration and recrystallized from ethanol, yielding 3.9 grams of 2-nitro-5-(4-chlorophenoxy) benzonitrile, mp 120°–122° C. The NMR spectrum was consistent with the proposed structure.

Step B Synthesis of 2-amino-5-(4-chlorophenoxy) benzonitrile as an intermediate

A mixture of 2.0 grams (0.035 mole) of iron powder, 1.0 mL of concentrated hydrochloric acid, 4.0 mL of water, in 30 mL of ethanol was stirred, and 2.5 grams (0.009 mole) of 2-nitro-5-(4-chlorophenoxy)benzonitrile was added slowly. Upon completion of addition, the reacton mixture was warmed to reflux where it stirred for about seven hours. After this time, the reaction mixture was allowed to cool to ambient temperature where it stirred for about 18 hours. The reaction mixture was then warmed and filtered through a pad of diatomaceous earth. The filtrate was concentrated under reduced pressure to a residue. The residue was purified with column chromatography on silica gel, using 1:1 petroleum ether/methylene chloride. The product-containing fractions were combined and concentrated under reduced pressure, yielding 0.2 gram of 2-amino-5-(4-chlorophenoxy) benzonitrile, mp 116°–118° C. The NMR spectrum was consistent with the proposed structure. The reaction was repeated.

Step C Synthesis of 2,4-diamino-6-(4-chlorophenoxy) quinazoline (Compound 242)

This compound was prepared in a manner analogous to that of Step E of Example 1, using 0.5 gram (0.002 mole) of 2-amino-5-(4-chlorophenoxy)benzonitrile and 0.3 gram (0.003 mole) of chloroformamidine hydrochloride in 5 mL of 2-methoxyethyl ether. The yield of 2,4-diamino-6-(4-chlorophenoxy)quinazoline was 0.5 gram, mp 226°–228° C. The NMR spectrum was consistent with the proposed structure.

Example 30
SYNTHESIS OF 2,4-DIAMINO-6-(2,3-DIHYDRO-2,2,6-TRIMETHYLBENZOFURAN-4-YL)-5-METHYLQUINAZOLINE (COMPOUND 225)
Step A Synthesis of 2-methyl-3-(3-methyl-2-nitrophenoxy)-1-propene as an intermediate A mixture of 20.0 grams (0.130 mole) of 3-methyl-2-nitrophenol and 22.5 grams (0.163 mole) of potassium carbonate in 200 mL of dimethyl sulfoxide was stirred, and 15.3 mL (0.156 mole) of methallyl chloride was added dropwise during a five minute period. Upon completion of addition, 5.4 grams (0.033 mole) of potassium iodide was added in one portion. The reaction mixture was then stirred at ambient temperature for about 18 hours. After this time the reaction mixture was poured into 500 mL of water. The mixture was then extracted with two 200 mL portions of diethyl ether. The combined extracts were dried with magnesium sulfate and filtered. The filtrate was concentrated under reduced pressure, yielding 27.0 grams of 2-methyl-3-(3-methyl-2-nitrophenoxy)-1-propene. The NMR spectrum was consistent with the proposed structure.

Step B Synthesis of 2,3-dihydro-2,2,6-trimethyl-7-nitrobenzofuran as an intermediate A stirred mixture of 26.5 grams (0.128 mole) of 2-methyl-3-(3-methyl-2-nitrophenoxy)-1-propene and 0.4 gram (0.004 mole) of magnesium chloride was warmed to 180° C. during one hour, where it was maintained for four additional hours. The reaction mixture was cooled, yielding 26.5 grams of 2,3-dihydro-2,2,6-trimethyl-7-nitrobenzofuran. The NMR spectrum was consistent with the proposed structure.

Step C Synthesis of 7-amino-2,3-dihydro-2,2,6-trimethylbenzofuran as an intermediate This compound was prepared in a manner analogous to that of Step C of Example 6, using 21.8 grams (0.1 05 mole) of 2,3-dihydro-2,2,6-trimethyl-7-nitrobenzofuran, hydrogen gas, and 0.2 gram (catalyst) of platinum oxide in 50 mL of ethanol. The yield of 7-amino-2,3-dihydro-2,2,6-trimethylbenzofuran was 14.5 grams.

Step D Synthesis of 7-amino-4-bromo-2,3-dihydro-2,2,6-trimethylbenzofuran as an intermediate This compound was prepared in a manner analogous to that of Step C of Example 1, using 14.1 grams (0.080 mole) of 7-amino-2,3-dihydro-2,2,6-trimethylbenzofuran and 14.2 grams (0.080 mole) of N-bromosuccinimide in 250 mL of N,N-dimethylformamide. The yield of 7-amino-4-bromo-2, 3-dihydro-2,2,6-trimethylbenzofuran was 17.7 grams. The NMR spectrum was consistent with the proposed structure.

Step E Synthesis of 4-bromo-2,3-dihydro-2,2,6-trimethylbenzofuran as an intermediate This compound was prepared in a manner analogous to that of Step F of Example 23, using 17.2 grams (0.067 mole) of 7-amino-4-bromo-2,3-dihydro-2,2,6-trimethyl-benzofuran, 7.4 grams (0.107 mole) of sodium nitrite, and 7.5 mL (0.134 mole) of concentrated sulfuric acid in 75 mL of toluene and 300 mL of ethanol. The yield of 4-bromo-2, 3-dihydro-2,2,6-trimethylbenzofuran was 10.4 grams. The NMR spectrum was consistent with the proposed structure.

Step F Synthesis of 2,3-dihydro-2,2,6-trimethylbenzofuran-4-ylboronic acid as an intermediate This compound was prepared in a manner analogous to that of Step C of Example 2, using 10.1 grams (0.042 mole) of 4-bromo-2,3-dihydro-2,2,6-trimethylbenzofuran, 16.8 mL (0.042 mole) of n-butyllithium (2.5M in hexanes), and 14.3 mL (0.126 mole) of trimethyl borate in 100 mL of tetrahydrofuran. The yield of 2,3-dihydro-2,2,6-trimethylbenzofuran-4-ylboronic acid was 8.3 grams. The NMR spectrum was consistent with the proposed structure.

Step G Synthesis of 2-amino-5-(2,3-dihydro-2,2,6-trimethylbenzofuran-4-yl)-6-methylbenzonitrile as an intermediate This compound was prepared in a manner analogous to that of Step D of Example 2, using 8.0 grams (0.039 mole) of 2,3-dihydro-2,2,6-trimethylbenzofuran-4-ylboronic acid, 6.7 grams (0.026 mole) of 2-amino-5-iodo-6-methylbenzonitrile (prepared as in Step A of Example 17), 0.2 gram (catalyst) of tetrakis(triphenylphosphine)palladium (0), 33 mL of aqueous 2M sodium carbonate, and 200 mL of toluene. The yield of 2-amino-5-(2,3-dihydro-2,2,6-trimethylbenzofuran-4-yl)-6-methylbenzonitrile was 7.5 grams. The NMR spectrum was consistent with the proposed structure.

Step H Synthesis of 2,4-diamino-6-(2,3-dihydro-2,2,6-trimethylbenzofuran-4-yl)-5-methylquinazoline (Compound 225)

This compound was prepared in a manner analogous to that of Step E of Example 1, using 7.1 grams (0.024 mole) of 2-amino-5-(2,3-dihydro-2,2,6-trimethylbenzofuran-4-yl)-6-methylbenzonitrile and 3.4 grams (0.029 mole) of chloroformamidine hydrochloride in 15 mL of 2-methoxyethyl ether. The yield of 2,4-diamino-6-(2,3-dihydro-2,2,6-trimethylbenzofuran-4-yl)-5-methylquinazoline was 5.4 grams. The NMR spectrum was consistent with the proposed structure.

Example 31
SYNTHESIS OF 2,4-DIAMINO-6-(2,3-DIHYDRO-2,2-DIMETHYL-6-TRIFLUOROMETHYLBENZOFURAN 4-YL)-5-METHYLQUINAZOLINE (COMPOUND 226)
Step A Synthesis of 2-methyl-3-(2-cyano-3-trifluoromethylphenoxy)-1-propene as an intermediate This compound was prepared in a manner analogous to that of Step A of Example 23, using 25.0 grams (0.132 mole) of 2-fluoro-6-trifluoromethylbenzonitrile, 12.3 mL (0.135 mole) of 2-methyl-2-propen-1-ol, and 10.0 grams (0.135 mole) of powdered 85% potassium hydroxide in 250 mL of dimethyl sulfoxide. The yield of 2-methyl-3-(2-cyano-3-trifluoromethylphenoxy)-1-propene was 28.6 grams. The NMR spectrum was consistent with the proposed structure.

Step B Synthesis of 7-cyano-2,3-dihydro-2,2-dimethyl-6-trifluoromethylbenzofuran as an intermediate This compound was prepared in a manner analogous to that of Step B of Example 30, using 28.1 grams (0.116 mole) of 2-methyl-3-(2-cyano-3-trifluoromethylphenoxy)-1-propene and 0.3 gram (0.003 mole) of magnesium chloride. The yield of 7-cyano-2,3-dihydro-2,2-dimethyl-6-trifluoromethylbenzofuran was 27.5 grams, mp 79°–83° C. The NMR spectrum was consistent with the proposed structure.

Step C Synthesis of 7-aminocarbonyl-2,3-dihydro-2,2-dimethyl-6-trifluoromethylbenzofuran as an intermediate This compound was prepared in a manner analogous to that of Step C of Example 23, using 27.0 grams (0.112 mole) of 7-cyano-2,3-dihydro-2,2-dimethyl-6-trifluoromethylbenzofuran and 12.6 grams (0.224 mole) of powdered 85% potassium hydroxide in 250 mL of 2-methyl-2-propanol. The yield of 7-aminocarbonyl-2,3-dihydro-2,2-dimethyl-6-trifluoromethylbenzofuran was 13.0 grams. The NMR spectrum was consistent with the proposed structure.

Step D Synthesis of 7-amino-2,3-dihydro-2,2-dimethyl-6-trifluoromethylbenzofuran as an intermediate This compound was prepared in a manner analogous to that of Step D of Example 23, using 12.6 grams (0.049 mole) of 7-aminocarbonyl-2,3-dihydro-2,2-dimethyl-6-trifluoromethylbenzofuran, 7.8 grams (0.196 mole) of sodium hydroxide, 3.8 grams (0.074 mole) of bromine in 150 mL of water and 150 mL of dioxane. The yield of 7-amino-2,3-dihydro-2,2-dimethyl-6-trifluoromethylbenzofuran was 7.5 grams. The NMR spectrum was consistent with the proposed structure. Step E Synthesis of 7-amino-4-bromo-2,3-dihydro-2,2-dimethyl-6-trifluoromethylbenzofuran as an intermediate This compound was prepared in a manner analogous to that of Step C of Example 1, using 7.2 grams (0.031 mole) of 7-amino-2,3-dihydro-2,2-dimethyl-6-trifluoromethylbenzofuran and 5.5 grams (0.031 mole) of N-bromosuccinimide in about 100 mL of N,N-dimethylformamide. The yield of 7-amino-4-bromo-2,3-dihydro-2,2-dimethyl-6-trifluoromethylbenzofuran was 9.5 grams. The NMR spectrum was consistent with the proposed structure.

Step F Synthesis of 4-bromo-2,3-dihydro-2,2-dimethyl-6-trifluoromethylbenzofuran as an intermediate This compound was prepared in a manner analogous to that of Step F of Example 23, using 9.3 grams (0.030 mole) of 7-amino-4-bromo-2,3-dihydro-2,2-dimethyl-6-trifluoromethylbenzofuran. 3.3 grams (0.048 mole) of sodium nitrite, and 3.3 mL (0.060 mole) of concentrated sulfuric acid in 50 mL of toluene and 150 mL of ethanol. The yield of 4-bromo-2,3-dihydro-2,2-dimethyl-6-trifluoromethylbenzofuran was 7.7 grams. The NMR spectrum was consistent with the proposed structure.

Step G Synthesis of 2,3-dihydro-2,2-dimethyl-6-trifluoromethylbenzofuran-4-ylboronic acid as an intermediate This compound was prepared in a manner analogous to that of Step C of Example 2, using 7.4 grams (0.025 mole) of 4-bromo-2,3-dihydro-2,2-dimethyl-6-trifluoromethylbenzofuran, 10.0 mL (0.025 mole) of n-butyllithium (2.5M in hexanes), and 18.5 mL (0.108 mole) of trimethyl borate in 75 mL of tetrahydrofuran. The yield of 2,3-dihydro-2,2-dimethyl-6-trifluoromethylbenzofuran-4-ylboronic acid was 6.4 grams. The NMR spectrum was consistent with the proposed structure.

Step H Synthesis of 2-amino-5-(2,3-dihydro-2,2-dimethyl-6-trifluoromethylbenzofuran-4-yl)-6-methylbenzonitrile as an intermediate This compound was prepared in a manner analogous to that of Step D of Example 2, using 6.4 grams (0.024 mole) of 2,3-dihydro-2,2-dimethyl-6-trifluoromethylbenzofuran-4-ylboronic acid, 3.1 grams (0.024 mole) of 2-amino-5-iodo-6-methylbenzonitrile (prepared as in Step A of Example 17), 0.2 gram (catalyst) of tetrakis (triphenylphosphine)palladium(0), 15 mL of 2M sodium carbonate, and 75 mL of toluene. The yield of 2-amino-5-(2,3-dihydro-2,2-dimethyl-6-trifluoromethylbenzofuran-4-yl)-6-methylbenzonitrile was 3.7 grams. The NMR spectrum was consistent with the proposed structure.

Step I Synthesis of 2,4-diamino-6-(2,3-dihydro-2,2-dimethyl-6-trifluoromethylbenzofuran-4-yl)-5-methylquinazoline (Compound 226)

This compound was prepared in a manner analogous to that of Step E of Example 1, using 3.3.grams (0.009 mole) of 2-amino-5-(2,3-dihydro-2,2-dimethyl-6-trifluoromethylbenzofuran-4-yl)-6-methylbenzonitrile and 1.3 grams (0.011 mole) of chloroformamidine hydrochloride in 20 mL of 2-methoxyethyl ether. The yield of 2,4-diamino-6-(2,3-dihydro-2,2-dimethyl-6-trifluoromethylbenzofuran-4-yl)-5-methylquinazoline was 2.7 grams. The NMR spectrum was consistent with the proposed structure.

Example 32
SYNTHESIS OF 2,4-DI(1-OXO-3,6,9-TRIOXADECANEAMINO)-5-METHYL-6-[3,5-DI(TRIFLUOROMETHYL)PHENYL]QUINAZOLINE (COMPOUND 267)
Step A Synthesis of 3,6,9-trioxadecanoyl chloride as an intermediate Thionyl chloride, 8.0 grams (0.112 mole) was stirred, and 10.0 grams (0.056 mole) of 3,6,9-trioxadecanoic acid was added dropwise during a 45 minute period. Upon completion of addition, the reaction mixture was warmed to reflux where it stirred for 45 minutes. The reaction mixture was cooled, yielding 3,6,9-trioxadecanoyl chloride. An 80% yield of acid chloride was assumed.

Step B Synthesis of 3,6,9-trioxadecanoic anhydride as an intermediate The cooled reaction mixture from Step A was stirred, diluted with 50 mL of toluene, and 7.1 grams (0.090 mole) of pyridine was added. To this was added dropwise 8.0 grams (0.045 mole) of 3,6,9-trioxadecanoic acid. Upon completion of addition, the reaction mixture was stirred at ambient temperature for one hour. The reaction mixture was then filtered to remove a precipitate. The filtrate was concentrated under reduced pressure, yielding 14.0 grams of 3,6,9-trioxadecanoic anhydride. The NMR spectrum was consistent with the proposed structure.

Step C Synthesis of 2,4-di(1-oxo-3,6,9-trioxadecaneamino)-5-methyl-6-[3,5-di(trifluoromethyl)phenyl]quinazoline (Compound 267)

Under a nitrogen atmosphere, a stirred solution of 1.5 grams (0.004 mole) of 2,4-diamino-5-methyl-6-[3,5-di(trifluoromethyl)phenyl]quinazoline (Compound 63-prepared as in Example 1), 3.9 grams (0.012 mole) of 3,6,9-trioxadecanoic anhydride, 1.2 grams (0.016 mole) of pyridine, and 0.14 gram (0.001 mole) of dimethylaminopyridine in 20 mL of dioxane was heated at reflux for seven hours. After this time, the reaction mixture was poured into 400 mL of ice-water. The mixture was stirred until the ice melted, and then it was filtered to collect a gummy solid. The solid was dissolved in diethyl ether and washed in turn with two 25 mL portions of aqueous 10% citric acid, 25 mL of an aqueous solution saturated with sodium chloride, 25 mL of an aqueous solution saturated with sodium bicarbonate, and 25 mL of an aqueous solution saturated with sodium chloride. The organic layer was dried with sodium sulfate and filtered. The filtrate was concentrated under reduced pressure, yielding about 0.8 gram of 2,4-di(1-oxo-3,6,9-trioxadecaneamino)-5-methyl-6-[3,5-di(trifluoromethyl)phenyl]quinazoline. The NMR spectrum was consistent with the-proposed structure.

Example 33
SYNTHESIS OF 2,4-DIAMINO-6-(6—CHLORO-2,2-DIMETHYLBENZODIOXOL-4-YL)-5-METHYLQUINAZOLINE (COMPOUND 235)

Step A Synthesis of 2-bromo-4-chlorocatechol as an intermediate

A stirred solution of 25.0 grams (0.106 mole) of 2-bromo-4-chloro-5-formylphenol in 106 mL (0.106 mole) of aqueous 1N sodium hydroxide was warmed to about 50° C., and 150 mL (0.133 mole) of aqueous 3% hydrogen peroxide was added dropwise. Upon completion of addition, the reaction mixture was allowed to cool to ambient temperature as it stirred for about 18 hours. After this time, the reaction mixture was made acidic with aqueous 6N hydrochloric acid. The mixture was then filtered to collect a solid. The solid was washed with water and dried under vacuum, yielding 21.2 grams of 2-bromo-4-chlorocatechol. The NMR spectrum was consistent with the proposed structure.

Step B Synthesis of 4-bromo-6-chloro-2,2-dimethylbenzodioxole as an intermediate A solution of 4.7 grams (0.021 mole) of 2-bromo-4-chlorocatechol and 10 mL (0.136 mole) of acetone in 100 mL of methylene chloride was stirred, and 18.0 grams (0.128 mole) of phosphorus pentoxide was added in one portion. Upon completion of addition, the reaction mixture was stirred at ambient temperature for about 18 hours. After this time, the supernatant liquid was decanted from a solid residue. The residue was washed with methylene chloride, and the wash was combined with the supernatant liquid. The combination was then washed twice each with aqueous 1N sodium hydroxide and an aqueous solution saturated with sodium chloride. The organic layer was dried with magnesium sulfate and filtered. The filtrate was concentrated under reduced pressure to a residue. The residue was subjected to column chromatography on silica gel, using 5% ethyl acetate in pentane as the eluant. The product-containing fractions were combined and concentrated under reduced pressure, yielding about 0.9 gram of 4-bromo-6-chloro-2,2-dimethylbenzodioxole. The NMR spectrum was consistent with the proposed structure. The reaction was repeated.

Step C Synthesis of 6-chloro-2,2-dimethylbenzodioxol-4-ylboronic acid as an intermediate This compound was prepared in a manner analogous to that of Step C of Example 2, using 5.8 grams (0.022 mole) of 4-bromo-6-chloro-2,2-dimethylbenzodioxole, 0.5 gram (0.022 mole) of magnesium turnings, and 3.4 grams (0.033 mole) of trimethyl borate in 100 mL of tetrahydrofuran. The yield of 6-chloro-2,2-dimethylbenzodioxol-4-ylboronic acid was about four grams. The NMR spectrum was consistent with the proposed structure.

Step D Synthesis of 2-amino-5-(6-chloro-2,2-dimethylbenzodioxol-4-yl)-6-methylbenzonitrile as an intermediate This compound was prepared in a manner analogous to that of Step D of Example 2, using 1.9 grams (0.009 mole) of 2-amino-5-bromo-6-methylbenzonitrile, 4.0 grams (0.018 mole) of 6-chloro-2,2-dimethylbenzodioxol-4-ylboronic acid, 15 mL (0.009 mole) of aqueous 2N sodium carbonate, and 0.1 gram oftetrakis(triphenylphosphine)palladium(0) in 10 mL of toluene. The yield of 2-amino-5-(6-chloro-2,2-dimethylbenzodioxol-4-yl)-6-methylbenzonitrile was 2.1 grams, mp 156°–161° C. The NMR spectrum was consistent with the proposed structure. tep E Synthesis of 2,4-diamino-6-(6-chloro-2,2-dimethylbenzodioxol-4-yl)-5-methylquinazoline (Compound 235)

This compound was prepared in a manner analogous to that of Step E of Example 1, using 1.8 grams (0.006 mole) of 2-amino-5-(6-chloro-2,2-dimethylbenzodioxol-4-yl)-6-methylbenzonitrile and 0.8 gram (0.008 mole) of chloroformamidine hydrochloride in 10 mL of 2-methoxyethyl ether. The yield of 2,4-diamino-6-(6-chloro-2,2-dimethylbenzodioxol-4-yl)-5-methylquinazoline was 0.9 gram, mp 235°–238° C. The NMR spectrum was consistent with the proposed structure.

TABLE 1

Substituted 2,4-Diaminoquinazolines as Insecticides

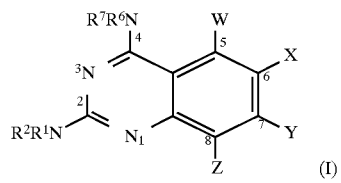

(I)

Where $R^1$, $R^2$, $R^6$ and $R^7$ are hydrogen.

| Cmpd. No. | W | X | Y | Z |
|---|---|---|---|---|
| 1 | H | H | H | H |
| 2 | Cl | H | H | H |
| 3 | F | H | H | H |
| 4 | Br | H | H | H |
| 5 | I | H | H | H |
| 6 | H | Cl | H | H |
| 7 | H | Cl $NH_4^+Cl^-$ complex | H | H |
| 8 | H | Br | H | H |
| 9 | H | F | H | H |
| 10 | H | H | Cl | H |
| 11 | H | H | Br | H |
| 12 | H | H | F | H |
| 13 | H | H | I | H |
| 14 | H | H | H | F |
| 15 | H | Cl | H | Cl |
| 16 | H | Br | H | Br |
| 17 | F | F | H | H |
| 18 | H | F | F | H |
| 19 | H | H | F | F |
| 20 | Cl | Br | H | H |
| 21 | H | Cl | H | Br |
| 22 | H | Br | H | Cl |
| 23 | Cl | CN | H | H |
| 24 | Cl | —NH$_2$ | H | H |
| 25 | Cl | Br | H | Br |
| 26 | F | F | F | F |
| 27 | —CH$_3$ | H | H | H |
| 28 | H | —CH$_3$ | H | H |
| 29 | H | H | —CH$_3$ | H |
| 30 | —CH$_3$ | —NO$_2$ | H | H |
| 31 | —CH$_3$ | H | H | —NO$_2$ |
| 32 | —CH$_3$ | —NH$_2$ | H | H |
| 33 | —CF$_3$ | H | H | H |
| 34 | H | —CF$_3$ | H | H |
| 35 | H | H | H | —CF$_3$ |
| 36 | —OC$_2$H$_5$ | H | H | H |
| 37 | —OCH$_2$CF$_3$ | H | H | H |
| 38 | H | —NH$_2$ | H | H |
| 39 | —N(CH$_3$)$_2$ | H | H | H |
| 40 | —CN | H | H | H |
| 41 | phenyl | H | H | H |
| 42 | H | phenyl | H | H |
| 43 | H | H | phenyl | H |
| 44 | H | 4-C(CH$_3$)$_3$-phenyl | H | H |
| 45 | H | 3,5-bis(CF$_3$)-phenyl | H | H |
| 46 | H | (footnote 1) | H | H |
| 47 | Cl | phenyl | H | H |

TABLE 1-continued

Substituted 2,4-Diaminoquinazolines as Insecticides

| | | | | |
|---|---|---|---|---|
| 48 | Cl | 4-Cl-phenyl | H | H |
| 49 | Cl | 4-F-phenyl | H | H |
| 50 | Cl | 2,4-diCl-phenyl | H | H |
| 51 | Cl Methanol Solvate | 3,5-diCl-phenyl | H | H |
| 52 | Cl | 3-Cl-4-F-phenyl | H | H |
| 53 | Cl | 3,5-di(CF$_3$)-phenyl | H | H |
| 54 | Cl | 1-naphthyl | H | H |
| 55 | H | Cl | H | phenyl |
| 56 | H | phenyl | H | Cl |
| 57 | phenyl | H | phenyl | H |
| 58 | H | phenyl monohydrate | H | phenyl |
| 59 | Cl | phenyl | H | phenyl |
| 60 | —CH$_3$ | 3,5-di(CH$_3$)-phenyl | H | H |
| 61 | —CH$_3$ Methanol Solvate | 3,5-di(CH$_3$)-phenyl | H | H |
| 62 | —CH$_3$ | 4-C(CH$_3$)$_3$-phenyl | H | H |
| 63 | —CH$_3$ | 3,5-di(CF$_3$)-phenyl | H | H |

TABLE 1-continued

Substituted 2,4-Diaminoquinazolines as Insecticides

| 64 | (3,5-bis(CF₃)phenyl) | (3,5-bis(CF₃)phenyl) | H | H |

Where $R^1$, $R^2$, $R^6$, $R^7$, Y and Z are hydrogen; W is chloro; and X is

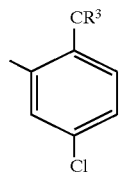

| Cmpd. No. | $R^3$ |
|---|---|
| 65 | H |
| 66 | —CH₃ |
| 67 | —C₅H₁₁ |
| 68 | —C₁₁H₂₃ |
| 69 | —CH₂Si(CH₃)₃ |
| 70 | —CH₂-(4-Cl-phenyl) |
| 71 | —(CH₂)₄-(4-Cl-phenyl) |
| 72 | —CH₂-(pentafluorophenyl) |
| 73 | —CH₂-(2-pyridyl) |
| 74 | —C₂H₄O-(4-S(O)₂C₃H₇-phenyl) |

Where $R^1$, $R^2$, $R^6$ and $R^7$ are hydrogen.

| Cmpd. No. | W | X | Y | Z |
|---|---|---|---|---|
| 75 | —S-(3,4-diCl-phenyl) | H | H | H |
| 76 | —S(O)-(3,4-diCl-phenyl) | H | H | H |
| 77 | —SCH₂-(3,4-diCl-phenyl) | H | H | H |

TABLE 1-continued

Substituted 2,4-Diaminoquinazolines as Insecticides

| 78 | —CH₂S—(3,4-dichlorophenyl) | H | H | H |
| 79 | H | —(CH₂)₂—phenyl | | H | H |
| 80 | H | —S—(3,4-dichlorophenyl) | H | H |
| 81 | H | —S(O)—(3,4-dichlorophenyl) | H | H |
| 82 | H | —S(O)₂—(3,4-dichlorophenyl) | H | H |
| 83 | —(CH₂)₂—(2-naphthyl) | H | H | H |
| 84 | CH₃CH=CH—(2-naphthyl), cis isomer | H | H | H |
| 85 | CH₃CH=CH—(2-naphthyl), trans isomer | H | H | H |
| 86 | —S—(2-naphthyl) | H | H | H |
| 87 | —S(O)—(2-naphthyl) | H | H | H |
| 88 | H | —S—(2-naphthyl) | H | H |
| 89 | H | —S(O)—(2-naphthyl) | H | H |
| 90 | H | —S(O)₂—(2-naphthyl) | H | H |

TABLE 1-continued

Substituted 2,4-Diaminoquinazolines as Insecticides

Where $R^1$, $R^2$, $R^6$, $R^7$, Y, and Z are hydrogen; and X is

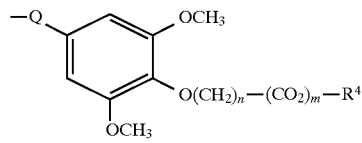

| Cmpd. No. | W | $Q^{(2)}$ | n | m | $R^4$ |
|---|---|---|---|---|---|
| 91 | Cl | —N=CH— | 1 | 0 | H |
| 92 | Cl | —CH$_2$NH— | 1 Hemimethanol | 0 | H |
| 93 | —CH$_3$ | —CH$_2$NH— | 1 | 0 | H |
| 94 | H | —CH$_2$NH— | 1 2.HCl | 1 | H |
| 95 | H | —CH$_2$NH— | 1 | 1 | —C$_2$H$_5$ |
| 96 | H | —CH$_2$NH— | 2 2.HCl | 1 | H |
| 97 | H | —CH$_2$NH— | 2 | 1 | —C$_2$H$_5$ |
| 98 | H | —CH$_2$NH— | 3 2.HCl | 1 | H |
| 99 | H | —CH$_2$NH— | 3 | 1 | —C$_2$H$_5$ |
| 100 | Cl | —CH$_2$NH— | 2 | 1 | —C$_2$H$_5$ |
| 101 | —CH$_3$ | —CH$_2$NH— | 2 2.HCl | 1 | H |
| 102 | —CH$_3$ | —CH$_2$NH— | 2 | 1 | —C$_2$H$_5$ |

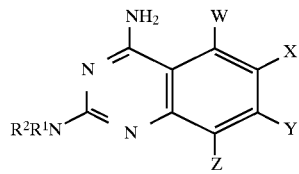

Where $R^1$, $R^2$, $R^6$ and $R^7$ are hydrogen.

| Cmpd. No | W | X | Y | Z |
|---|---|---|---|---|
| 103 | F | H | F | H |
| 104 | F | H | H | Cl |
| 105 | H | Cl | H | F |

Where $R^1$, $R^2$, $R^6$, $R^7$, Y, and Z are hydrogen.

| Cmpd. No. | W | X |
|---|---|---|
| 106 | H | 2-chlorophenyl |
| 107 | H | 2,3-dimethylphenyl |
| 108 | H | 2,3,5,6-tetramethylphenyl |

TABLE 1-continued
Substituted 2,4-Diaminoquinazolines as Insecticides
| 109 | H | 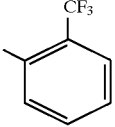 (2-CF₃-phenyl) |
| 110 | H | 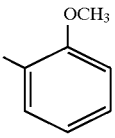 (2-OCH₃-phenyl) |
| 111 | H | 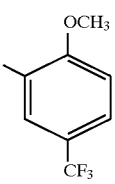 (2-OCH₃-4-CF₃-phenyl) |
| 112 | —CH₃ | phenyl |
| 113 | —CH₃ | 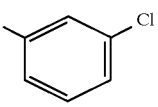 (3-Cl-phenyl) |
| 114 | —CH₃ | 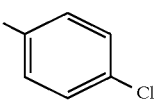 (4-Cl-phenyl) |
| 115 | —CH₃ | 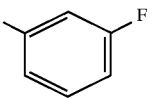 (3-F-phenyl) |
| 116 | —CH₃ | 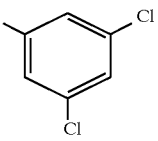 (3,5-diCl-phenyl) |
| 117 | —CH₃ | 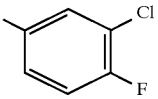 (3-Cl-4-F-phenyl) |
| 118 | —CH₃ | 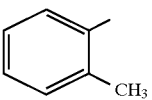 (2-CH₃-phenyl) |
| 119 | —CH₃ | 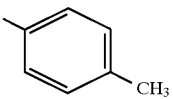 (4-CH₃-phenyl) |
| 120 | —CH₃ | 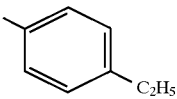 (4-C₂H₅-phenyl) |

TABLE 1-continued
Substituted 2,4-Diaminoquinazolines as Insecticides
| | | |
|---|---|---|
| 121 | —CH$_3$ | 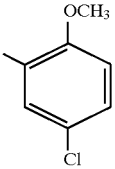 |
| 122 | —CH$_3$ | 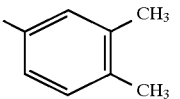 |
| 123 | —CH$_3$ | 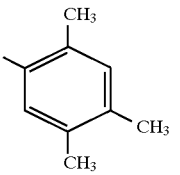 |
| 124 | —CH$_3$ | 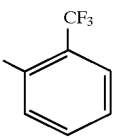 |
| 125 | —CH$_3$ | 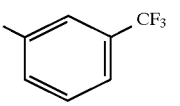 |
| 126 | —CH$_3$ | 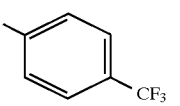 |
| 127 | —CH$_3$ | 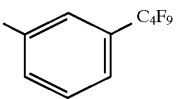 |
| 128 | —CH$_3$ | 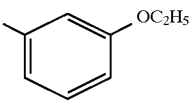 |
| 129 | —CH$_3$ | 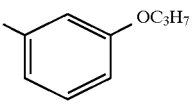 |
| 130 | —CH$_3$ | 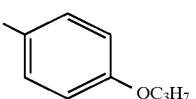 |
| 131 | —CH$_3$ | 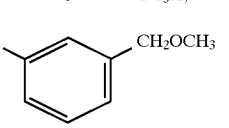 |
| 132 | —CH$_3$ | 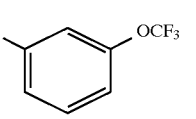 |

TABLE 1-continued
Substituted 2,4-Diaminoquinazolines as Insecticides
| 133 | —CH₃ | 3-cyanophenyl |
| 134 | —CH₃ | 3-nitrophenyl |
| 135 | —CH₃ | 3-C(O)NH₂-phenyl |
| 136 | —CH₃ | 3-NHC(O)C₃H₇-phenyl |
| 137 | —CH₃ | 3-NHS(O)₂CH₃-phenyl |
| 138 | —CH₃ | 3-phenyl-phenyl (biphenyl) |
| 139 | —CH₃ | —CH₂CH₂-phenyl |
| 140 | —CH₃ | —CH₂CH₂-(3-CF₃-phenyl) |
| 141 | —CH₃ | —CH₂CH₂-(3,5-(CF₃)₂-phenyl) |
Where $R^1$, $R^2$, $R^6$, $R^7$, Y and Z are hydrogen; W is methyl; and X is
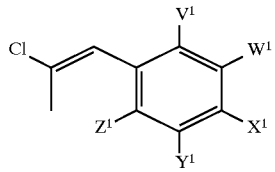
| Cmpd. No | V¹ | W¹ | X¹ | Y¹ | Z¹ |
|---|---|---|---|---|---|
| 142 | H | H | H | H | H |
| 143 | H | H | —CF₃ | H | H |
| 144 | H | —CF₃ | H | —CF₃ | H |

TABLE 1-continued

Substituted 2,4-Diaminoquinazolines as Insecticides

Where $R^1$, $R^2$, $R^6$, $R^7$, Y and Z are hydrogen.

| Cmpd. No | W | X |
|---|---|---|
| 145 | —CH$_3$ | 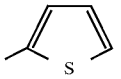 |
| 146 | —CH$_3$ | 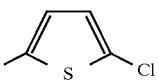 |
| 147 | —CH$_3$ | 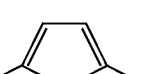 |
| 148 | —CF$_3$ | 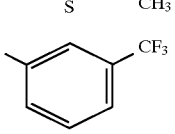 |

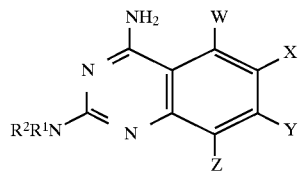

Where $R^1$, $R^2$, $R^6$, $R^7$, Y, and Z are hydrogen; W is methyl; and X is:

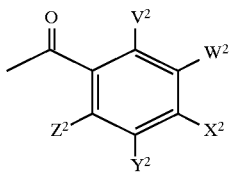

| Cmpd. No. | V$^2$ | W$^2$ | X$^2$ | Y$^2$ | Z$^2$ |
|---|---|---|---|---|---|
| 149 | H | H | H | H | H |
| 150 | Cl | H | H | H | H |
| 151 | H | Cl | H | H | H |
| 152 | H | Cl | H | Cl | H |
| 153 | H | Cl | Cl | H | H |
| 154 | H | H | Cl | H | H |
| 155 | —CF$_3$ | H | H | H | H |
| 156 | H | —CF$_3$ | H | H | H |
| 157 | H | —CF$_3$ | H | —CF$_3$ | H |
| 158 | H | H | —CF$_3$ | H | H |
| 159 | H | —CO$_2$CH$_3$ | H | H | H |
| 160 | F | H | H | H | H |
| 161 | H | H | —CO$_2$CH$_3$ | H | H |
| 162 | H | F | H | H | H |
| 163 | H | —CN | H | H | H |
| 164 | H | F | H | F | H |
| 165 | H | H | —CN | H | H |
| 166 | H | H | F | H | H |
| 167 | F | H | F | H | F |
| 168 | H | 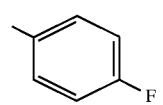 | H | H | H |
| 169 | H | 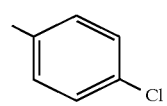 | H | H | H |

TABLE 1-continued
Substituted 2,4-Diaminoquinazolines as Insecticides
| 170 | H | 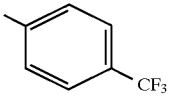 | H | H | H |
| 171 | H | H | 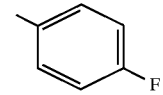 | H | H |
| 172 | H | H | 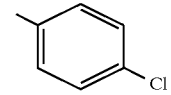 | H | H |
| 173 | H | H | 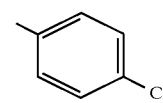 | H | H |
Where $R^1$, $R^2$, $R^6$, $R^7$, Y, and Z are hydrogen; and X is:
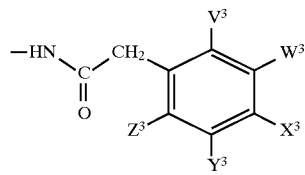
| Cmpd. No. | $W^3$ | $V^3$ | $W^3$ | $X^3$ | $Y^3$ | $Z^3$ |
|---|---|---|---|---|---|---|
| 174 | H | H | H | Cl | Cl | H |
| 175 | Cl | H | H | Cl | Cl | H |
Where $R^1$, $R^2$, $R^6$, $R^7$, Y and Z are hydrogen; W is methyl; and X is:
Cmpd. No.             X
| 176 | 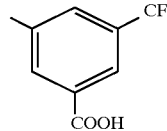 |
| 177 | 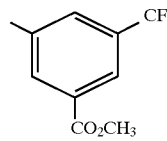 |
| 178 | 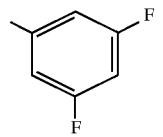 |
| 179 | 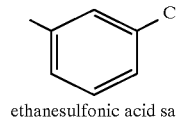<br>ethanesulfonic acid salt |
| 180 | 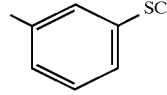 |

TABLE 1-continued
Substituted 2,4-Diaminoquinazolines as Insecticides
181 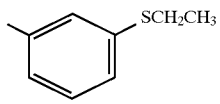
Where $R^1$, $R^2$, $R^6$, $R^7$, Y and Z are hydrogen; W is methyl; and X is:
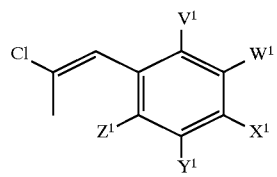
| Cmpd. No | $V^1$ | $W^1$ | $X^1$ | $Y^1$ | $Z^1$ |
|---|---|---|---|---|---|
| 182 | H | —CF3 | H | H | H |
Where $R^1$, $R^2$, $R^6$, $R^7$, Y and Z are hydrogen; W is methyl; and X is:
Cmpd. No.        X
183 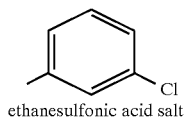
ethanesulfonic acid salt
184 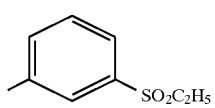
185 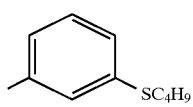
186 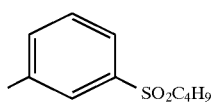
187 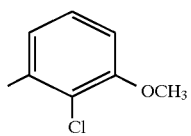
188 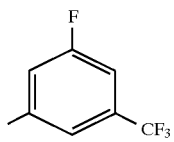
189 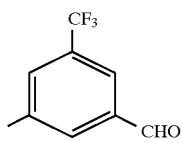

TABLE 1-continued
Substituted 2,4-Diaminoquinazolines as Insecticides
190 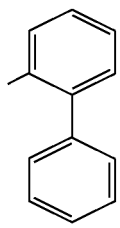
191 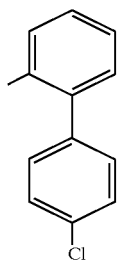
192 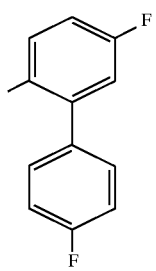
193 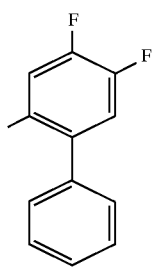
194 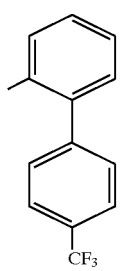
195 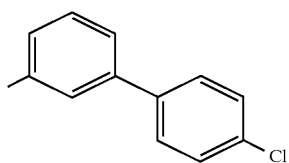

TABLE 1-continued
Substituted 2,4-Diaminoquinazolines as Insecticides
196 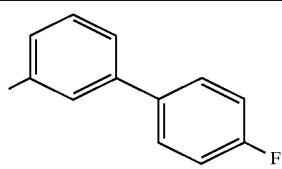
197 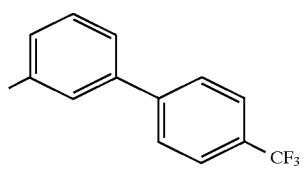
198 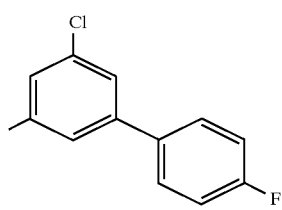
199 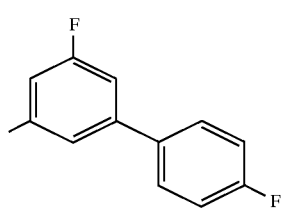
200 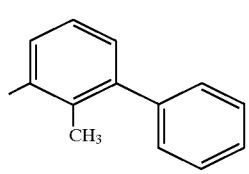
201 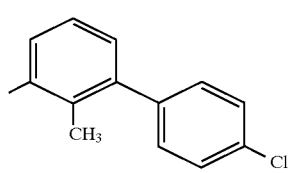
202 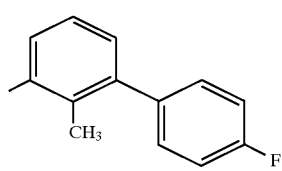
203 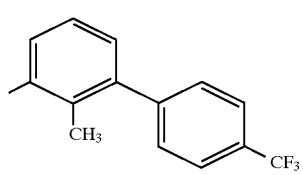
204 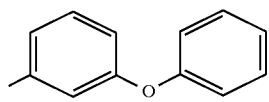

TABLE 1-continued

Substituted 2,4-Diaminoquinazolines as Insecticides

| Cmpd. No. | Structure |
|---|---|
| 205 | 3-methylphenyl 4-chlorophenyl ether |
| 206 | 3-fluoro-5-methylphenyl phenyl ether |
| 207 | 3-fluoro-5-methylphenyl 4-fluorophenyl ether |

Where R¹, R², R⁶, R⁷ and Z are hydrogen, W is methyl, and X is:

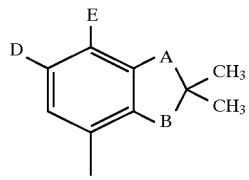

| Cmpd. No. | A | B | D | E |
|---|---|---|---|---|
| 208 | O | —CH₂— | H | H |
| 209 | —CH₂— | O | H | H |
| 210 | O | —CH₂— | Cl | H |
| 211 | —CH₂— | O | Cl | H |
| 212 | O | —C=O | H | H |

Where R¹, R², R⁶, R⁷, and Z are hydrogen, W is methyl; Y is fluoro; and X is:

| Cmpd. No. | X |
|---|---|
| 213 | 3,5-difluorophenyl |
| 214 | 3,5-bis(trifluoromethyl)phenyl |

Where R¹, R⁶, Y and Z are hydrogen, and W is methyl

| Cmpd. No. | R² | R⁷ | X |
|---|---|---|---|
| 215 | C(O)CH₃ | C(O)CH₃ | 3,5-bis(trifluoromethyl)phenyl |
| 216 | C(O)C(CH₃)₃ | C(O)C(CH₃)₃ | 3,5-bis(trifluoromethyl)phenyl |

TABLE 1-continued

Substituted 2,4-Diaminoquinazolines as Insecticides

217 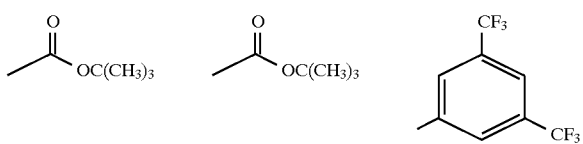

Where $R^1$, $R^2$, $R^6$, $R^7$, Y and Z are hydrogen; W is 1-methylethyl [i.e., $-CH(CH_3)_2$]; and X is:
Cmpd. No.                    X 218 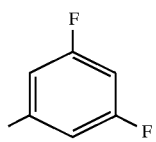

219 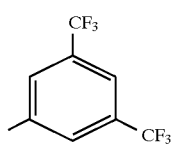

| | Where $R^1$, $R^2$, $R^6$, $R^7$, Y and Z are hydrogen | |
|---|---|---|
| Cmpd. No. | W | X |

220  H  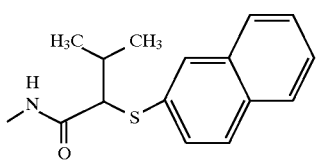

221  F  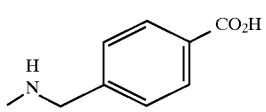

222  F  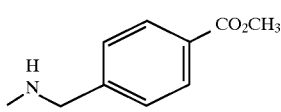

Where $R^1$, $R^2$, $R^6$, $R^7$ and Z are hydrogen; W is methyl; and X is:

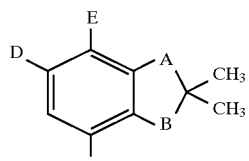

| Cmpd. No. | A | B | D | E |
|---|---|---|---|---|
| 223 | $-CH_2-$ | O | $-CH_3$ | H |
| 224 | $-CH_2-$ | O | $-CF_3$ | H |
| 225 | O | $-CH_2-$ | $-CH_3$ | H |
| 226 | O | $-CH_2-$ | $-CF_3$ | H |
| 227 | O | $-C=O$ | Cl | H |
| 228 | O | $-C=O$ | $-CH_3$ | H |
| 229 | O | $-C=O$ | $-CF_3$ | H |
| 230 | $-C=O$ | O | H | H |
| 231 | $-C=O$ | O | Cl | H |
| 232 | $-C=O$ | O | $-CH_3$ | H |
| 233 | $-C=O$ | O | $-CF_3$ | H |
| 234 | O | O | H | H |
| 235 | O | O | Cl | H |
| 236 | O | O | F | H |

TABLE 1-continued

Substituted 2,4-Diaminoquinazolines as Insecticides

| 237 | O | O | —CH₃ | H |
| 238 | O | O | —CF₃ | H |
| 239 | O | —CH₂— | F | H |
| 240 | O | —CH₂— | H | —OH |
| 241 | O | —CH₂— | H | —OCH₃ |

Where $R^1$, $R^2$, $R^6$, $R^7$, W, Y, and Z are hydrogen; and X is:

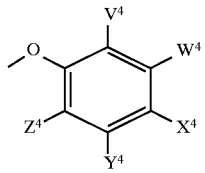

| Cmpd. No. | $V^4$ | $W^4$ | $X^4$ | $Y^4$ | $Z^4$ |
|---|---|---|---|---|---|
| 242 | H | H | Cl | H | H |
| 243 | H | Cl | H | H | H |
| 244 | H | —CF₃ | H | —CF₃ | H |
| 245 | H | —CF₃ | H | H | H |
| 246 | H | Cl | H | Cl | H |
| 247 | Cl | H | H | H | H |
| 248 | —CF₃ | H | H | H | Cl |
| 249 | H | H | —CF₃ | H | H |
| 250 | Cl | H | H | H | Cl |

Where $R^1$, $R^6$, Y, and Z are hydrogen, and W is methyl

| Cmpd. No. | $R^2$ | $R^7$ | X |
|---|---|---|---|
| 251 | —C(=O)—C(CH₃)₃ | —C(=O)—C(CH₃)₃ | 3,5-dichlorophenyl |
| 252 | —C(=O)—C₃F₇ | —C(=O)—C₃F₇ | 3,5-dichlorophenyl |
| 253 | —C(=O)—C₅H₁₁ | —C(=O)—C₅H₁₁ | 3,5-dichlorophenyl |
| 254 | —C(=O)—C₂F₅ | —C(=O)—C₂F₅ | 3,5-dichlorophenyl |
| 255 | —C(=O)—C₈H₁₇ | —C(=O)—C₈H₁₇ | 3,5-dichlorophenyl |
| 256 | —C(=O)—CH(CH₃)₂ | —C(=O)—CH(CH₃)₂ | 3,5-dichlorophenyl |

TABLE 1-continued

Substituted 2,4-Diaminoquinazolines as Insecticides

| # | R1 | R2 | Ar |
|---|---|---|---|
| 257 | COC11H23 | COC11H23 | 3,5-di-Cl-phenyl |
| 258 | COCH3 | COCH3 | 3,5-di-Cl-phenyl |
| 259 | CO-(4-Cl-C6H4) | CO-(4-Cl-C6H4) | 3,5-di-Cl-phenyl |
| 260 | COC6H5 | COC6H5 | 3,5-di-CF3-phenyl |
| 261 | COC8H17 | COC8H17 | 3,5-di-CF3-phenyl |
| 262 | COCH(CH3)2 | COCH(CH3)2 | 3,5-di-CF3-phenyl |
| 263 | COC2F5 | COC2F5 | 3,5-di-CF3-phenyl |
| 264 | COCH2OC2H5 | COCH2OC2H5 | 3,5-di-CF3-phenyl |
| 265 | COC5H11 | COC5H11 | 3,5-di-CF3-phenyl |
| 266 | COC2H4OC2H5 | COC2H4OC2H5 | 3,5-di-CF3-phenyl |

TABLE 1-continued

Substituted 2,4-Diaminoquinazolines as Insecticides

| Cmpd. No. | R¹=R² | R⁶=R⁷ | Aryl |
|---|---|---|---|
| 267 | –C(O)CH₂OC₂H₄OC₂H₄OCH₃ | –C(O)CH₂OC₂H₄OC₂H₄OCH₃ | 3,5-bis(CF₃)phenyl |
| 268 | –C(O)C≡CCH₃ | –C(O)C≡CCH₃ | 3,5-bis(CF₃)phenyl |
| 269 | –C(O)CH₂SO₂CH₃ | –C(O)CH₂SO₂CH₃ | 3,5-bis(CF₃)phenyl |
| 270 | –C(O)CH₂OC₂H₄OC₂H₅ | –C(O)CH₂OC₂H₄OC₂H₅ | 3,5-bis(CF₃)phenyl |
| 271 | –C(O)C₂H₄OC₂H₄OC₂H₅ | –C(O)C₂H₄OC₂H₄OC₂H₅ | 3,5-bis(CF₃)phenyl |

Where Y and Z are hydrogen, W is methyl,

X is 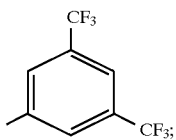 3,5-bis(CF₃)phenyl and R¹ and R² taken together, and R⁶ and R⁷ taken together form the group

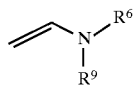

| Cmpd. No. | R⁸ | R⁹ |
|---|---|---|
| 272 | –CH₃ | –CH₃ |
| 273 | –CH(CH₃)₂ | –CH(CH₃)₂ |
| 274 | –CH₂CH₂CH₂CH₂CH₂– | |

Where R¹, R², R⁶ and R⁷ are hydrogen

| Cmpd. No. | W | X | Y | Z |
|---|---|---|---|---|
| 275 | –CH₃ | 3,5-bis(CF₃)phenyl | H, HCl Salt | H |
| 276 | –CH₃ | 3,5-bis(CF₃)phenyl | H, Gluconic Acid Salt | H |

TABLE 1-continued

Substituted 2,4-Diaminoquinazolines as Insecticides

| 277 | —CH$_3$ | CF$_3$ (3,5-bis-CF$_3$ phenyl) | H Ethane-sulfonic Acid Salt | H |
| 278 | —CH$_3$ | CF$_3$ (3,5-bis-CF$_3$ phenyl) | H Pamoic Acid Salt | H |

Where R$^1$, R$^2$, R$^6$, R$^7$, Y, and Z are hydrogen, W is methyl, and X is:

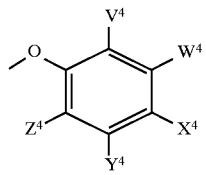

| Cmpd. No. | V$^4$ | W$^4$ | X$^4$ | Y$^4$ | Z$^4$ |
|---|---|---|---|---|---|
| 279 | Cl | H | H | H | H |
| 280 | H | Cl | H | H | H |
| 281 | H | H | Cl | H | H |
| 282 | —CF$_3$ | H | H | H | H |
| 283 | H | —CF$_3$ | H | H | H |
| 284 | H | H | —CF$_3$ | H | H |

FOOTNOTES
[1] In Compound 46, X is
—CHN(CH$_3$)

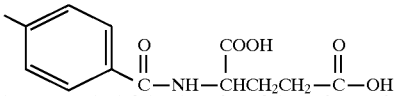

[2] In Compounds 91–102, the left hand portion of the moiety Q, is attached to the quinazoline ring.

TABLE 1-a

Melting Points and Empirical Formulas of Compounds of Table 1

| COMPOUND | MELTING POINT (°C.) | EMPIRICAL FORMULA |
|---|---|---|
| 1 | 240–246 | C$_8$H$_8$N$_4$ |
| 2 | 186–188 | C$_8$H$_7$ClN$_4$ |
| 3 | 249–251 | C$_8$H$_7$FN$_4$ |
| 4 | 202–204 | C$_8$H$_7$BrN$_4$ |
| 5 | 192–193 | C$_8$H$_7$IN$_4$ |
| 6 | 264–270 | C$_8$H$_7$ClN$_4$ |
| 7 | >360 | C$_8$H$_{11}$Cl$_2$N$_5$ |
| 8 | 264–266 | C$_8$H$_7$BrN$_4$ |
| 9 | 315–320 | C$_8$H$_7$FN$_4$ |
| 10 | 246–247 | C$_8$H$_7$ClN$_4$ |
| 11 | 255–256 | C$_8$H$_7$BrN$_4$ |
| 12 | 274–277 | C$_8$H$_7$FN$_4$ |
| 13 | 266–267 | C$_8$H$_7$IN$_4$ |
| 14 | 285–287 | C$_8$H$_7$FN$_4$ |
| 15 | >320 | C$_8$H$_6$Cl$_2$N$_4$ |
| 16 | >256 | C$_8$H$_6$Br$_2$N$_4$ |
| 17 | 256–257 | C$_8$H$_6$F$_2$N$_4$ |
| 18 | 172–173 | C$_8$H$_6$F$_2$N$_4$ |
| 19 | 295–296 | C$_8$H$_6$F$_2$N$_4$ |
| 20 | 273–275 | C$_8$H$_6$BrClN$_4$ |
| 21 | >325 | C$_8$H$_6$BrClN$_4$ |
| 22 | >325 | C$_8$H$_6$BrClN$_4$ |
| 23 | 287, dec. | C$_9$H$_6$ClN$_5$ |
| 24 | 204–205 | C$_8$H$_8$ClN$_5$ |
| 25 | 188–198 | C$_8$H$_5$Br$_2$ClN$_4$ |
| 26 | 215–220 | C$_8$H$_4$F$_4$N$_4$ |
| 27 | 210–212 | C$_9$H$_{10}$N$_4$ |
| 28 | 250–253 | C$_9$H$_{10}$N$_4$ |
| 29 | 226–227 | C$_9$H$_{10}$N$_4$ |
| 30 | 228, dec. | C$_9$H$_9$N$_5$O$_2$ |
| 31 | 293, dec. | C$_9$H$_9$N$_5$O$_2$ |
| 32 | 219–222 | C$_9$H$_{11}$N$_5$ |
| 33 | 176–178 | C$_9$H$_7$F$_3$N$_4$ |
| 34 | 234–236 | C$_9$H$_7$F$_3$N$_4$ |
| 35 | 244–246 | C$_9$H$_7$F$_3$N$_4$ |
| 36 | 214–216 | C$_{10}$H$_{12}$N$_4$O |
| 37 | 245–246 | C$_{10}$H$_9$F$_3$N$_4$O |
| 38 | 255–258 | C$_8$H$_9$N$_5$ |
| 40 | 231–232 | C$_9$H$_7$N$_5$ |
| 41 | 249–259 | C$_{14}$H$_{12}$N$_4$ |
| 42 | 244 partial, 255–257 | C$_{14}$H$_{12}$N$_4$ |
| 43 | 254–258 | C$_{14}$H$_{12}$N$_4$ |
| 44 | 287–290 | C$_{18}$H$_{20}$N$_4$ |
| 45 | 256–259 | C$_{16}$H$_{10}$F$_6$N$_4$ |
| 46 | 208–210, dec. | C$_{22}$H$_{24}$N$_6$O$_5$ |
| 47 | 248–251 | C$_{14}$H$_{11}$ClN$_4$ |
| 48 | 256–259 | C$_{14}$H$_{10}$Cl$_2$N$_4$ |
| 49 | 268–280 | C$_{14}$H$_{10}$ClFN$_4$ |

TABLE 1-a-continued

Melting Points and Empirical Formulas of Compounds of Table 1

| COMPOUND | MELTING POINT (°C.) | EMPIRICAL FORMULA |
|---|---|---|
| 50 | 238–240 | $C_{14}H_9Cl_3N_4$ |
| 51 | 245–250 | $C_{15}H_{13}Cl_3N_4O$ |
| 52 | 222–225 | $C_{14}H_9Cl_2FN_4$ |
| 53 | >280 | $C_{16}H_9ClF_6N_4$ |
| 54 | 224–229 | $C_{18}H_{13}ClN_4$ |
| 55 | 264–268 | $C_{14}H_{11}ClN_4$ |
| 56 | 230–238, dec. | $C_{14}H_{11}ClN_4$ |
| 57 | 115–125 | $C_{20}H_{16}N_4$ |
| 58 | 250–258, dec. | $C_{20}H_{18}N_4O$ |
| 59 | 238–242. dec. | $C_{20}H_{15}ClN_4$ |
| 60 | 245–247 | $C_{16}H_{16}N_4$ |
| 61 | 251–253 | $C_{18}H_{22}N_4O$ |
| 62 | 308–311, dec. | $C_{19}H_{22}N_4$ |
| 63 | 222–225 | $C_{17}H_{12}F_6N_4$ |
| 64 | 187–191 | $C_{24}H_{12}F_{12}N_4$ |
| 65 | — | $C_{14}H_{10}Cl_2N_4O$ |
| 66 | — | $C_{15}H_{12}Cl_2N_4O$ |
| 67 | 157–162 | $C_{19}H_{20}Cl_2N_4O$ |
| 68 | — | $C_{25}H_{32}Cl_2N_4O$ |
| 69 | 180–183 | $C_{18}H_{29}Cl_2N_4O$ |
| 70 | — | $C_{21}H_{15}Cl_3N_4OSi$ |
| 71 | — | $C_{24}H_{21}Cl_3N_4O$ |
| 72 | 97–110 | $C_{21}H_{11}Cl_2F_5N_4O$ |
| 73 | 112–120 | $C_{20}H_{15}Cl_2N_5O$ |
| 74 | 105–112 | $C_{25}H_{24}Cl_2N_4O_4S$ |
| 75 | 232–234 | $C_{14}H_{10}ClN_4O$ |
| 76 | 268–270 | $C_{14}H_{10}Cl_2N_4O_2S$ |
| 77 | 197–199 | $C_{15}H_{12}N_4S$ |
| 78 | 200–205 | $C_{15}H_{12}N_4S$ |
| 79 | 178–180 | $C_{16}H_{16}N_4$ |
| 80 | 232–234 | $C_{14}H_{10}Cl_2N_4S$ |
| 81 | >250 | $C_{14}H_{10}Cl_2OS$ |
| 82 | 286–289 | $C_{14}H_{10}Cl_2N_4O_2S$ |
| 83 | 227–229.5 | $C_{20}H_{18}N_4$ |
| 84 | 223–224 | $C_{20}H_{16}N_4$ |
| 85 | 257–258, dec. | $C_{20}H_{16}N_4$ |
| 86 | 218–219.5 | $C_{18}H_{14}N_4S$ |
| 87 | 217–219 | $C_{18}H_{14}N_4OS$ |
| 88 | 235–237 | $C_{18}H_{14}N_4S$ |
| 89 | 312–314 | $C_{18}H_{14}N_4OS$ |
| 90 | 300–302 | $C_{18}H_{14}N_4O_2S$ |
| 91 | 234–235 | $C_{18}H_{18}ClN_5O_3$ |
| 92 | 115–117 | $C_{19}H_{24}ClN_5O_4$ |
| 93 | 95–210 | $C_{21}H_{29}N_5O_6$ |
| 94 | 195, dec. | $C_{19}H_{23}Cl_2N_5O_5$ |
| 95 | 147–148.5 | $C_{21}H_{25}N_5O_5$ |
| 96 | 204 | $C_{20}H_{25}ClN_5O_5$ |
| 97 | 70–72 | $C_{22}H_{27}N_5O_5$ |
| 98 | 205, dec. | $C_{21}H_{27}Cl_2N_5O_5$ |
| 99 | 120–125 | $C_{23}H_{29}N_5O_5$ |
| 100 | 190–191 | $C_{22}H_{26}ClN_5O_5$ |
| 101 | 210, dec. | $C_{21}H_{27}Cl_2N_5O_5$ |
| 102 | 169–171 | $C_{23}H_{29}N_5O_5$ |
| 103 | 223–225 | $C_8H_6F_2N_4$ |
| 104 | 265–267 | $C_8H_6ClFN_4$ |
| 105 | 295, dec. | $C_8H_6ClFN_4$ |
| 106 | 240–245 | $C_{14}H_{11}ClN_4$ |
| 107 | 277–278 | $C_{16}H_{16}N_4$ |
| 108 | 282–285 | $C_{18}H_{20}N_4$ |
| 109 | 235–237 | $C_{15}H_{11}F_3N_4$ |
| 110 | 207 | $C_{15}H_{14}N_4O$ |
| 111 | 203–206 | $C_{16}H_{13}F_3N_4O$ |
| 112 | >250 | $C_{15}H_{14}N_4$ |
| 113 | 225–229 | $C_{15}H_{13}ClN_4$ |
| 114 | >250 | $C_{15}H_{13}ClN_4$ |
| 115 | >250 | $C_{15}H_{13}FN_4$ |
| 116 | >250 | $C_{15}H_{12}Cl_2N_4$ |
| 117 | >250 | $C_{15}H_{12}ClFN_4$ |
| 118 | >250 | $C_{16}H_{16}N_4$ |
| 119 | >250 | $C_{16}H_{16}N_4$ |
| 120 | >250 | $C_{17}H_{18}N_4$ |
| 121 | 239–241 | $C_{16}H_{15}ClN_4O$ |
| 122 | >250 | $C_{17}H_{18}N_4$ |
| 123 | >250 | $C_{18}H_{20}N_4$ |
| 124 | 208–210 | $C_{16}H_{13}F_3N_4$ |
| 125 | 224–226 | $C_{16}H_{13}F_3N_4$ |
| 126 | 232–235 | $C_{16}H_{13}F_3N_4$ |
| 127 | 185–190 | $C_{19}H_{13}F_3N_4$ |
| 128 | >250 | $C_{17}H_{18}N_4O$ |
| 129 | >250 | $C_{18}H_{20}N_4O$ |
| 130 | >250 | $C_{18}H_{20}N_4O$ |
| 131 | 238–244 | $C_{17}H_{18}N_4O$ |
| 132 | >250 | $C_{16}H_{13}F_3N_4O$ |
| 133 | 265–270 | $C_{16}H_{13}N_5$ |
| 134 | >250 | $C_{15}H_{13}N_5O_2$ |
| 135 | 279–283 | $C_{16}H_{15}N_5O$ |
| 136 | >250 | $C_{19}H_{21}N_5O$ |
| 137 | 274–275 | $C_{16}H_{17}N_5O_2S$ |
| 138 | 263–268 | $C_{21}H_{18}N_4$ |
| 139 | 197–201 | $C_{17}H_{18}N_4$ |
| 140 | 209–212 | $C_{18}H_{17}F_3N_4$ |
| 141 | 122–123 | $C_{19}H_{16}F_6N_4$ |
| 142 | >300 | $C_{17}H_{15}ClN_4$ |
| 143 | >300 | $C_{18}H_{14}ClF_3N_4$ |
| 144 | >350 | $C_{19}H_{13}ClF_6N_4$ |
| 145 | 293–295 | $C_{13}H_{12}N_4S$ |
| 146 | 270–272 | $C_{13}H_{11}ClN_4S$ |
| 147 | 258–260 | $C_{14}H_{14}N_4S$ |
| 148 | 202–204 | $C_{16}H_{10}F_6N_4$ |
| 149 | — | $C_{15}H_{12}N_4O$ |
| 150 | — | $C_{15}H_{11}ClN_4O$ |
| 151 | — | $C_{15}H_{11}ClN_4O$ |
| 152 | — | $C_{15}H_{10}Cl_2N_4O$ |
| 153 | — | $C_{15}H_{10}Cl_2N_4O$ |
| 154 | — | $C_{15}H_{11}ClN_4O$ |
| 155 | — | $C_{16}H_{11}F_3N_4O$ |
| 156 | — | $C_{16}H_{11}F_3N_4O$ |
| 157 | — | $C_{17}H_{10}F_6N_4O$ |
| 158 | — | $C_{16}H_{11}F_3N_4O$ |
| 159 | — | $C_{17}H_{14}N_4O_3$ |
| 160 | — | $C_{15}H_{11}FN_4O$ |
| 161 | — | $C_{17}H_{14}N_4O_3$ |
| 162 | — | $C_{15}H_{11}FN_4O$ |
| 163 | — | $C_{15}H_{11}FN_4O$ |
| 164 | — | $C_{15}H_{10}F_2N_4O$ |
| 165 | — | $C_{15}H_{11}FN_4O$ |
| 166 | — | $C_{15}H_{11}FN_4O$ |
| 167 | — | $C_{15}H_9F_3N_4O$ |
| 168 | — | $C_{21}H_{15}FN_4O$ |
| 169 | — | $C_{21}H_{15}ClN_4O$ |
| 170 | — | $C_{22}H_{15}F_3N_4O$ |
| 171 | — | $C_{21}H_{15}FN_4O$ |
| 172 | — | $C_{21}H_{15}ClN_4O$ |
| 173 | — | $C_{22}H_{15}F_3N_4O$ |
| 174 | 238–240, dec. | $C_{16}H_{13}Cl_2N_5O$ |
| 175 | 248–250, dec. | $C_{16}H_{12}Cl_3N_5O$ |
| 176 | — | $C_{17}H_{13}F_3N_4O_2$ |
| 177 | — | $C_{18}H_{15}F_3N_4O_2$ |
| 178 | — | $C_{15}H_{12}F_2N_4$ |
| 179 | 315–320, dec. | $C_{18}H_{19}F_3N_4O_3S$ |
| 180 | 257–262 | $C_{16}H_{16}N_4S$ |
| 181 | 248 | $C_{17}H_{18}N_4S$ |
| 182 | 325–330 | $C_{18}H_{14}ClF_3N_4$ |
| 183 | 314–320, Dec. | $C_{17}H_{19}ClN_4O_3S$ |
| 184 | 279 | $C_{17}H_{18}N_4O_2S$ |
| 185 | 188–192 | $C_{19}H_{22}N_4S$ |
| 186 | 235–237 | $C_{19}H_{22}N_4O_2S$ |
| 187 | 252–254 | $C_{16}H_{15}ClN_4O$ |
| 188 | 225–226 | $C_{16}H_{12}F_4N_4$ |
| 189 | >350 | $C_{17}H_{13}F_3N_4O$ |
| 190 | 245–248 | $C_{21}H_{18}N_4$ |
| 191 | — | $C_{21}H_{17}ClN_4$ |
| 192 | >250 | $C_{21}H_{16}F_2N_4$ |
| 193 | >250 | $C_{21}H_{16}F_2N_4$ |
| 194 | — | $C_{22}H_{17}F_3N_4$ |
| 195 | >230 | $C_{21}H_{17}ClN_4$ |
| 196 | — | $C_{21}H_{17}FN_4$ |
| 197 | 195–199 | $C_{22}H_{17}F_3N_4$ |
| 198 | 197–200 | $C_{21}H_{16}ClFN_4$ |
| 199 | 198–200 | $C_{21}H_{16}F_2N_4$ |

TABLE 1-a-continued

Melting Points and Empirical Formulas of Compounds of Table 1

| COMPOUND | MELTING POINT (°C.) | EMPIRICAL FORMULA |
|---|---|---|
| 200 | — | $C_{22}H_{20}N_4$ |
| 201 | 260 | $C_{22}H_{19}ClN_4$ |
| 202 | 257 | $C_{22}H_{19}FN_4$ |
| 203 | — | $C_{22}H_{19}F_3N_4$ |
| 204 | 217 | $C_{21}H_{18}N_4O$ |
| 205 | 202 | $C_{21}H_{17}ClN_4O$ |
| 206 | 209 | $C_{21}H_{17}FN_4O$ |
| 207 | 217–218 | $C_{21}H_{16}F_2N_4O$ |
| 208 | 240–244 | $C_{19}H_{20}N_4O$ |
| 209 | 207–210 | $C_{19}H_{20}N_4O$ |
| 210 | 257–263 | $C_{19}H_{19}ClN_4O$ |
| 211 | 259–262 | $C_{19}H_{19}ClN_4O$ |
| 212 | — | $C_{19}H_{18}N_4O_2$ |
| 213 | 242–246 | $C_{15}H_{11}F_3N_4$ |
| 214 | 224–225 | $C_{17}H_{11}F_7N_4$ |
| 215 | Oil | $C_{21}H_{16}F_6N_4O_2$ |
| 216 | 225–226 | $C_{27}H_{28}F_6N_4O_2$ |
| 217 | >250 | $C_{27}H_{28}F_6N_4O_4$ |
| 218 | 251–252 | $C_{17}H_{16}F_2N_4$ |
| 219 | 212–214 | $C_{19}H_{16}F_6N_4$ |
| 220 | — | $C_{23}H_{23}N_5OS$ |
| 221 | — | $C_{16}H_{14}FN_5O_2$ |
| 222 | — | $C_{17}H_{16}FN_5O_2$ |
| 223 | — | $C_{20}H_{22}N_4O$ |
| 224 | — | $C_{20}H_{19}F_3N_4O$ |
| 225 | 254–256 | $C_{20}H_{22}N_4O$ |
| 226 | 256–260 | $C_{20}H_{19}F_3N_4O$ |
| 227 | — | $C_{19}H_{17}ClN_4O_2$ |
| 228 | — | $C_{20}H_{20}N_4O_2$ |
| 229 | — | $C_{20}H_{17}F_3N_4O_2$ |
| 230 | — | $C_{19}H_{18}N_4O_2$ |
| 231 | 268–270 | $C_{19}H_{17}ClN_4O_2$ |
| 232 | — | $C_{20}H_{20}N_4O_2$ |
| 233 | — | $C_{20}H_{17}F_3N_4O_2$ |
| 234 | 130–135 | $C_{18}H_{18}N_4O_2$ |
| 235 | 235–238 | $C_{18}H_{17}ClN_4O_2$ |
| 236 | 207–210 | $C_{18}H_{17}FN_4O_2$ |
| 237 | — | $C_{19}H_{20}N_4O_2$ |
| 238 | — | $C_{19}H_{17}F_3N_4O_2$ |
| 239 | 224–229 | $C_{19}H_{19}FN_4O$ |
| 240 | 275 DEC | $C_{19}H_{20}N_4O_2$ |
| 241 | 307–310 | $C_{20}H_{22}N_4O_2$ |
| 242 | 226–228 | $C_{14}H_{11}ClN_4O$ |
| 243 | 218–220 | $C_{14}H_{11}ClN_4O$ |
| 244 | >200 | $C_{16}H_{10}F_6N_4O$ |
| 245 | 158–160 | $C_{15}H_{11}F_3N_4O$ |
| 246 | >220 | $C_{14}H_{10}Cl_2N_4O$ |
| 247 | — | $C_{14}H_{11}ClN_4O$ |
| 248 | — | $C_{15}H_{11}F_3N_4O$ |
| 249 | — | $C_{15}H_{11}F_3N_4O$ |
| 250 | — | $C_{14}H_{10}Cl_2N_4O$ |
| 251 | 240–245 | $C_{25}H_{28}Cl_2N_4O_2$ |
| 252 | 145–150 | $C_{23}H_{10}Cl_2F_{14}N_4O_2$ |
| 253 | 135–140 | $C_{27}H_{32}Cl_2N_4O_2$ |
| 254 | 173–176 | $C_{21}H_{10}Cl_2F_{10}N_4O_2$ |
| 255 | 121–124 | $C_{33}H_{44}Cl_2N_4O_2$ |
| 256 | >200 | $C_{23}H_{24}Cl_2N_4O_2$ |
| 257 | 101 | $C_{39}H_{56}Cl_2N_4O_2$ |
| 258 | 177–180 | $C_{19}H_{16}Cl_2N_4O_2$ |
| 259 | SOLID | $C_{29}H_{18}Cl_4N_4O_2$ |
| 260 | 187–189 | $C_{31}H_{20}F_6N_4O_2$ |
| 261 | 011 | $C_{35}H_{44}F_6N_4O_2$ |
| 262 | 216–217 | $C_{25}H_{24}F_6N_4O_2$ |
| 263 | 85–90 | $C_{23}H_{10}F_{16}N_4O_2$ |
| 264 | SOLID | $C_{25}H_{24}F_6N_4O_4$ |
| 265 | 158–159 | $C_{29}H_{32}F_6N_4O_2$ |
| 266 | 152–153 | $C_{27}H_{28}F_6N_4O_4$ |
| 267 | OIL | $C_{31}H_{36}F_6N_4O_8$ |
| 268 | — | $C_{25}H_{16}F_6N_4O_2$ |
| 269 | — | $C_{23}H_{20}F_6N_4O_6S_2$ |
| 270 | 76–78 | $C_{29}H_{32}F_6N_4O_6$ |
| 271 | — | $C_{31}H_{36}F_6N_4O_6$ |
| 272 | 208–210 | $C_{23}H_{22}F_6N_6$ |
| 273 | — | $C_{31}H_{38}F_6N_6$ |
| 274 | — | $C_{29}H_{30}F_6N_6$ |
| 275 | — | $C_{17}H_{13}F_6N_4 \cdot HCl$ |
| 276 | 164–166 DEC | $C_{17}H_{13}F_6N_4 \cdot C_6H_{11}O_7$ |
| 277 | — | $C_{17}H_{13}F_6N_4 \cdot C_2H_5SO_3H$ |
| 278 | — | $C_{17}H_{13}F_6N_4 \cdot 2C_{23}H_{16}O_6$ |
| 279 | — | $C_{15}H_{13}ClN_4O$ |
| 280 | — | $C_{15}H_{13}ClN_4O$ |
| 281 | >200 C | $C_{15}H_{13}ClN_4O$ |
| 282 | — | $C_{16}H_{13}F_3N_4O$ |
| 283 | — | $C_{16}H_{13}F_3N_4O$ |
| 284 | — | $C_{16}H_{13}F_3N_4O$ |

Insecticide Formulations

In the normal use of the insecticidal quinazolines of the present invention, they usually will not be employed free from admixture or dilution, but ordinarily will be used in a suitable formulated composition compatible with the method of application and comprising an insecticidally effective amount of the quinazoline. The quinazolines of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present quinazolines may be applied, for example, as sprays, dusts, or granules to the area where pest control is desired, the type of application varying of course with the pest and the environment. Thus, the quinazolines of this invention may be formulated as granules of large particle size, as powdery dusts, as wettable powders, as emulsifiable concentrates, as solutions, and the like. It will be understood that the insecticides themselves may be present as essentially pure compounds, or as mixtures of these quinazoline compounds.

Granules may comprise porous or nonporous particles, such as attapulgite clay or sand, for example, which serve as carriers for the quinazolines. The granule particles are relatively large, a diameter of about 400–2500 microns typically. The particles are either impregnated with the quinazoline from solution or coated with the quinazoline, adhesive sometimes being employed. Granules generally contain 0.05–10%, preferably 0.5–5%, active ingredient as the insecticidally effective amount.

Dusts are admixtures of the quinazolines with finely divided solids such as talc, attapulgite clay, kieselguhr, pyrophyllite, chalk, diatomaceous earths, calcium phosphates, calcium and magnesium carbonates, sulfur, flours, and other organic and inorganic solids which acts carriers for the insecticide. These finely divided solids have an average particle size of less than about 50 microns. A typical dust formulation useful for controlling insects contains 1 part of 2,4-diamino-5-methyl-6-[3,5-di(trifluoromethyl)phenyl]quinazoline (Compound 63) and 99 parts of talc.

The quinazolines of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% quinazoline, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

By way of illustration, compound 63 was formulated as a 10% wettable powder (10% WP) as follows:

| COMPONENT | AMOUNT (wt/wt) |
|---|---|
| Compound 63 | 10.1% |
| Wetting Agent | 5.0% |
| Dispersing Agent | 3.8% |
| Wetting/Dispersing Agent | 0.9% |
| Diluent | 80.2% |

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the quinazolines with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts, including fatty methyl taurides; alkylaryl polyether alcohols; sulfates of higher alcohols; polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal composition.

Other useful formulations include simple solutions of the active ingredient in a solvent in which it is completely soluble at the desired concentrations, such as acetone or other organic solvents.

As shown in the biological test methods below, the compounds of the present invention were tested in the laboratory as dimethylsulfoxide solutions incorporated into an artificial insect diet or as aqueous acetone or methanol solutions containing a small amount of octylphenoxypolyethoxyethanol surfactant for use as foliar sprays. An insecticidally effective amount of quinazoline in an insecticidal composition diluted for application is normally in the range of about 0.001% to about 8% by weight. Many variations of spraying and dusting compositions known in the art may be used by substituting the quinazoline of this invention into compositions known or apparent in the art.

The insecticidal compositions of this invention may be formulated with other active ingredients, including other insecticides, nematicides, acaricides, fungicides, plant growth regulators, fertilizers, etc.

In using the compositions to control insects, it is only necessary that an insecticidally effective amount of quinazoline be applied to the locus where control is desired. Such locus may, e.g., be the insects themselves, plants upon which the insects feed, or the insect habitat. When the locus is the soil, e.g., soil in which agricultural crops are or will be planted, the active compound may be applied to and optionally incorporated into the soil. For most applications, an insecticidally effective amount will be about 75 to 4000 g per hectare, preferably 150 g to 3000 g per hectare.

Biological Data

The substituted 2,4-diaminoquinazolines of the present invention were incorporated into an artificial diet for evaluation of insecticidal activity against the tobacco budworm (*Heliothis virescens* [Fabricius]).

Stock solution s of test chemical in dimethyl sulfoxide were prepa red for each rate of application. The rates of application, expressed as the negative log of the mol ar con centration, and the corresponding concentrations of the stock solution prepared for each rate are shown below:

| Stock Solution | Rate of Application |
|---|---|
| 50 micromolar | 4 |
| 5 | 5 |
| 0.5 | 6 |
| 0.05 | 7 |
| 0.005 | 8 |

One hundred microliters of each of the stock solutions was manually stirred into 50 mL of a molten (65°–70° C.) wheat germ-based artificial diet. The 50 mL of molten diet containing the test chemical was poured evenly into twenty wells in the outer four rows of a twenty-five well, five row plastic tray. Each well in the tray was about 1 cm in depth, with an opening of 3 cm by 4 cm at the lip. Molten diet containing only dimethyl sulfoxide at the levels used in the test chemical-treated diet was poured into the five wells in the third row of the tray. Each tray therefore contained one test chemical at a single rate of application, together with an untreated control.

Single second instar tobacco budworm larvae were placed in each well. The larvae were selected at a stage of growth at which they uniformly weigh about 5 mg each. Upon completion of infestation, a sheet of clear plastic was heat-sealed over the top of the tray using a common household flat iron. The trays were held at 25° C. at 60% relative humidity for five days in a growth chamber. Lighting was set at 14 hours of light and 10 hours of darkness.

After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($pI_{50}$) was determined by linear regression, when possible, for each test chemical. Where possible, the negative log of the concentration of the test chemical that provided 50% mortality ($pLC_{50}$) was also determined.

Generally, the compounds of the present invention inhibited the growth of tobacco budworm. Amongst the most efficacious compounds were Compounds 51–53, 61, 63, 66, 113, 115–117, 125, 128, 129, 143, and 178–182 with $pI_{50}$ values of greater than 6.3. Compounds 53, 63, and 129, were highly active compounds with $pI_{50}$ values of greater than 6.7 All of the compounds exemplified above caused some insect mortality in this test. These data are presented in Table 2.

Certain substituted-2,4-diaminoquinazoline derivatives with high $pI_{50}$ values from the diet test were tested for insecticidal activity in foliar evaluations against the tobacco budworm, beet armyworm (*Spodoptera exigua* Hubner]), and the cabbage looper (*Trichoplusia ni* [Hubner]).

In these tests against the tobacco budworm and the beet armyworm, nine-day-old chick pea plants (*Cicer arietinum*)

were sprayed at 20 psi to runoff on both upper and lower leaf surfaces with solutions of test chemical to provide application rates as high as 1000 ppm of test chemical. The solvent used to prepare the solutions of test chemical was 10% acetone or methanol (v/v) and 0.1% of the surfactant octylphenoxypolyethoxyethanol in distilled water. Four replicates, each containing four chick pea plants, for each rate of application of test chemical were sprayed. The treated plants were transferred to a hood where they were kept until the spray had dried.

The four chick pea plants in each replicate treated with test chemical as described above were removed from their pots by cutting the stems just above the soil line. The excised leaves and stems from the four plants in each replicate were placed in individual 8-ounce paper cups, which contained a moistened filter paper. Five second-instar (4–5 days old) tobacco budworms or beet armyworms were counted into each cup, taking care not to cause injury. An opaque plastic lid was placed on each cup, which was then held in a growth chamber for a 96 hour exposure period at 25° C. and 50% relative humidity. At the end of the 96 hour exposure period the cups were opened, and the numbers of dead and live insects were counted. Moribund larvae which were disoriented or unable to crawl normally were counted as dead. Using the insect counts, the efficacy of the test chemical was expressed in percent mortality. The condition of the test plants was also observed for phytotoxicity and for reduction of feeding damage as compared to an untreated control. Where applicable, computer-generated $LC_{50}$ values were determined from the percentages of insect mortality.

Foliar tests with cabbage looper were conducted in the same manner as described above, the difference being that pinto bean plants (*Phaseolus vulgaris*) were used.

Of the compounds evaluated on foliage for insecticidal activity, the more active ones included Compounds 63, 113, 116, 143, 178, 183, 188, 207, 208, 210, 218, 219, 225, 226, 235, 239, 256, and 258 of Table 1.

TABLE 2

Insecticidal Activity of Substituted-2,4-diaminoquinazolines Incorporated into the Diet of Tobacco Budworm

| Cmpd. No. | Rate of Application[1] | Percent Growth Inhibition[2,3,4] | $pI_{50}$[5] | Percent Mortality[6] | $pLC_{50}$[7] |
|---|---|---|---|---|---|
| 2 | 8 | ND | <4.0 | 0 | — |
|  | 7 | ND |  | 0 |  |
|  | 6 | -20 |  | 0 |  |
|  | 5 | -11 |  | 0 |  |
|  | 4 | 33 |  | 20 |  |
| 3 | 4 | 7 | — | 0 | — |
| 4 | 5 | 13 | — | 0 | — |
| 5 | 5 | -14 | <4.0 | 0 | — |
| 8 | 4 | 21 | <4.0 | 0 | — |
| 9 | 4 | 5 | — | 0 | — |
| 10 | 4 | 1 | — | 0 | — |
| 11 | 4 | -3 | — | 0 | — |
| 12 | 4 | -12 | — | 0 | — |
| 13 | 4 | -4 | — | 0 | — |
| 14 | 4 | -18 | — | 0 | — |
| 16 | 4 | 5 | — | 0 | — |
| 17 | 4 | -15 | — | 0 | — |
| 19 | 4 | -8 | — | 0 | — |
| 20 | 7 | ND | 4.5 | 0 | — |
|  | 6 | 9 |  | 0 |  |
|  | 5 | 15 |  | 0 |  |
|  | 4 | 84 |  | 15 |  |
| 21 | 4 | 23 | <4.0 | 0 | — |
| 22 | 4 | -2 | — | 0 | — |
| 25 | 7 | ND | — | 0 | — |
|  | 6 | ND |  | 0 |  |

TABLE 2-continued

Insecticidal Activity of Substituted-2,4-diaminoquinazolines Incorporated into the Diet of Tobacco Budworm

| Cmpd. No. | Rate of Application[1] | Percent Growth Inhibition[2,3,4] | $pI_{50}$[5] | Percent Mortality[6] | $pLC_{50}$[7] |
|---|---|---|---|---|---|
|  | 5 | 7 |  | 0 |  |
|  | 4 | 12 |  | 0 |  |
| 26 | 4 | 17 | — | 0 | — |
| 27 | 5 | 14 | — | 0 | — |
|  | 4 | 20 |  | 0 |  |
| 28 | 4 | 12 | — | 0 | — |
| 29 | 4 | -7 | — | 0 | — |
| 30 | 4 | 42 | <4.0 | 0 | — |
| 31 | 4 | 8 | — | 0 | — |
| 33 | 4 | 13 | — | 0 | — |
| 34 | 4 | 31 | <4.0 | 0 | — |
| 36 | 4 | 7 | — | 0 | — |
| 37 | 4 | 23 | <4.0 | 0 | — |
| 38 | 4 | -4 | — | 0 | — |
| 39 | 4 | TRACE | — | 0 | — |
| 40 | 4 | 9 | — | 0 | — |
| 41 | 4 | 4 | — | 0 | — |
| 42 | 6 | -4 | — | 0 | — |
|  | 5 | 10 |  | 0 |  |
|  | 4 | 17 |  | 0 |  |
| 45 | 6 | -2 | 4.9 | 0 | — |
|  | 5 | 56 |  | 0 |  |
|  | 4 | 82 |  | 0 |  |
| 46 | 5 | 4 | 4.4 | 0 | — |
|  | 4 | 82 |  | 0 |  |
| 47 | 7 | 20 | 5.0 | 0 | — |
|  | 6 | 15 |  | 0 |  |
|  | 5 | 54 |  | 0 |  |
|  | 4 | 84 |  | 0 |  |
| 48 | 8 | 20 | 6.3 | 0 | — |
|  | 7 | 26 |  | 0 |  |
|  | 6 | 63 |  | 10 |  |
|  | 5 | 93 |  | 50 |  |
|  | 4 | 100 |  | 85 |  |
| 49 | 7 | -6 | 6.1 | 0 | 4.5 |
|  | 6 | 63 |  | 5 |  |
|  | 5 | 98 |  | 45 |  |
|  | 4 | 97 |  | 60 |  |
| 50 | 7 | -5 | 5.3 | 0 | <4.0 |
|  | 6 | 23 |  | 0 |  |
|  | 5 | 68 |  | 10 |  |
|  | 4 | 93 |  | 40 |  |
|  | 8 | 1 | 5.8 | 0 | <4.0 |
|  | 7 | 0 |  | 0 |  |
|  | 6 | 47 |  | 0 |  |
|  | 5 | 83 |  | 20 |  |
|  | 4 | 92 |  | 30 |  |
| 51 | 7 | 7 | 6.5 | 0 | 5.6 |
|  | 6 | 88 |  | 20 |  |
|  | 5 | 99 |  | 90 |  |
|  | 4 | 100 |  | 95 |  |
|  | 8 | 5 | 6.8 | 0 | 5.4 |
|  | 7 | 25 |  | 0 |  |
|  | 6 | 87 |  | 35 |  |
|  | 5 | 97 |  | 65 |  |
|  | 4 | 99 |  | 85 |  |
| 52 | 7 | -8 | 6.4 | 0 | <4.0 |
|  | 6 | 93 |  | 10 |  |
|  | 5 | 95 |  | 25 |  |
|  | 4 | 97 |  | 45 |  |
|  | 7 | 32 | 6.7 | 0 | 5.8 |
|  | 6 | 93 |  | 30 |  |
|  | 5 | 100 |  | 95 |  |
|  | 4 | 100 |  | 95 |  |
| 53 | 7 | 46 | 6.9 | 10 | 5.6 |
|  | 6 | 90 |  | 25 |  |
|  | 5 | 100 |  | 95 |  |
|  | 4 | 100 |  | 95 |  |
| 54 | 7 | 9 | 6.1 | 0 | <4.0 |
|  | 6 | 64 |  | 5 |  |
|  | 5 | 94 |  | 25 |  |
|  | 4 | 96 |  | 35 |  |
| 55 | 4 | 21 | <4.0 | 0 | — |

TABLE 2-continued

Insecticidal Activity of Substituted-2,4-diaminoquinazolines Incorporated into the Diet of Tobacco Budworm

| Cmpd. No. | Rate of Application[1] | Percent Growth Inhibition[2,3,4] | $pI_{50}$[5] | Percent Mortality[6] | $pLC_{50}$[7] |
|---|---|---|---|---|---|
| 56 | 4 | 6 | — | 0 | — |
| 58 | 4 | 16 | — | 0 | — |
| 59 | 4 | 24 | <4.0 | 0 | — |
| 60 | 7 | 7 | 6.1 | 0 | 4.6 |
|  | 6 | 63 |  | 5 |  |
|  | 5 | 95 |  | 25 |  |
|  | 4 | 99 |  | 75 |  |
| 61 | 8 | 9 | 6.7 | 0 | <4.0 |
|  | 7 | 49 |  | 0 |  |
|  | 6 | 78 |  | 5 |  |
|  | 5 | 92 |  | 10 |  |
|  | 4 | 96 |  | 35 |  |
|  | 8 | −6 | 6.5 | 0 | 4.0 |
|  | 7 | 36 |  | 0 |  |
|  | 6 | 79 |  | 15 |  |
|  | 5 | 96 |  | 20 |  |
|  | 4 | 99 |  | 50 |  |
| 62 | 5 | 32 | 4.2 | 0 | — |
|  | 4 | 54 |  | 0 |  |
| 63 | 7 | 5 | 5.9 | 0 | — |
|  | 6 | 41 |  | 0 |  |
|  | 5 | 86 |  | 0 |  |
|  | 4 | 96 |  | 15 |  |
|  | 7 | 81 | >7.0 | 55 | >7.0 |
|  | 6 | 94 |  | 60 |  |
|  | 5 | 100 |  | 95 |  |
|  | 4 | 100 |  | 95 |  |
| 64 | 6 | −2 | 4.8 | 0 | — |
|  | 5 | 34 |  | 0 |  |
|  | 4 | 93 |  | 0 |  |
| 65 | 5 | 6 | — | 0 | — |
|  | 4 | 3 |  | 5 |  |
| 66 | 7 | 36 | 6.7 | 0 | — |
|  | 6 | 82 |  | 0 |  |
|  | 5 | 92 |  | 0 |  |
|  | 4 | 97 |  | 20 |  |
|  | 8 | 2 | 6.5 | 0 | <4.0 |
|  | 7 | 19 |  | 0 |  |
|  | 6 | 84 |  | 0 |  |
|  | 5 | 94 |  | 0 |  |
|  | 4 | 98 |  | 35 |  |
|  | 8 | 7 | 6.7 | 0 | <4.0 |
|  | 7 | 24 |  | 0 |  |
|  | 6 | 83 |  | 0 |  |
|  | 5 | 94 |  | 5 |  |
|  | 4 | 99 |  | 45 |  |
| 67 | 6 | 16 | 5.0 | 0 | — |
|  | 5 | 46 |  | 0 |  |
|  | 4 | 86 |  | 10 |  |
| 68 | 6 | 0 | 5.0 | 0 | <4.0 |
|  | 5 | 53 |  | 0 |  |
|  | 4 | 94 |  | 35 |  |
|  | 6 | 3 | 4.9 | 0 | <4.0 |
|  | 5 | 44 |  | 0 |  |
|  | 4 | 94 |  | 25 |  |
| 69 | 6 | 34 | 5.2 | 0 | — |
|  | 5 | 50 |  | 0 |  |
|  | 4 | 86 |  | 5 |  |
| 70 | 6 | 15 | 5.5 | 0 | 4.3 |
|  | 5 | 85 |  | 0 |  |
|  | 4 | 99 |  | 75 |  |
| 71 | 6 | −8 | 4.7 | 0 | — |
|  | 5 | 48 |  | 0 |  |
|  | 4 | 70 |  | 0 |  |
|  | 6 | 5 | 4.3 | 0 | — |
|  | 5 | 9 |  | 0 |  |
|  | 4 | 65 |  | 0 |  |
| 72 | 6 | 1 | 5.1 | 0 | — |
|  | 5 | 72 |  | 0 |  |
|  | 4 | 95 |  | 25 |  |
| 73 | 6 | 58 | — | 0 | — |
|  | 5 | 89 |  | 5 |  |
|  | 4 | 95 |  | 10 |  |
|  | 7 | 7 | 6.1 | 0 | — |
|  | 6 | 71 |  | 0 |  |
|  | 5 | 91 |  | 0 |  |
|  | 4 | 94 |  | 15 |  |
| 74 | 7 | 3 | 5.0 | 0 | — |
|  | 6 | 6 |  | 0 |  |
|  | 5 | 59 |  | 0 |  |
|  | 4 | 87 |  | 5 |  |
| 75 | 5 | 14 | <4.0 | 0 | — |
|  | 4 | 34 |  | 0 |  |
| 76 | 4 | 16 | — | 0 | — |
| 77 | 6 | 3 | 4.4 | 0 | <4.0 |
|  | 5 | 13 |  | 0 |  |
|  | 4 | 75 |  | 30 |  |
| 78 | 6 | 27 | 4.6 | 0 | — |
|  | 5 | 33 |  | 0 |  |
|  | 4 | 63 |  | 0 |  |
| 79 | 5 | 14 | 4.1 | 0 | — |
|  | 4 | 56 |  | 0 |  |
| 80 | 5 | 30 | 4.7 | 0 | — |
|  | 4 | 89 |  | 20 |  |
| 81 | 6 | −7 | 4.7 | 0 | — |
|  | 5 | 28 |  | 0 |  |
|  | 4 | 91 |  | 20 |  |
| 82 | 8 | 23 | 5.8 | 5 | 4.9 |
|  | 7 | 15 |  | 0 |  |
|  | 6 | 28 |  | 0 |  |
|  | 5 | 84 |  | 40 |  |
|  | 4 | 97 |  | 95 |  |
|  | 7 | 12 | 5.5 | 0 | 4.0 |
|  | 6 | 11 |  | 0 |  |
|  | 5 | 87 |  | 5 |  |
|  | 4 | 97 |  | 50 |  |
| 83 | 6 | 9 | 4.7 | 0 | — |
|  | 5 | 25 |  | 0 |  |
|  | 4 | 77 |  | 5 |  |
| 84 | 6 | 19 | 4.3 | 0 | — |
|  | 5 | 20 |  | 0 |  |
|  | 4 | 56 |  | 5 |  |
| 85 | 4 | −6 | — | 0 | — |
| 86 | 6 | 16 | <4.0 | 0 | — |
|  | 5 | 15 |  | 0 |  |
|  | 4 | 30 |  | 0 |  |
| 87 | 4 | −6 | — | 0 | — |
| 88 | 6 | −28 | 4.8 | 0 | — |
|  | 5 | 47 |  | 0 |  |
|  | 4 | 88 |  | 15 |  |
|  | 6 | 15 | 5.0 | 0 | — |
|  | 5 | 46 |  | 0 |  |
|  | 4 | 85 |  | 10 |  |
| 89 | 6 | 19 | 5.0 | 0 | — |
|  | 5 | 49 |  | 0 |  |
|  | 4 | 87 |  | 0 |  |
| 90 | 7 | 23 | 5.3 | 0 | — |
|  | 6 | 26 |  | 0 |  |
|  | 5 | 69 |  | 0 |  |
|  | 4 | 84 |  | 10 |  |
| 91 | 6 | 39 | 4.7 | 0 | — |
|  | 5 | 36 |  | 0 |  |
|  | 4 | 88 |  | 10 |  |
| 92 | 7 | 14 | 5.8 | 0 | — |
|  | 6 | 27 |  | 0 |  |
|  | 5 | 82 |  | 0 |  |
|  | 4 | 93 |  | 15 |  |
| 93 | 6 | 3 | 4.8 | 0 | — |
|  | 5 | 39 |  | 5 |  |
|  | 4 | 85 |  | 10 |  |
| 94 | 4 | 2 | — | 0 | — |
| 95 | 4 | 13 | — | 0 | — |
| 96 | 4 | −3 | — | 0 | — |
| 97 | 4 | 29 | <4.0 | 0 | — |
| 98 | 4 | 7 | — | 0 | — |
| 99 | 4 | −7 | — | 0 | — |

TABLE 2-continued

Insecticidal Activity of Substituted-2,4-diaminoquinazolines Incorporated into the Diet of Tobacco Budworm

| Cmpd. No. | Rate of Application[1] | Percent Growth Inhibition[2,3,4] | $pI_{50}$[5] | Percent Mortality[6] | $pLC_{50}$[7] |
|---|---|---|---|---|---|
| 100 | 5 | −6 | <4.0 | 0 | — |
|  | 4 | 33 |  | 0 |  |
| 101 | 4 | 17 | — | 0 | — |
| 102 | 4 | 14 | — | 0 | — |
| 106 | 5 | −1 | 4.3 | 0 | — |
|  | 4 | 71 |  | 0 |  |
| 107 | 6 | 2 | 5.0 | 0 | — |
|  | 5 | 57 |  | 0 |  |
|  | 4 | 85 |  | 5 |  |
| 108 | 7 | 6 | 4.6 | 0 | — |
|  | 6 | 20 |  | 0 |  |
|  | 5 | 28 |  | 0 |  |
|  | 4 | 79 |  | 0 |  |
| 109 | 6 | −3 | 4.7 | 0 | — |
|  | 5 | 68 |  | 5 |  |
|  | 4 | 92 |  |  |  |
| 110 | 5 | 1 | <4.0 | 0 | — |
|  | 4 | 43 |  | 5 |  |
| 111 | 5 | 5 | 4.3 | 0 | — |
|  | 4 | 68 |  | 10 |  |
| 112 | 6 | 24 | 5.6 | 0 | <4.0 |
|  | 5 | 85 |  | 20 |  |
|  | 4 | 97 |  | 25 |  |
| 113 | 7 | 17 | 6.5 | 0 | 5.2 |
|  | 6 | 86 |  | 10 |  |
|  | 5 | 98 |  | 60 |  |
|  | 4 | 98 |  | 55 |  |
| 114 | 6 | 10 | 5.2 | 0 | 4.2 |
|  | 5 | 69 |  | 25 |  |
|  | 4 | 97 |  | 55 |  |
| 115 | 7 | 28 | 6.4 | 0 | 4.4 |
|  | 6 | 68 |  | 5 |  |
|  | 5 | 97 |  | 35 |  |
|  | 4 | 99 |  | 60 |  |
| 116 | 7 | 27 | 6.4 | 0 | 5.4 |
|  | 6 | 65 |  | 5 |  |
|  | 5 | 99 |  | 80 |  |
|  | 4 | 100 |  | 95 |  |
| 117 | 7 | 29 | 6.4 | 0 | 4.5 |
|  | 6 | 70 |  | 0 |  |
|  | 5 | 95 |  | 20 |  |
|  | 4 | 100 |  | 75 |  |
| 118 | 7 | 23 | 6.1 | 0 | — |
|  | 6 | 48 |  | 0 |  |
|  | 5 | 92 |  | 0 |  |
|  | 4 | 96 |  | 15 |  |
| 119 | 6 | 10 | 4.7 | 0 | — |
|  | 5 | 39 |  | 0 |  |
|  | 4 | 75 |  | 15 |  |
| 121 | 7 | 6 | 6.2 | 0 | 4.6 |
|  | 6 | 76 |  | 0 |  |
|  | 5 | 97 |  | 35 |  |
|  | 4 | 99 |  | 70 |  |
| 122 | 6 | 40 | 5.8 | 0 | — |
|  | 5 | 96 |  | 20 |  |
|  | 4 | 89 |  | 20 |  |
| 123 | 7 | 21 | 6.2 | 0 | <4.0 |
|  | 6 | 59 |  | 0 |  |
|  | 5 | 91 |  | 5 |  |
|  | 4 | 97 |  | 40 |  |
|  | 7 | 0 | 6.0 | 0 | — |
|  | 6 | 61 |  | 0 |  |
|  | 5 | 91 |  | 0 |  |
|  | 4 | 97 |  | 5 |  |
| 124 | 6 | 7 | — | 0 | <4.0 |
|  | 5 | 96 |  | 25 |  |
|  | 4 | 97 |  | 35 |  |
|  | 8 | −16 | 6.2 | 0 | 4.5 |
|  | 7 | 21 |  | 0 |  |
|  | 6 | 62 |  | 5 |  |
|  | 5 | 92 |  | 25 |  |
|  | 4 | 99 |  | 70 |  |
| 125 | 8 | 17 | 6.9 | 0 | 5.5 |
|  | 7 | 37 |  | 0 |  |
|  | 6 | 89 |  | 10 |  |
|  | 5 | 100 |  | 85 |  |
|  | 4 | 100 |  | 90 |  |
| 126 | 6 | −5 | 5.0 | 0 | — |
|  | 5 | 57 |  | 0 |  |
|  | 4 | 96 |  | 20 |  |
| 127 | 6 | 69 | >6.0 | 0 | <4.0 |
|  | 5 | 94 |  | 20 |  |
|  | 4 | 96 |  | 40 |  |
|  | 7 | 5 | 6.2 | 0 | 4.7 |
|  | 6 | 77 |  | 10 |  |
|  | 5 | 96 |  | 40 |  |
|  | 4 | 99 |  | 70 |  |
| 128 | 7 | 22 | 6.6 | 5 | 4.6 |
|  | 6 | 85 |  | 15 |  |
|  | 5 | 96 |  | 25 |  |
|  | 4 | 99 |  | 70 |  |
| 129 | 7 | 44 | 6.8 | 0 | <4.0 |
|  | 6 | 76 |  | 15 |  |
|  | 5 | 97 |  | 25 |  |
|  | 4 | 98 |  | 45 |  |
| 130 | 5 | 6 | 4.4 | 0 | — |
|  | 4 | 76 |  | 10 |  |
| 131 | 7 | 2 | 5.9 | 0 | — |
|  | 6 | 54 |  | 0 |  |
|  | 5 | 85 |  | 0 |  |
|  | 4 | 94 |  | 20 |  |
| 132 | 7 | −8 | 6.0 | 0 | 4.4 |
|  | 6 | 60 |  | 15 |  |
|  | 5 | 92 |  | 25 |  |
|  | 4 | 99 |  | 70 |  |
| 133 | 7 | −1 | 5.8 | 0 | 4.0 |
|  | 6 | 31 |  | 5 |  |
|  | 5 | 91 |  | 20 |  |
|  | 4 | 96 |  | 50 |  |
| 134 | 6 | 13 | 5.3 | 0 | <4.0 |
|  | 5 | 78 |  | 5 |  |
|  | 4 | 98 |  | 35 |  |
| 135 | 6 | −6 | 4.9 | 0 | — |
|  | 5 | 52 |  | 0 |  |
|  | 4 | 90 |  | 15 |  |
| 136 | 6 | 4 | 4.9 | 0 | <4.0 |
|  | 5 | 47 |  | 10 |  |
|  | 4 | 91 |  | 30 |  |
| 137 | 6 | 1 | 4.8 | 0 | <4.0 |
|  | 5 | 33 |  | 0 |  |
|  | 4 | 85 |  | 25 |  |
| 139 | 6 | 7 | 4.7 | 0 | — |
|  | 5 | 32 |  | 0 |  |
|  | 4 | 80 |  | 10 |  |
| 140 | 5 | 15 | 4.5 | 5 | — |
|  | 4 | 89 |  | 20 |  |
| 141 | 5 | 33 | 4.7 | 0 | — |
|  | 4 | 88 |  | 5 |  |
| 142 | 8 | 15 | 6.2 | 0 | <4.0 |
|  | 7 | 10 |  | 0 |  |
|  | 6 | 71 |  | 5 |  |
|  | 5 | 93 |  | 5 |  |
|  | 4 | 97 |  | 40 |  |
| 143 | 7 | 40 | 6.8 | 0 | <4.0 |
|  | 6 | 93 |  | 0 |  |
|  | 5 | 95 |  | 0 |  |
|  | 4 | 95 |  | 30 |  |
| 144 | 6 | −7 | 5.1 | 0 | — |
|  | 5 | 75 |  | 0 |  |
|  | 4 | 94 |  | 15 |  |
| 145 | 6 | 21 | 5.3 | 0 | — |
|  | 5 | 70 |  | 5 |  |
|  | 4 | 94 |  | 5 |  |
| 146 | 7 | 0 | 6.0 | 0 | <4.0 |
|  | 6 | 60 |  | 0 |  |
|  | 5 | 89 |  | 20 |  |

TABLE 2-continued

Insecticidal Activity of Substituted-2,4-diaminoquinazolines Incorporated into the Diet of Tobacco Budworm

| Cmpd. No. | Rate of Application[1] | Percent Growth Inhibition[2,3,4] | $pI_{50}$[5] | Percent Mortality[6] | $pLC_{50}$[7] |
|---|---|---|---|---|---|
| 147 | 4 | 97 | | 40 | |
|  | 6 | 5 | 5.2 | 0 | — |
|  | 5 | 77 | | 0 | |
|  | 4 | 91 | | 5 | |
| 148 | 6 | 7 | 4.9 | 0 | — |
|  | 5 | 43 | | 0 | |
|  | 4 | 84 | | 0 | |
| 149 | 7 | 18 | 6.3 | 0 | <4.0 |
|  | 6 | 69 | | 10 | |
|  | 5 | 95 | | 25 | |
|  | 4 | 97 | | 30 | |
| 150 | 7 | 0 | 6.6 | 0 | <4.0 |
|  | 6.5 | 65 | | 0 | |
|  | 6 | 71 | | 15 | |
|  | 5 | 91 | | 20 | |
|  | 4 | 96 | | 25 | |
| 155 | 7 | 17 | 6.1 | 0 | — |
|  | 6 | 60 | | 0 | |
|  | 5 | 88 | | 5 | |
|  | 4 | 94 | | 10 | |
| 156 | 6 | 14 | 5.2 | 0 | — |
|  | 5 | 66 | | 0 | |
|  | 4 | 94 | | 5 | |
| 158 | 6 | 15 | 5.2 | 0 | — |
|  | 5 | 68 | | 0 | |
|  | 4 | 91 | | 5 | |
| 181 | 8 | 2 | 6.5 | 0 | <4.0 |
|  | 7 | 24 | | 0 | |
|  | 6 | 73 | | 5 | |
|  | 5 | 96 | | 5 | |
|  | 4 | 97 | | 25 | |
| 182 | 8 | 11 | 6.4 | 0 | — |
|  | 7 | 25 | | 0 | |
|  | 6 | 63 | | 0 | |
|  | 5 | 92 | | 0 | |
|  | 4 | 95 | | 5 | |
| 183 | 7 | 31 | 6.6 | 0 | 4.9 |
|  | 6 | 82 | | 15 | |
|  | 5 | 97 | | 35 | |
|  | 4 | 100 | | 85 | |
| 184 | 7 | -3 | 5.9 | 0 | — |
|  | 6 | 43 | | 0 | |
|  | 5 | 92 | | 15 | |
|  | 4 | 95 | | 20 | |
| 185 | 7 | 7 | 6.2 | 0 | 3.9 |
|  | 6 | 72 | | 20 | |
|  | 5 | 95 | | 25 | |
|  | 4 | 98 | | 50 | |
| 186 | 7 | 30 | 6.1 | 0 | — |
|  | 6 | 47 | | 0 | |
|  | 5 | 86 | | 5 | |
|  | 4 | 96 | | 10 | |
|  | 7 | 9 | 6.1 | 0 | <4.0 |
|  | 6 | 65 | | 0 | |
|  | 5 | 92 | | 0 | |
|  | 4 | 96 | | 25 | |
|  | 7 | 14 | 5.9 | 0 | — |
|  | 6 | 35 | | 0 | |
|  | 5 | 88 | | 10 | |
|  | 4 | 95 | | 15 | |
| 187 | 7 | 0 | 5.6 | 0 | — |
|  | 6 | 23 | | 0 | |
|  | 5 | 80 | | 10 | |
|  | 4 | 93 | | 10 | |
| 188 | 7 | 49 | 7.0 | 0 | 5.1 |
|  | 6 | 89 | | 30 | |
|  | 4 | 99 | | 70 | |
| 189 | 6 | -8 | 4.5 | 0 | <4.0 |
|  | 5 | 19 | | 0 | |
|  | 4 | 79 | | 25 | |
| 190 | 7 | 24 | 6.3 | 0 | — |
|  | 6 | 65 | | 10 | |
|  | 5 | 93 | | 0 | |
|  | 4 | 96 | | 15 | |
| 191 | 7 | 42 | 6.8 | 0 | <4.0 |
|  | 6 | 85 | | 10 | |
|  | 5 | 95 | | 10 | |
|  | 4 | 97 | | 40 | |
| 192 | 7 | 15 | 6.5 | 5 | 5.1 |
|  | 6 | 86 | | 20 | |
|  | 5 | 98 | | 60 | |
|  | 4 | 100 | | 75 | |
| 193 | 7 | 16 | 6.2 | 0 | <4.0 |
|  | 6 | 64 | | 0 | |
|  | 5 | 90 | | 20 | |
|  | 4 | 96 | | 30 | |
| 194 | 7 | 19 | 6.3 | 0 | <4.0 |
|  | 6 | 76 | | 5 | |
|  | 5 | 92 | | 15 | |
|  | 4 | 97 | | 25 | |
| 195 | 7 | -3 | 6.1 | 0 | 4.9 |
|  | 6 | 67 | | 5 | |
|  | 5 | 96 | | 45 | |
|  | 4 | 98 | | 90 | |
| 196 | 7 | 57 | — | 0 | 4.8 |
|  | 6 | 90 | | 15 | |
|  | 5 | 95 | | 30 | |
|  | 4 | 100 | | 85 | |
|  | 9 | 1 | 7.1 | 0 | 5.2 |
|  | 8 | 19 | | 0 | |
|  | 7 | 54 | | 0 | |
|  | 6 | 88 | | 15 | |
|  | 5 | 98 | | 70 | |
|  | 4 | 99 | | 90 | |
| 197 | 6 | 7 | 5.2 | 0 | <4.0 |
|  | 5 | 77 | | 10 | |
|  | 4 | 96 | | 30 | |
| 198 | 7 | -2 | 6.4 | 0 | 5.5 |
|  | 6 | 92 | | 15 | |
|  | 5 | 100 | | 80 | |
|  | 4 | 100 | | 90 | |
| 199 | 8 | 7 | 7.1 | 0 | 5.1 |
|  | 7 | 67 | | 0 | |
|  | 6 | 93 | | 20 | |
|  | 5 | 98 | | 60 | |
|  | 4 | 100 | | 75 | |
| 200 | 7 | -4 | 5.3 | 0 | — |
|  | 6 | 26 | | 0 | |
|  | 5 | 64 | | 0 | |
|  | 4 | 88 | | 5 | |
| 201 | 7 | -6 | 5.6 | 0 | 4.8 |
|  | 6 | 15 | | 0 | |
|  | 5 | 93 | | 25 | |
|  | 4 | 97 | | 95 | |
| 202 | 8 | 8 | 6.2 | 0 | 4.4 |
|  | 7 | 18 | | 0 | |
|  | 6 | 66 | | 5 | |
|  | 5 | 95 | | 30 | |
|  | 4 | 97 | | 65 | |
| 203 | 6 | 6 | 4.5 | 0 | — |
|  | 5 | 15 | | 0 | |
|  | 4 | 82 | | 15 | |
| 204 | 8 | 4 | 6.8 | 0 | 4.8 |
|  | 7 | 34 | | 0 | |
|  | 6 | 84 | | 10 | |
|  | 5 | 98 | | 55 | |
|  | 4 | 98 | | 70 | |
| 205 | 7 | 83 | — | 10 | — |
|  | 6 | 97 | | 65 | |
|  | 5 | 100 | | 90 | |
|  | 4 | 100 | | 95 | |
|  | 8 | 12 | 7.2 | 0 | 6.2 |
|  | 7 | 71 | | 15 | |
|  | 6 | 99 | | 70 | |
|  | 5 | 99 | | 90 | |
|  | 4 | 99 | | 95 | |

TABLE 2-continued

Insecticidal Activity of Substituted-2,4-diaminoquinazolines Incorporated into the Diet of Tobacco Budworm

| Cmpd. No. | Rate of Application[1] | Percent Growth Inhibition[2,3,4] | $pI_{50}$[5] | Percent Mortality[6] | $pLC_{50}$[7] |
|---|---|---|---|---|---|
| 206 | 7 | 11 | 6.2 | 0 | <4.0 |
|  | 6 | 74 |  | 10 |  |
|  | 5 | 95 |  | 15 |  |
|  | 4 | 97 |  | 25 |  |
| 207 | 8 | 8 | 7.0 | 0 | <4.0 |
|  | 7 | 52 |  | 0 |  |
|  | 6 | 92 |  | 10 |  |
|  | 5 | 96 |  | 10 |  |
|  | 4 | 96 |  | 40 |  |
| 208 | 7 | 39 | 6.8 | 0 | <4.0 |
|  | 6 | 91 |  | 15 |  |
|  | 5 | 96 |  | 15 |  |
|  | 4 | 98 |  | 30 |  |
| 209 | 7 | 68 | — | 0 | — |
|  | 6 | 71 |  | 0 |  |
|  | 5 | 85 |  | 10 |  |
|  | 4 | 96 |  | 20 |  |
|  | 9 | −1 | 6.7 | 0 | — |
|  | 8 | 22 |  | 0 |  |
|  | 7 | 37 |  | 0 |  |
|  | 6 | 70 |  | 0 |  |
|  | 5 | 87 |  | 0 |  |
|  | 4 | 96 |  | 5 |  |
| 210 | 9 | −4 | 7.0 | 0 | 5.5 |
|  | 8 | 8 |  | 0 |  |
|  | 7 | 55 |  | 10 |  |
|  | 6 | 92 |  | 25 |  |
|  | 5 | 100 |  | 75 |  |
|  | 4 | 100 |  | 85 |  |
| 211 | 7 | 14 | 6.2 | 0 | <4.0 |
|  | 6 | 69 |  | 0 |  |
|  | 5 | 90 |  | 5 |  |
|  | 4 | 97 |  | 40 |  |
| 213 | 7 | −4 | 6.4 | 0 | 5.2 |
|  | 6 | 80 |  | 15 |  |
|  | 5 | 97 |  | 65 |  |
|  | 4 | 100 |  | 95 |  |
| 214 | 8 | −3 | 6.8 | 0 | 5.8 |
|  | 7 | 33 |  | 0 |  |
|  | 6 | 90 |  | 25 |  |
|  | 5 | 100 |  | 95 |  |
|  | 4 | 100 |  | 100 |  |
| 215 | 7 | 2 | 6.4 | 0 | 5.1 |
|  | 6 | 88 |  | 25 |  |
|  | 5 | 98 |  | 50 |  |
|  | 4 | 100 |  | 80 |  |
| 216 | 6 | −10 | 4.8 | 0 | <4.0 |
|  | 5 | 37 |  | 0 |  |
|  | 4 | 90 |  | 45 |  |
| 217 | 7 | 1 | 6.1 | 0 | 4.3 |
|  | 6 | 73 |  | 0 |  |
|  | 5 | 95 |  | 20 |  |
|  | 4 | 97 |  | 60 |  |
| 218 | 7 | 8 | 6.5 | 0 | 5.6 |
|  | 6 | 87 |  | 20 |  |
|  | 5 | 100 |  | 90 |  |
|  | 4 | 100 |  | 95 |  |
| 219 | 7 | 43 | 6.9 | 5 | 5.9 |
|  | 6 | 96 |  | 45 |  |
|  | 5 | 100 |  | 90 |  |
|  | 4 | 100 |  | 95 |  |
| 220 | 7 | −4 | 5.5 | 0 | 4.1 |
|  | 6 | 24 |  | 0 |  |
|  | 5 | 76 |  | 15 |  |
|  | 4 | 97 |  | 55 |  |
| 221 | 4 | 2 | — | 0 | — |
| 222 | 5 | 3 | 4.4 | 0 | — |
|  | 4 | 79 |  | 15 |  |
| 225 | 7 | 9 | 6.5 | 0 | <4.0 |
|  | 6 | 84 |  | 0 |  |
|  | 5 | 97 |  | 30 |  |
|  | 4 | 99 |  | 30 |  |
| 226 | 7 | 50 | >7.0 | 0 | 47 |
|  | 6 | 91 |  | 25 |  |
|  | 5 | 96 |  | 35 |  |
|  | 4 | 99 |  | 70 |  |
|  | 9 | 9 | 7.4 | 0 | 5.4 |
|  | 8 | 32 |  | 0 |  |
|  | 7 | 56 |  | 0 |  |
|  | 6 | 91 |  | 15 |  |
|  | 5 | 99 |  | 70 |  |
| 231 | 6 | 2 | 5.1 | 0 |  |
|  | 5 | 71 |  | 10 |  |
|  | 4 | 91 |  | 20 |  |
| 234 | 7 | 27 | 6.6 | 0 |  |
|  | 6 | 89 |  | 0 |  |
|  | 5 | 95 |  | 5 |  |
|  | 4 | 97 |  | 15 |  |
| 235 | 7 | 64 | ~7.0 | 0 | 5.5 |
|  | 6 | 94 |  | 15 |  |
|  | 5 | 100 |  | 90 |  |
|  | 4 | 100 |  | 100 |  |
|  | 8 | 29 | 7.3 | 0 | 6.0 |
|  | 7 | 52 |  | 10 |  |
|  | 6 | 97 |  | 55 |  |
|  | 5 | 100 |  | 85 |  |
| 236 | 7 | 43 | 6.9 | 0 | 5.3 |
|  | 6 | 91 |  | 10 |  |
|  | 5 | 99 |  | 65 |  |
|  | 4 | 99 |  | 70 |  |
| 239 | 7 | 40 | 6.8 | 0 | 4.2 |
|  | 6 | 88 |  | 15 |  |
|  | 5 | 95 |  | 25 |  |
|  | 4 | 99 |  | 55 |  |
| 240 | 6 | 6 | 4.4 | 0 |  |
|  | 5 | 14 |  | 0 |  |
|  | 4 | 70 |  | 10 |  |
| 241 | 7 | 14 | 5.8 | 0 |  |
|  | 6 | 36 |  | 0 |  |
|  | 5 | 82 |  | 0 |  |
|  | 4 | 95 |  | 5 |  |
| 242 | 6 | 15 | 4.5 | 0 |  |
|  | 5 | 25 |  | 0 |  |
|  | 4 | 75 |  | 0 |  |
| 243 | 5 | 1 | 4.0 | 0 |  |
|  | 4 | 49 |  | 0 |  |
| 244 | 5 | 1 | 4.1 | 0 |  |
|  | 4 | 55 |  | 5 |  |
| 245 | 5 | 6 | 4.1 | 0 |  |
|  | 4 | 54 |  | 0 |  |
| 246 | 5 | 11 | 4.5 | 0 | <4.0 |
|  | 4 | 90 |  | 45 |  |
| 251 | 6 | 0 | 5.1 | 0 |  |
|  | 5 | 68 |  | 5 |  |
|  | 4 | 82 |  | 10 |  |
| 252 | 7 | 38 | 6.8 | 0 | 4.6 |
|  | 6 | 89 |  | 10 |  |
|  | 5 | 97 |  | 40 |  |
|  | 4 | 100 |  | 65 |  |
| 253 | 8 | 14 | 6.5 | 0 | 5.7 |
|  | 7 | 5 |  | 0 |  |
|  | 6 | 94 |  | 35 |  |
|  | 5 | 100 |  | 80 |  |
|  | 4 | 100 |  | 85 |  |
|  | 8 | −10 | 6.5 | 0 | 4.9 |
|  | 7 | 6 |  | 0 |  |
|  | 6 | 92 |  | 0 |  |
|  | 5 | 100 |  | 30 |  |
|  | 4 | 100 |  | 100 |  |
| 254 | 7 | 18 | 6.6 | 0 | 5.5 |
|  | 6 | 92 |  | 35 |  |
|  | 5 | 99 |  | 75 |  |
|  | 4 | 100 |  | 95 |  |
| 255 | 5 | 99 | >5.0 | 0 | 4.4 |
|  | 4 | 100 |  | 85 |  |
|  | 7 | 7 | 6.4 | 0 | 5.3 |

TABLE 2-continued

Insecticidal Activity of Substituted-2,4-diaminoquinazolines Incorporated into the Diet of Tobacco Budworm

| Cmpd. No. | Rate of Application[1] | Percent Growth Inhibition[2,3,4] | $pI_{50}$[5] | Percent Mortality[6] | $pLC_{50}$[7] |
|---|---|---|---|---|---|
|  | 6 | 83 |  | 10 |  |
|  | 5 | 98 |  | 65 |  |
|  | 4 | 100 |  | 75 |  |
| 256 | 6 | 95 | >6.0 | 0 | 5.3 |
|  | 5 | 99 |  | 75 |  |
|  | 4 | 100 |  | 80 |  |
|  | 8 | −1 | 6.9 | 0 | 5.6 |
|  | 7 | 43 |  | 0 |  |
|  | 6 | 95 |  | 25 |  |
|  | 5 | 98 |  | 80 |  |
| 257 | 5 | 80 | >5.0 | 15 | <4.0 |
|  | 4 | 93 |  | 25 |  |
|  | 6 | 1 | 5.3 | 0 | <4.0 |
|  | 5 | 74 |  | 0 |  |
|  | 4 | 85 |  | 25 |  |
| 258 | 7 | 18 | 6.6 | 0 | 5.1 |
|  | 6 | 92 |  | 25 |  |
|  | 5 | 99 |  | 50 |  |
|  | 4 | 100 |  | 85 |  |
| 259 | 7 | 3 | 6.1 | 0 | 5.1 |
|  | 6 | 66 |  | 5 |  |
|  | 5 | 99 |  | 65 |  |
|  | 4 | 100 |  | 100 |  |
| 260 | 5 | 6 | 4.3 | 0 |  |
|  | 4 | 66 |  | 0 |  |
| 261 | 6 | −1 | 5.1 | 0 | 4.1 |
|  | 5 | 72 |  | 5 |  |
|  | 4 | 96 |  | 55 |  |
| 262 | 7 | 11 | 6.3 | 0 | 5.8 |
|  | 6 | 79 |  | 30 |  |
|  | 5 | 100 |  | 95 |  |
|  | 4 | 100 |  | 100 |  |
| 263 | 7 | 6 | 6.2 | 0 | 5.5 |
|  | 6 | 74 |  | 20 |  |
|  | 5 | 100 |  | 85 |  |
|  | 4 | 100 |  | 85 |  |
| 264 | 7 | 22 | 6.5 | 0 | 5.6 |
|  | 6 | 80 |  | 15 |  |
|  | 5 | 100 |  | 95 |  |
|  | 4 | 100 |  | 100 |  |
| 265 | 7 | 10 | 6.2 | 0 | 5.5 |
|  | 6 | 66 |  | 10 |  |
|  | 5 | 100 |  | 95 |  |
|  | 4 | 100 |  | 100 |  |
| 266 | 7 | 21 | 6.6 | 0 | 5.4 |
|  | 6 | 90 |  | 30 |  |
|  | 5 | 98 |  | 55 |  |
|  | 4 | 100 |  | 100 |  |
| 267 | 8 | 17 | 7.3 | 0 | 5.7 |
|  | 7 | 75 |  | 5 |  |
|  | 6 | 95 |  | 30 |  |
|  | 5 | 99 |  | 80 |  |
|  | 4 | 99 |  | 85 |  |
| 270 | 7 | 13 | 6.5 | 0 | 5.7 |
|  | 6 | 88 |  | 25 |  |
|  | 5 | 100 |  | 100 |  |
| 272 | 7 | 15 | 5.6 | 0 | 4.4 |
|  | 6 | 29 |  | 0 |  |
|  | 5 | 83 |  | 10 |  |
|  | 4 | 99 |  | 75 |  |
| 276 | 7 | 45 | 6.9 | 0 | 4.4 |
|  | 6 | 92 |  | 0 |  |
|  | 5 | 99 |  | 30 |  |
|  | 4 | 99 |  | 65 |  |
| 281 | 7 | 33 | 6.7 | 0 | 4.4 |
|  | 6 | 85 |  | 0 |  |
|  | 5 | 96 |  | 25 |  |
|  | 4 | 99 |  | 65 |  |

FOOTNOTES

[1]) The rate of application is expressed as the negative log of the molar concentration of the test compound in the diet.

[2]) Percent growth inhibition is derived from the total weight of insects (IW) at each rate of application in the test relative to the total weight of insects in an untreated control, % Gr. Inh. = $\frac{\text{IW (control)} - \text{IW (test)}}{\text{IW (control)}} \times 100$

[3]) ND = No data

[4]) A minus % growth inhibition indicates that the insects weighed more at the termination of the test than those in the untreated control.

[5]) $pI_{50}$ is the negative log of the concentration of the test chemical that provides 50% growth inhibition of the test insects.

[6]) Percent mortality is derived from the number of dead insects (ID) relative to the total number of insects (TI) used in the test, % Mortality = $\frac{\text{TI} - \text{ID}}{\text{TI}} \times 100$

[7]) $pLC_{50}$ is the negative log of the concentration of the test chemical that provides 50% mortality of the test insects.

TABLE 3

Insecticidal Activity of 2,4-diaminoquinazolines Applied as Foliar Sprays

| | Rate of | Percent Mortality | | |
|---|---|---|---|---|
| Cmpd No. | Application (ppm) | TBW | BAW | CL[(1)] |
| 7 | 300 | 0 | | |
|  | 100 | 0 | | |
|  | 30 | 0 | | |
|  | 10 | 0 | | |
|  | 3 | 0 | | |
| 47 | 3000 | 80 | 100 | 85 |
|  | 1000 | 75 | 70 | 50 |
|  | 300 | 16 | 20 | 35 |
|  | 100 | 5 | 5 | 30 |
|  | 30 | 5 | 0 | 20 |
| 48 | 300 | 90 | 95 | 32 |
|  | 100 | 53 | 74 | 15 |
|  | 30 | 6 | 5 | 0 |
|  | 10 | 5 | 5 | 0 |
| 49 | 1000 | 100 | 100 | 100 |
|  | 300 | 100 | 100 | 100 |
|  | 100 | 95 | 100 | 100 |
|  | 30 | 85 | 35 | 65 |
|  | 10 | 32 | 5 | 40 |
| 50 | 1000 | 65 | 100 | 100 |
|  | 300 | 44 | 95 | 95 |
|  | 100 | 16 | 90 | 89 |
|  | 30 | 16 | 50 | 5 |
| 51 | 300 | 100 | 100 | 100 |
|  | 100 | 90 | 100 | 68 |
|  | 30 | 80 | 95 | 20 |
|  | 10 | 47 | 10 | 5 |
| 52 | 1000 | 100 | 100 | 100 |
|  | 300 | 100 | 100 | 100 |
|  | 100 | 95 | 100 | 100 |
|  | 30 | 85 | 90 | 95 |
|  | 10 | 44 | 20 | 45 |
| 53 | 1000 | 100 | 100 | 85 |
|  | 300 | 100 | 100 | 85 |
|  | 100 | 95 | 100 | 75 |
|  | 30 | 85 | 90 | 35 |
|  | 10 | 30 | 30 | 10 |
| 54 | 1000 | 100 | 100 | 100 |
|  | 300 | 100 | 100 | 95 |
|  | 100 | 55 | 90 | 35 |
|  | 30 | 32 | 40 | 28 |
|  | 10 | 5 | 5 | 11 |
| 60 | 1000 | 100 | 100 | 45 |
|  | 300 | 100 | 90 | 20 |
|  | 100 | 95 | 40 | 5 |
|  | 30 | 89 | 5 | 10 |

TABLE 3-continued

Insecticidal Activity of 2,4-diaminoquinazolines Applied as Foliar Sprays

| Cmpd No. | Rate of Application (ppm) | Percent Mortality TBW | BAW | CL[1] |
|---|---|---|---|---|
| | 10 | 24 | 0 | 15 |
| 61 | 1000 | 100 | 100 | 65 |
| | 300 | 100 | 100 | 35 |
| | 100 | 100 | 85 | 35 |
| | 30 | 94 | 70 | 5 |
| | 10 | 95 | 10 | 15 |
| 63 | 3000 | 100 | 100 | 100 |
| | 1000 | 100 | 100 | 100 |
| | 300 | 100 | 100 | 95 |
| | 100 | 100 | 95 | 100 |
| | 30 | 95 | 85 | 95 |
| 66 | 1000 | 95 | 100 | 100 |
| | 300 | 90 | 100 | 100 |
| | 100 | 90 | 100 | 100 |
| | 30 | 40 | 100 | 74 |
| | 10 | 11 | 40 | 75 |
| 67 | 3000 | 17 | 26 | 25 |
| | 1000 | 5 | 10 | 5 |
| | 300 | 5 | 5 | 0 |
| | 100 | 0 | 0 | 0 |
| | 30 | 5 | 0 | 11 |
| 68 | 3000 | 0 | 10 | 10 |
| | 1000 | 0 | 5 | 6 |
| | 300 | 5 | 0 | 0 |
| | 100 | 0 | 0 | 11 |
| | 30 | 0 | 0 | 5 |
| 69 | 3000 | 5 | 45 | 25 |
| | 1000 | 0 | 0 | 11 |
| | 300 | 0 | 0 | 5 |
| | 100 | 0 | 0 | 10 |
| | 30 | 0 | 0 | 0 |
| 70 | 3000 | 0 (11) | 0 (0) | 10 (32) |
| | 1000 | 0 (0) | 0 (5) | 15 (25) |
| | 300 | 0 (10) | 0 (0) | 10 (20) |
| | 100 | 0 (0) | 0 (0) | 0 (20) |
| | 30 | 5 (0) | 0 (0) | 11 (21) |
| 71 | 1000 | 5 | 0 | 15 |
| | 300 | 0 | 0 | 21 |
| | 100 | 0 | 0 | 10 |
| | 30 | 0 | 0 | 5 |
| | 10 | 5 | 0 | 15 |
| 72 | 3000 | (70) | | (80) |
| | 1000 | 21 (63) | 0 | 45 (35) |
| | 300 | 6 (5) | 0 | 15 (17) |
| | 100 | 5 (0) | 0 | 5 (10) |
| | 30 | 0 (0) | 0 | 5 (10) |
| | 10 | 0 | 0 | 10 |
| 73 | 3000 | 100 | 100 | 95 |
| | 1000 | 100 | 100 | 75 |
| | 300 | 80 | 90 | 47 |
| | 100 | 47 | 50 | 45 |
| | 30 | 10 | 5 | 26 |
| 74 | 3000 | 25 | 16 | 15 |
| | 1000 | 5 | 0 | 5 |
| | 300 | 0 | 0 | 15 |
| | 100 | 5 | 0 | 15 |
| | 30 | 0 | 0 | 5 |
| 80 | 1000 | 90 | | |
| | 300 | 58 | | |
| | 100 | 0 | | |
| 82 | 1000 | 100 | | |
| | 300 | 95 | | |
| | 100 | 90 | | |
| | 30 | 39 | | |
| | 10 | 7 | | |
| | 3 | 0 | | |
| 88 | 1000 | 95 | | |
| | 300 | 40 | | |
| | 100 | 5 | | |
| 90 | 1000 | 0 | | |
| | 300 | 0 (35) | | |
| | 100 | 0 (0) | | |
| | 30 | (0) | | |
| | 10 | (0) | | |
| | 3 | (0) | | |
| 92 | 3000 | 100 | 10 | 58 |
| | 1000 | 100 | 0 | 37 |
| | 300 | 90 | 0 | 26 |
| | 100 | 30 | 0 | 30 |
| | 30 | 5 | 0 | 11 |
| 93 | 1000 | 20 | 0 | 25 |
| | 300 | 0 | 0 | 15 |
| | 100 | 0 | 0 | 16 |
| | 30 | 10 | 0 | 11 |
| | 10 | 0 | 0 | 5 |
| 107 | 3000 | 100 | 95 | 100 |
| | 1000 | 95 | 78 | 79 |
| | 300 | 53 | 21 | 45 |
| | 100 | 5 | 5 | 10 |
| | 30 | 0 | 10 | 5 |
| 108 | 3000 | 53 | 95 | 75 |
| | 1000 | 17 | 50 | 26 |
| | 300 | 5 | 5 | 10 |
| | 100 | 5 | 0 | 0 |
| | 30 | 0 | 0 | 5 |
| 109 | 3000 | 100 | 83 | 100 |
| | 1000 | 90 | 59 | 84 |
| | 300 | 84 | 10 | 85 |
| | 100 | 6 | 16 | 35 |
| | 30 | 0 | 0 | 10 |
| 111 | 3000 | 56 | 95 | 41 |
| | 1000 | 20 | 35 | 26 |
| | 300 | 17 | 5 | 5 |
| | 100 | 5 | 0 | 5 |
| | 30 | 0 | 0 | 0 |
| 112 | 1000 | 100 | 100 | 95 |
| | 300 | 100 | 5 | 75 |
| | 100 | 78 | 5 | 58 |
| | 30 | 41 | 0 | 20 |
| | 10 | 5 | 0 | 24 |
| | 1000 | | 95 | |
| | 300 | | 63 | |
| | 100 | | 30 | |
| | 30 | | 0 | |
| | 10 | | 0 | |
| 113 | 1000 | 100 | 100 | 100 |
| | 300 | 100 | 100 | 100 |
| | 100 | 100 | 95 | 94 |
| | 30 | 100 | 29 | 60 |
| | 10 | 80 | 5 | 58 |
| | 100 | 100 | | 95 |
| | 30 | 90 | | 83 |
| | 10 | 37 | | 50 |
| | 3 | 5 | | 11 |
| | 1 | 5 | | 0 |
| 114 | 3000 | 100 | 100 | 100 |
| | 1000 | 100 | 95 | 75 |
| | 300 | 95 | 85 | 90 |
| | 100 | 80 | 10 | 75 |
| | 30 | 5 | 0 | 45 |
| 115 | 1000 | 100 | 100 | 100 |
| | 300 | 100 | 90 | 85 |
| | 100 | 95 | 22 | 90 |
| | 30 | 89 | 5 | 85 |
| | 10 | 29 | 5 | 25 |
| | 1000 | | 100 | |
| | 300 | | 95 | |
| | 100 | | 50 | |
| | 30 | | 5 | |
| | 10 | | 0 | |
| 116 | 1000 | 100 | 100 | 100 |
| | 300 | 100 | 100 | 94 |
| | 100 | 95 | 95 | 95 |
| | 30 | 89 | 90 | 65 |

TABLE 3-continued

Insecticidal Activity of 2,4-diaminoquinazolines Applied as Foliar Sprays

| Cmpd No. | Rate of Application (ppm) | Percent Mortality TBW | BAW | CL[1] |
|---|---|---|---|---|
|  | 10 | 18 | 28 | 10 |
|  | 100 | 100 | 100 | 85 |
|  | 30 | 95 | 85 | 63 |
|  | 10 | 30 | 20 | 20 |
|  | 3 | 5 | 5 | 15 |
|  | 1 | 0 | 0 | 15 |
| 117 | 1000 | 100 | 100 | 100 |
|  | 300 | 100 | 100 | 90 |
|  | 100 | 95 | 95 | 90 |
|  | 30 | 75 | 60 | 84 |
|  | 10 | 40 | 5 | 58 |
|  | 100 |  |  | 90 |
|  | 30 |  |  | 100 |
|  | 10 |  |  | 100 |
|  | 3 |  |  | 15 |
|  | 1 |  |  | 0 |
| 118 | 1000 | 100 | 100 | 83 |
|  | 300 | 100 | 95 | 89 |
|  | 100 | 100 | 35 | 61 |
|  | 30 | 40 | 21 | 28 |
|  | 10 | 17 | 0 | 6 |
|  | 100 | 100 |  |  |
|  | 30 | 72 |  |  |
|  | 10 | 21 |  |  |
|  | 3 | 5 |  |  |
|  | 1 | 0 |  |  |
| 121 | 1000 | 100 | 100 | 90 |
|  | 300 | 100 | 100 | 95 |
|  | 100 | 82 | 100 | 95 |
|  | 30 | 70 | 95 | 90 |
|  | 10 | 37 | 15 | 95 |
| 122 | 1000 | 100 | 95 | 71 |
|  | 300 | 83 | 40 | 44 |
|  | 100 | 53 | 10 | 5 |
|  | 30 | 16 | 0 | 6 |
|  | 10 | 0 | 0 | 0 |
| 123 | 1000 | 80 | 90 | 70 |
|  | 300 | 89 | 55 | 55 |
|  | 100 | 55 | 30 | 30 |
|  | 30 | 20 | 5 | 0 |
|  | 10 | 5 | 0 | 5 |
| 124 | 1000 | 95 | 85 | 100 |
|  | 300 | 95 | 37 | 83 |
|  | 100 | 74 | 5 | 75 |
|  | 30 | 47 | 0 | 25 |
|  | 10 | 25 | 0 | 5 |
| 125 | 100 | 95 | 95 | 100 |
|  | 30 | 95 | 55 | 95 |
|  | 10 | 37 | 16 | 28 |
|  | 3 | 5 | 0 | 5 |
|  | 1 | 0 | 5 | 0 |
|  | 100 |  |  | 100 |
|  | 30 |  |  | 90 |
|  | 10 |  |  | 20 |
|  | 3 |  |  | 5 |
|  | 1 |  |  | 5 |
| 126 | 1000 | 100 | 95 | 90 |
|  | 300 | 80 | 79 | 90 |
|  | 100 | 16 | 5 | 37 |
|  | 30 | 5 | 0 | 10 |
|  | 10 | 5 | 0 | 5 |
|  | 300 | 100 | 70 | 100 |
|  | 100 | 70 | 5 | 85 |
|  | 30 | 24 | 0 | 85 |
|  | 10 | 11 | 0 | 47 |
|  | 3 | 0 | 0 | 20 |
|  | 100 |  |  | 100 |
|  | 30 |  |  | 95 |
|  | 10 |  |  | 72 |
|  | 3 |  |  | 30 |
|  | 1 |  |  | 0 |
| 127 | 1000 | 85 | 85 | 100 |
|  | 300 | 65 | 55 | 65 |
|  | 100 | 45 | 10 | 50 |
|  | 30 | 5 | 0 | 15 |
|  | 10 | 0 | 0 | 0 |
| 128 | 1000 | 100 | 100 | 100 |
|  | 300 | 100 | 100 | 90 |
|  | 100 | 95 | 95 | 65 |
|  | 30 | 85 | 47 | 40 |
|  | 10 | 40 | 25 | 5 |
| 129 | 1000 | 100 | 100 | 100 |
|  | 300 | 95 | 95 | 95 |
|  | 100 | 74 | 50 | 85 |
|  | 30 | 25 | 5 | 95 |
|  | 10 | 0 | 0 | 35 |
| 131 | 1000 | 100 | 85 | 95 |
|  | 300 | 95 | 75 | 95 |
|  | 100 | 95 | 20 | 70 |
|  | 30 | 60 | 0 | 40 |
|  | 10 | 5 | 0 | 20 |
| 132 | 1000 | 100 | 100 | 100 |
|  | 300 | 100 | 100 | 84 |
|  | 100 | 95 | 95 | 95 |
|  | 30 | 80 | 25 | 90 |
|  | 10 | 25 | 5 | 15 |
| 133 | 1000 | 100 | 100 | 100 |
|  | 300 | 100 | 95 | 100 |
|  | 100 | 95 | 80 | 95 |
|  | 30 | 78 | 15 | 37 |
|  | 10 | 32 | 5 | 5 |
| 134 | 3000 | 100 | 100 | 100 |
|  | 1000 | 100 | 95 | 95 |
|  | 300 | 95 | 44 | 84 |
|  | 100 | 63 | 5 | 40 |
|  | 30 | 16 | 0 | 5 |
| 135 | 1000 | 100 | 15 | 35 |
|  | 300 | 70 | 0 | 15 |
|  | 100 | 15 | 0 | 5 |
|  | 30 | 5 | 0 | 5 |
|  | 10 | 5 | 10 | 7 |
| 136 | 1000 | 29 | 0 | 58 |
|  | 300 | 10 | 0 | 5 |
|  | 100 | 0 | 5 | 15 |
|  | 30 | 0 | 5 | 15 |
|  | 10 | 0 | 0 | 10 |
| 137 | 3000 | 50 | 0 | 42 |
|  | 1000 | 0 | 0 | 20 |
|  | 300 | 0 | 0 | 0 |
|  | 100 | 0 | 5 | 10 |
|  | 30 | 0 | 0 | 10 |
| 140 | 3000 | 74 | 58 | 20 |
|  | 1000 | 56 | 15 | 5 |
|  | 300 | 5 | 15 | 5 |
|  | 100 | 0 | 10 | 0 |
|  | 30 | 0 | 0 | 0 |
| 141 | 3000 | 16 | 5 | 0 |
|  | 1000 | 10 | 10 | 0 |
|  | 300 | 11 | 0 | 0 |
|  | 100 | 0 | 0 | 10 |
|  | 30 | 0 | 0 | 0 |
| 142 | 300 | 100 | 70 | 100 |
|  | 100 | 70 | 5 | 85 |
|  | 30 | 24 | 0 | 85 |
|  | 10 | 11 | 0 | 47 |
|  | 3 | 0 | 0 | 20 |
|  | 100 |  |  | 100 |
|  | 30 |  |  | 95 |
|  | 10 |  |  | 72 |
|  | 3 |  |  | 30 |
|  | 1 |  |  | 0 |
| 143 | 1000 | 100 | 100 | 100 |
|  | 300 | 100 | 100 | 100 |
|  | 100 | 100 | 100 | 89 |

TABLE 3-continued

Insecticidal Activity of 2,4-diaminoquinazolines Applied as Foliar Sprays

| Cmpd No. | Rate of Application (ppm) | Percent Mortality TBW | BAW | CL[1] |
|---|---|---|---|---|
|  | 30 | 100 | 100 | 90 |
|  | 10 | 44 | 67 | 85 |
|  | 100 | 100 | 100 | 95 |
|  | 30 | 90 | 95 | 90 |
|  | 10 | 85 | 70 | 95 |
|  | 3 | 19 | 5 | 45 |
|  | 1 | 0 | 0 | 5 |
|  | 100 |  | 100 | 100 |
|  | 30 |  | 95 | 89 |
|  | 10 |  | 79 | 70 |
|  | 3 |  | 10 | 15 |
|  | 1 |  | 0 | 0 |
| 144 | 3000 | 11 | 40 | 65 |
|  | 1000 | 10 | 0 | 55 |
|  | 300 | 0 | 0 | 5 |
|  | 100 | 0 | 0 | 10 |
|  | 30 | 0 | 0 | 5 |
| 146 | 1000 | 95 | 95 | 90 |
|  | 300 | 94 | 70 | 85 |
|  | 100 | 90 | 5 | 20 |
|  | 30 | 89 | 0 | 5 |
|  | 10 | 0 | 0 | 0 |
| 149 | 300 | 95 | 55 | 63 |
|  | 100 | 68 | 53 | 56 |
|  | 30 | 37 | 15 | 5 |
|  | 10 | 15 | 5 | 0 |
|  | 3 | 11 | 5 | 0 |
| 175 | 1000 | 89 |  |  |
|  | 300 | 35 |  |  |
|  | 100 | 10 |  |  |
|  | 30 | 5 |  |  |
|  | 10 | 0 |  |  |
| 177 | 300 | 95 | 100 | 60 |
|  | 100 | 80 | 95 | 32 |
|  | 30 | 58 | 60 | 45 |
|  | 10 | 28 | 5 | 35 |
|  | 3 | 5 | 0 | 5 |
|  | 300 | 100 | 100 | 90 |
|  | 100 | 95 | 95 | 95 |
|  | 30 | 53 | 90 | 60 |
|  | 10 | 21 | 6 | 45 |
|  | 3 | 0 | 5 | 10 |
| 178 | 1000 | 100 | 100 | 100 |
|  | 300 | 100 | 100 | 80 |
|  | 100 | 95 | 95 | 79 |
|  | 30 | 84 | 63 | 47 |
|  | 10 | 56 | 30 | 50 |
|  | 300 |  |  | 80 |
|  | 100 | 100 |  | 75 |
|  | 30 | 100 |  | 90 |
|  | 10 | 90 |  | 90 |
|  | 3 | 32 |  | 5 |
|  | 1 | 6 |  |  |
| 179 | 100 | 100 | 95 | 100 |
|  | 30 | 65 | 63 | 95 |
|  | 10 | 53 | 5 | 40 |
|  | 3 | 5 | 0 | 10 |
|  | 1 | 0 | 0 | 0 |
| 181 | 1000 | 100 | 95 | 74 |
|  | 300 | 90 | 20 | 75 |
|  | 100 | 79 | 10 | 50 |
|  | 30 | 28 | 0 | 5 |
|  | 10 | 11 | 0 | 10 |
| 182 | 1000 | 100 | 90 | 100 |
|  | 300 | 83 | 32 | 95 |
|  | 100 | 53 | 5 | 75 |
|  | 30 | 35 | 0 | 85 |
|  | 10 | 5 | 0 | 37 |
| 183 | 1000 | 100 | 100 | 100 |
|  | 300 | 100 | 100 | 100 |
|  | 100 | 95 | 90 | 100 |
|  | 30 | 89 | 55 | 95 |
|  | 10 | 53 | 15 | 90 |
|  | 100 | 95 |  | 80 |
|  | 30 | 84 |  | 42 |
|  | 10 | 59 |  | 45 |
|  | 3 | 5 |  | 10 |
|  | 1 | 0 |  | 5 |
| 184 | 1000 | 95 | 39 | 79 |
|  | 300 | 72 | 5 | 10 |
|  | 100 | 45 | 0 | 5 |
|  | 30 | 5 | 0 | 0 |
|  | 10 | 0 | 0 | 0 |
| 185 | 1000 | 100 | 100 | 90 |
|  | 300 | 100 | 89 | 80 |
|  | 100 | 80 | 55 | 25 |
|  | 30 | 11 | 15 | 0 |
|  | 10 | 6 | 16 | 5 |
| 186 | 1000 | 100 | 75 | 89 |
|  | 300 | 72 | 20 | 55 |
|  | 100 | 67 | 5 | 11 |
|  | 30 | 35 | 0 | 10 |
|  | 10 | 5 | 0 | 0 |
| 188 | 1000 | 100 | 100 | 100 |
|  | 300 | 100 | 100 | 100 |
|  | 100 | 100 | 100 | 100 |
|  | 30 | 95 | 85 | 84 |
|  | 10 | 71 | 65 | 55 |
|  | 100 | 100 | 100 | 80 |
|  | 30 | 95 | 95 | 58 |
|  | 10 | 71 | 37 | 60 |
|  | 3 | 6 | 5 | 5 |
|  | 1 | 6 | 0 | 0 |
| 189 | 300 | 5 | 95 | 70 |
|  | 100 | 0 | 44 | 20 |
|  | 30 | 0 | 5 | 11 |
|  | 10 | 11 | 5 | 0 |
|  | 3 | 5 | 0 | 10 |
|  | 3000 | 84 |  |  |
|  | 1000 | 39 |  |  |
|  | 300 | 10 |  |  |
|  | 100 | 0 |  |  |
|  | 30 | 0 |  |  |
| 190 | 1000 | 100 | 95 | 100 |
|  | 300 | 100 | 58 | 70 |
|  | 100 | 95 | 5 | 85 |
|  | 30 | 50 | 0 | 45 |
|  | 10 | 11 | 0 | 5 |
| 191 | 3000 | 100 | 100 | 100 |
|  | 1000 | 100 | 100 | 100 |
|  | 300 | 95 | 100 | 100 |
|  | 100 | 100 | 100 | 90 |
|  | 30 | 85 | 80 | 85 |
|  | 100 | 89 | 95 | 100 |
|  | 30 | 67 | 56 | 95 |
|  | 10 | 22 | 5 | 20 |
|  | 3 | 21 | 0 | 0 |
|  | 1 | 0 | 0 | 0 |
| 192 | 300 | 100 | 100 | 100 |
|  | 100 | 95 | 95 | 95 |
|  | 30 | 30 | 42 | 74 |
|  | 10 | 5 | 5 | 40 |
|  | 3 | 5 | 0 | 5 |
| 193 | 1000 | 100 | 100 | 85 |
|  | 300 | 90 | 95 | 85 |
|  | 100 | 89 | 83 | 85 |
|  | 30 | 22 | 90 | 25 |
|  | 10 | 0 | 10 | 5 |
| 194 | 1000 | 100 | 100 | 100 |
|  | 300 | 83 | 100 | 100 |
|  | 100 | 44 | 100 | 95 |
|  | 30 | 5 | 80 | 55 |
|  | 10 | 0 | 45 | 15 |
|  | 300 | 95 | 100 | 100 |

TABLE 3-continued

Insecticidal Activity of 2,4-diaminoquinazolines Applied as Foliar Sprays

| Cmpd No. | Rate of Application (ppm) | TBW | BAW | CL[1] |
|---|---|---|---|---|
|  | 100 | 67 | 100 | 90 |
|  | 30 | 10 | 90 | 79 |
|  | 10 | 6 | 44 | 20 |
|  | 3 | 0 | 5 | 0 |
| 195 | 1000 | 95 | 47 | 15 |
|  | 300 | 61 | 26 | 20 |
|  | 100 | 11 | 15 | 15 |
|  | 30 | 0 | 0 | 10 |
|  | 10 | 0 | 0 | 5 |
| 196 | 3000 | 100 | 100 | 100 |
|  | 1000 | 100 | 100 | 100 |
|  | 300 | 100 | 100 | 80 |
|  | 100 | 100 | 100 | 65 |
|  | 30 | 83 | 53 | 75 |
|  | 100 | 95 | 95 | 95 |
|  | 30 | 80 | 6 | 35 |
|  | 10 | 5 | 5 | 11 |
|  | 3 | 0 | 0 | 0 |
|  | 1 | 6 | 0 | 5 |
| 197 | 1000 | 25 | 5 | 25 |
|  | 300 | 5 | 5 | 0 |
|  | 100 | 0 | 0 | 0 |
|  | 30 | 0 | 0 | 0 |
|  | 10 | 0 | 0 | 0 |
|  | 700 | 21 | 16 | 60 |
|  | 100 | 5 | 5 | 0 |
|  | 30 | 0 | 0 | 5 |
|  | 10 | 0 | 0 | 0 |
|  | 3 | 0 | 5 | 10 |
| 198 | 300 | 100 | 100 | 65 |
|  | 100 | 95 | 100 | 60 |
|  | 30 | 53 | 0 | 37 |
|  | 10 | 33 | 5 | 5 |
|  | 3 | 0 | 0 | 5 |
|  | 300 |  | 95 |  |
|  | 100 |  | 68 |  |
|  | 30 |  | 11 |  |
|  | 10 |  | 0 |  |
|  | 3 |  | 7 |  |
| 199 | 300 | 100 | 100 | 95 |
|  | 100 | 100 | 100 | 67 |
|  | 30 | 95 | 95 | 58 |
|  | 10 | 68 | 25 | 30 |
|  | 3 | 6 | 5 | 0 |
| 200 | 3000 | 95 | 100 | 100 |
|  | 1000 | 79 | 100 | 95 |
|  | 300 | 50 | 95 | 79 |
|  | 100 | 5 | 68 | 75 |
|  | 30 | 0 | 15 | 60 |
|  | 1000 |  |  | 100 |
|  | 300 |  |  | 95 |
|  | 100 |  |  | 95 |
|  | 30 |  |  | 80 |
|  | 10 |  |  | 55 |
|  | 100 |  |  | 75 |
|  | 30 |  |  | 75 |
|  | 10 |  |  | 25 |
|  | 3 |  |  | 20 |
|  | 1 |  |  | 15 |
| 201 | 1000 | 95 | 95 | 55 |
|  | 300 | 53 | 45 | 45 |
|  | 100 | 5 | 20 | 25 |
|  | 30 | 0 | 0 | 5 |
|  | 10 | 5 | 11 | 10 |
| 202 | 30 | 6 | 0 | 55 |
|  | 3 | 21 | 0 | 5 |
| 204 | 30 | 65 | 20 | 100 |
|  | 3 | 10 | 5 | 25 |
|  | 300 | 100 | 100 | 90 |
|  | 100 | 94 | 95 | 73 |
|  | 30 | 89 | 24 | 85 |
|  | 10 | 40 | 26 | 80 |
|  | 3 | 5 | 0 | 25 |
| 205 | 100 | 100 | 95 | 50 |
|  | 30 | 100 | 75 | 5 |
|  | 10 | 78 | 5 | 0 |
|  | 3 | 25 | 0 | 6 |
|  | 1 | 18 | 0 | 5 |
|  | 300 | 100 | 100 | 95 |
|  | 100 | 95 | 100 | 40 |
|  | 30 | 90 | 85 | 5 |
|  | 10 | 70 | 32 | 5 |
|  | 3 | 10 | 5 | 5 |
| 206 | 1000 | 100 | 100 | 94 |
|  | 300 | 89 | 100 | 85 |
|  | 100 | 90 | 100 | 26 |
|  | 30 | 53 | 100 | 25 |
|  | 10 | 11 | 60 | 35 |
| 207 | 1000 | 100 | 100 | 100 |
|  | 300 | 100 | 100 | 100 |
|  | 100 | 100 | 100 | 100 |
|  | 30 | 94 | 100 | 95 |
|  | 10 | 63 | 100 | 22 |
|  | 100 | 100 | 100 |  |
|  | 30 | 94 | 100 |  |
|  | 10 | 40 | 95 |  |
|  | 3 | 7 | 13 |  |
|  | 1 | 5 | 0 |  |
| 208 | 1000 | 100 | 100 | 100 |
|  | 300 | 100 | 100 | 100 |
|  | 100 | 95 | 100 | 90 |
|  | 30 | 80 | 95 | 70 |
|  | 10 | 35 | 55 | 80 |
|  | 300 | 100 |  |  |
|  | 100 | 100 | 100 | 100 |
|  | 30 | 95 | 79 | 80 |
|  | 10 | 59 | 25 | 70 |
|  | 3 | 11 | 5 | 5 |
|  | 1 | 0 | 5 | 0 |
|  | 300 |  | 100 | 100 |
|  | 100 | 100 | 100 | 95 |
|  | 30 | 95 | 95 | 65 |
|  | 10 | 90 | 45 | 76 |
|  | 3 | 19 | 5 | 16 |
|  | 1 | 11 | 5 | 10 |
|  | 100 |  | 100 | 95 |
|  | 30 |  | 89 | 80 |
|  | 10 |  | 26 | 85 |
|  | 3 |  | 10 | 5 |
|  | 1 |  | 0 | 0 |
| 209 | 300 | 95 | 95 | 74 |
|  | 100 | 35 | 42 | 25 |
|  | 30 | 5 | 5 | 20 |
|  | 10 | 0 | 10 | 15 |
|  | 3 | 0 | 0 | 15 |
|  | 300 | 70 | 79 | 84 |
|  | 100 | 16 | 60 | 63 |
|  | 30 | 5 | 5 | 10 |
|  | 10 | 5 | 16 | 20 |
|  | 3 | 0 | 10 | 5 |
|  | 300 | 90 | 80 | 85 |
|  | 100 | 50 | 53 | 84 |
|  | 30 | 16 | 10 | 10 |
|  | 10 | 0 | 5 | 5 |
|  | 3 | 5 | 0 | 0 |
|  | 1 | 0 | 5 | 5 |
| 210 | 100 | 95 | 100 | 84 |
|  | 30 | 100 | 100 | 95 |
|  | 10 | 50 | 95 | 95 |
|  | 3 | 21 | 50 | 70 |
|  | 1 | 5 | 5 | 22 |
|  | 100 | 100 | 100 | 95 |
|  | 30 | 90 | 100 | 95 |
|  | 10 | 71 | 95 | 80 |

TABLE 3-continued

Insecticidal Activity of 2,4-diaminoquinazolines Applied as Foliar Sprays

| Cmpd No. | Rate of Application (ppm) | Percent Mortality TBW | BAW | CL[(1)] |
|---|---|---|---|---|
|  | 3 | 29 | 25 | 80 |
|  | 1 | 0 | 5 | 5 |
| 211 | 30 | 30 | 56 | 80 |
|  | 3 | 11 | 5 | 5 |
|  | 300 | 95 | 100 | 80 |
|  | 100 | 80 | 94 | 80 |
|  | 30 | 21 | 78 | 75 |
|  | 10 | 5 | 11 | 55 |
|  | 3 | 0 | 0 | 10 |
| 213 | 300 | 100 | 95 | — |
|  | 100 | 95 | 85 | 35 |
|  | 30 | 85 | 30 | 15 |
|  | 10 | 6 | 21 | 20 |
|  | 3 | 0 | 0 | 5 |
|  | 1000 |  |  | 75 |
|  | 300 |  |  | 47 |
|  | 100 |  |  | 44 |
|  | 30 |  |  | 10 |
|  | 10 |  |  | 5 |
| 214 | 100 | 95 | 95 | 74 |
|  | 30 | 75 | 75 | 68 |
|  | 10 | 11 | 10 | 21 |
|  | 3 | 0 | 10 | 5 |
|  | 1 | 0 | 0 | 5 |
| 215 | 1000 | 100 | 100 | 100 |
|  | 300 | 100 | 100 | 100 |
|  | 100 | 95 | 95 | 90 |
|  | 30 | 69 | 65 | 37 |
|  | 10 | 7 | 10 | 5 |
| 216 | 100 | 0 | 26 | 15 |
|  | 30 | 0 | 0 | 5 |
|  | 10 | 6 | 0 | 5 |
|  | 3 | 5 | 11 | 10 |
|  | 1 | 0 | 21 | 21 |
| 217 | 1000 | 100 | 100 | 84 |
|  | 300 | 95 | 95 | 53 |
|  | 100 | 89 | 28 | 25 |
|  | 30 | 6 | 5 | 0 |
|  | 10 | 0 | 0 | 0 |
| 218 | 300 | 100 | 100 | 100 |
|  | 100 | 100 | 100 | 100 |
|  | 30 | 95 | 75 | 89 |
|  | 10 | 75 | 50 | 95 |
|  | 3 | 33 | 5 | 15 |
| 219 | 100 | 100 | 100 | 100 |
|  | 30 | 100 | 95 | 85 |
|  | 10 | 79 | 15 | 79 |
|  | 3 | 5 | 5 | 5 |
|  | 1 | 5 | 0 | 16 |
| 225 | 100 | 100 | 100 | 100 |
|  | 30 | 94 | 100 | 100 |
|  | 10 | 47 | 100 | 95 |
|  | 3 | 6 | 90 | 79 |
|  | 1 | 5 | 40 | 50 |
|  | 30 |  | 95 |  |
|  | 10 |  | 90 |  |
|  | 3 |  | 90 |  |
|  | 1 |  | 75 |  |
|  | 0.3 |  | 15 |  |
| 226 | 100 | 100 | 95 | 100 |
|  | 30 | 95 | 55 | 100 |
|  | 10 | 65 | 58 | 95 |
|  | 3 | 24 | 45 | 18 |
|  | 1 | 0 | 15 | 5 |
|  | 100 | 100 | 100 | 100 |
|  | 30 | 95 | 100 | 100 |
|  | 10 | 59 | 100 | 95 |
|  | 3 | 33 | 95 | 90 |
|  | 1 | 0 | 47 | 5 |
|  | 30 |  | 100 |  |
|  | 10 |  | 100 |  |
|  | 3 |  | 90 |  |
|  | 1 |  | 53 |  |
|  | 0.3 |  | 11 |  |
| 231 | 300 | 6 | 95 | 85 |
|  | 100 | 0 | 75 | 41 |
|  | 30 | 0 | 50 | 5 |
|  | 10 | 0 | 15 | 5 |
|  | 3 | 0 | 5 | 5 |
| 235 | 100 | 100 | 100 | 100 |
|  | 30 | 95 | 95 | 100 |
|  | 10 | 50 | 85 | 95 |
|  | 3 | 11 | 63 | 10 |
|  | 1 | 0 | 15 | 0 |
| 239 | 100 | 100 | 95 | 100 |
|  | 30 | 95 | 70 | 100 |
|  | 10 | 55 | 58 | 95 |
|  | 3 | 5 | 5 | 30 |
|  | 0 | 0 | 5 |  |
| 241 | 3000 | 100 | 90 | 100 |
|  | 1000 | 100 | 95 | 100 |
|  | 300 | 95 | 90 | 95 |
|  | 100 | 26 | 80 | 90 |
|  | 30 | 5 | 90 | 30 |
|  | 300 |  | 65 |  |
|  | 100 |  | 75 |  |
|  | 30 |  | 90 |  |
|  | 10 |  | 75 |  |
|  | 3 |  | 16 |  |
| 251 | 100 | 0 | 5 | 5 |
|  | 30 | 0 | 11 | 0 |
|  | 10 | 0 | 6 | 0 |
|  | 3 | 0 | 0 | 0 |
| 252 | 100 | 95 | 95 | 95 |
|  | 30 | 42 | 50 | 60 |
|  | 10 | 29 | 5 | 5 |
|  | 3 | 0 | 6 | 0 |
| 253 | 300 | 100 | 95 | 100 |
|  | 100 | 89 | 83 | 95 |
|  | 30 | 74 | 61 | 80 |
|  | 10 | 5 | 5 | 5 |
|  | 3 | 0 | 0 | 0 |
| 254 | 100 | 100 | 89 | 100 |
|  | 30 | 89 | 95 | 63 |
|  | 10 | 30 | 32 | 6 |
|  | 3 | 5 | 10 | 6 |
| 255 | 300 | 100 | 25 | 95 |
|  | 100 | 80 | 40 | 30 |
|  | 30 | 35 | 21 | 30 |
|  | 10 | 11 | 30 | 11 |
|  | 3 | 5 | 40 | 0 |
|  | 300 |  | 16 |  |
|  | 100 |  | 10 |  |
|  | 30 |  | 17 |  |
|  | 10 |  | 11 |  |
|  | 3 |  | 10 |  |
| 256 | 300 | 100 | 100 | 100 |
|  | 100 | 100 | 95 | 100 |
|  | 30 | 100 | 90 | 95 |
|  | 10 | 95 | 25 | 26 |
|  | 3 | 0 | 11 | 5 |
| 257 | 300 | 0 | 5 | 5 |
|  | 100 | 0 | 5 | 0 |
|  | 30 | 0 | 0 | 0 |
|  | 10 | 0 | 10 | 5 |
|  | 3 | 0 | 10 | 10 |
| 258 | 300 | 100 | 100 | 100 |
|  | 100 | 100 | 100 | 100 |
|  | 30 | 95 | 95 | 100 |
|  | 10 | 79 | 79 | 70 |
|  | 3 | 11 | 33 | 5 |
| 259 | 100 | 100 | 100 | 100 |
|  | 30 | 100 | 95 | 90 |
|  | 10 | 85 | 20 | 20 |

TABLE 3-continued

Insecticidal Activity of 2,4-diaminoquinazolines Applied as Foliar Sprays

| Cmpd No. | Rate of Application (ppm) | Percent Mortality TBW | BAW | CL[(1)] |
|---|---|---|---|---|
|  | 3 | 16 | 15 | 5 |
|  | 5 | 10 | 0 |  |
| 260 | 300 |  | 10 | 50 |
|  | 100 | 5 | 6 | 0 |
| 261 | 300 |  | 0 | 5 |
|  | 100 | 11 | 10 | 0 |
| 262 | 100 | 100 | 90 |  |
|  | 30 | 100 | 70 |  |
|  | 10 | 95 | 5 |  |
|  | 3 | 11 | 5 |  |
|  | 1 | 5 | 5 |  |
| 263 | 300 | 100 | 100 | 100 |
|  | 30 | 65 | 21 | 90 |
|  | 300 | 100 | 100 | 95 |
|  | 100 | 95 | 95 | 80 |
|  | 30 | 50 | 25 | 10 |
|  | 10 | 11 | 5 | 0 |
|  | 3 | 0 | 15 | 0 |
| 264 | 300 | 100 | 100 | 100 |
|  | 30 | 70 | 15 | 74 |
|  | 300 | 100 | 100 | 100 |
|  | 100 | 95 | 95 | 95 |
|  | 30 | 50 | 30 | 24 |
|  | 10 | 17 | 10 | 5 |
|  | 3 | 0 | 10 | 0 |
| 265 | 300 |  | 79 | 100 |
|  | 100 | 100 | 56 | 95 |
|  | 300 | 100 | 100 | 100 |
|  | 100 | 100 | 80 | 95 |
|  | 30 | 79 | 30 | 25 |
|  | 10 | 39 | 11 | 5 |
|  | 3 | 6 | 15 | 0 |
| 266 | 100 | 100 | 95 |  |
|  | 30 | 89 | 65 |  |
|  | 10 | 24 | 10 |  |
|  | 3 | 5 | 0 |  |
|  | 1 | 0 | 5 |  |
| 267 | 300 | 100 | 100 | 100 |
|  | 100 | 95 | 100 | 100 |
|  | 30 | 95 | 89 | 90 |
|  | 10 | 50 | 20 | 11 |
|  | 3 | 6 | 10 | 5 |
| 272 | 300 | 100 | 75 | 53 |
|  | 100 | 80 | 5 | 0 |
|  | 30 | 26 | 5 | 0 |
|  | 10 | 6 | 5 | 5 |
|  | 3 | 0 | 0 | 5 |
| 276 | 300 | 100 | 100 | 100 |
|  | 100 | 100 | 100 | 100 |
|  | 30 | 95 | 95 | 95 |
|  | 10 | 72 | 65 | 29 |
|  | 3 | 11 | 32 | 5 |
|  | 100 |  | 95 |  |
|  | 30 |  | 68 |  |
|  | 10 |  | 5 |  |
|  | 3 |  | 11 |  |

[(1)]TBW, BAW and Cl are, respectively, the above-described tobacco budworm, beet armyworm, and cabbage looper.

In a further embodiment of this invention, several of the intermediates disclosed above have, themselves, been found to be novel and useful compounds in the preparation of the quinazoline insecticides disclosed and claimed herein, which intermediates may be prepared by methods described as analogous to those described above or in the literature.

Included amongst these compounds are those having the following structure:

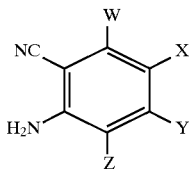

(I-A)

wherein

W is selected from hydrogen, halogen (e.g., chlorine), lower alkyl [e.g., —CH$_3$, —CH(CH$_3$)$_2$], lower haloalkyl (e.g., —CF$_3$), and lower alkoxy (e.g., —OCH$_3$)

X is selected from
(a) halogen (e.g., Br, I);
(b) substituted aryl, [e.g., phenyl] i.e., aryl substituted with one or more halogens (e.g., Cl, F), lower alkyl (e.g., —CH$_3$), lower haloalkyl (e.g., —CF$_3$), lower alkoxy (e.g., —OCH$_3$), lower alkylthio (e.g., —SC$_4$H$_9$), lower alkylsulfonyl (e.g., —SO$_2$C$_2$H$_5$, or —SO$_2$C$_4$H$_9$), formyl, lower alkoxycarbonyl [e.g., —C(=O)OCH$_3$], phenyl or phenyl substituted with one or more halogens (e.g., Cl, F) or lower haloalkyl (e.g., —CF$_3$), phenoxy, or phenoxy substituted with one or more halogens (e.g., Cl, F), lower haloalkoxy, lower alkoxyalkyl, carboxy, cyano, nitro, aminocarbonyl, lower alkylcarbonylamino, lower alkylsulfonylamino;
or substituted phenyl of the formula

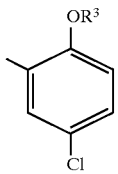

wherein R$^3$ is hydrogen; alkyl (e.g., methyl, 1-methylethyl, n-pentyl, or undecyl); tri(lower alkyl)silylalkyl; (4-halophenyl) lower alkyl; pentahalophenylalkyl; pyridin-2-ylalkyl; or 2-(4-alkylsulfonylphenoxy)alkyl;
(c) naphthyl;
(d) thienyl or thienyl substituted with halogen, lower alkyl, or haloalkyl;
(e) an alkenyl or alkynyl of the formulae:

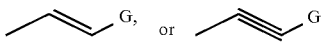

wherein G is hydrogen, trimethylsilyl or

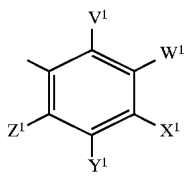

wherein V$^1$, W$^1$, X$^1$, Y$^1$, and Z$^1$ are independently selected from hydrogen, halogen, lower alkyl, lower haloalkyl, cyano, carboxy, lower alkoxycarbonyl and aminocarbonyl; and (f) aroyl or substituted aroyl of the formula:

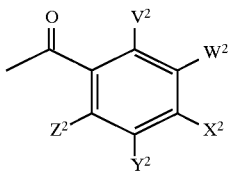

wherein $V^2$, $W^2$, $X^2$, $Y^2$, and $Z^2$ are independently selected from hydrogen, halogen, haloalkyl, cyano, carboxy, lower alkoxycarbonyl, and phenyl substituted with halogen or haloalkyl;

(g) substituted aryloxy [e.g., phenoxy] of the formula:

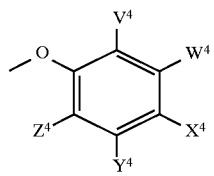

wherein $V^4$, $W^4$, $X^4$, $Y^4$, and $Z^4$ are selected from hydrogen, halogen (e.g., Cl), or haloalkyl (e.g., —CF$_3$)

(h) a benzo-fused oxygen-containing heterocycle of the formula:

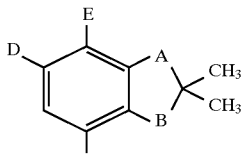

wherein A and B are independently selected from oxygen, methylene, or carbonyl; with the proviso that at least one of A or B is oxygen; and wherein D is hydrogen, halogen (e.g., Cl, F), lower alkyl (e.g., —CH$_3$), or lower haloalkyl (e.g., —CF$_3$); and E is hydrogen, hydroxy, or lower alkoxy (e.g., —OCH$_3$);

Y is hydrogen or fluorine;

Z is hydrogen;

with the proviso that when X is iodo, W is other than hydrogen; when X is bromo, W is other than hydrogen or methyl; and with the further proviso that when X is substituted phenyl or aryloxy, W is other than hydrogen.

Also included amongst these compounds are those having the following structure:

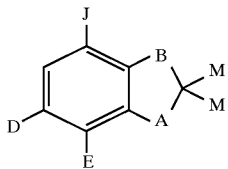

(I-B)

wherein A and B are independently selected from oxygen, methylene, or carbonyl; with the proviso that at least one of A or B is oxygen;

D is halogen (e.g., Cl, F), lower alkyl (e.g., —CH$_3$), or lower haloalkyl (e.g., —CF$_3$);

E is hydrogen, methoxy, hydroxy, amino, nitro, cyano, or aminocarbonyl;

J is hydrogen, halogen (e.g., Br, I), —B(OH)$_2$, or trialkylstannyl (e.g., trimethylstannyl); and, M is lower alkyl (e.g., methyl).

These novel intermediates may readily be prepared from known starting materials by conventional means. Illustrations of these intermediates of structure I-A, and their preparation, include 2-amino-5-iodo-6-methylbenzonitrile, 2-amino-5-(trimethylsilylethynyl)-6-methyl-benzonitrile, 2-amino-5-ethynyl-6-methylbenzonitrile, 2-amino-6-methyl-5-[(4-trifluoromethylphenyl)ethynyl]benzonitrile (see Example 17); 2-amino-5-bromo-6-(1-methylethyl)benzonitrile, 2-amino-6-(1-methylethyl)-5-[3,5-di(trifluoromethyl)phenyl]benzonitrile (see Example 26); 2-amino-6-methyl-5-[3,5-di(trifluoromethyl)phenyl]benzonitrile (see Example 1); 2-amino-6-methyl-5-(5-chlorothien-2-yl)benzonitrile (see Example 18); 2-amino-5-(4-trifluomethylphenylcarbonyl)-6-methylbenzonitrile (see Example 19); 2-amino-6-methyl-5-(6-chloro-2,3-dihydro-2,2-dimethylbenzofuran-4-yl)benzonitrile (see Example 23); and 2-amino-4-fluoro-6-methyl-5-[3,5-di(trifluoromethyl)phenyl]benzonitrile (see Example 24); as well as those of Examples 6, 16, 20–22, and 30–33.

Illustrations of these intermediates of structure 1-B, and their preparation, include 6-chloro-7-cyano-2,3-dihydro-2, 2-dimethylbenzofuran, 7-aminocarbonyl-6-chloro-2,3-dihydro-2,2-dimethylbenzofuran, 7-amino-6-chloro-2,3-dihydro-2,2-dimethylbenzofuran, 7-amino-4-bromo-6-chloro-2,3-dihydro-2,2-dimethylbenzofuran, 4-bromo-6-chloro-2,3-dihydro-2,2-dimethylbenzofuran, 6-chloro-2,3-dihydro-2,2-dimethylbenzofuran-4-ylboronic acid (see Example 23); 2,3-dihydro-2,2,6-trimethyl-7-nitrobenzofuran, 7-amino-2,3-dihydro-2,2,6-trimethylbenzofuran, 7-amino-4-bromo-2,3-dihydro-2,2,6-trimethylbenzofuran, and 2,3-dihydro-2,2,6-trimethylbenzofuran-4-ylboronic acid (see Example 30); as well as those of Examples 27, 31, and 33.

Conversion of these intermediates to the insecticides of this invention also employs methods well-known to those skilled in the art, and in any event these methods are fully documented by the processes of the above examples.

In each of these methods the nature of the substituents on the final product may readily be determined by selection of the correspondingly substituted starting materials as shown in the examples above, or by introduction of such groups by means well known to those skilled in the art such as conventional halogenation, reduction reactions or the like.

We claim:

1. A compound having the formula

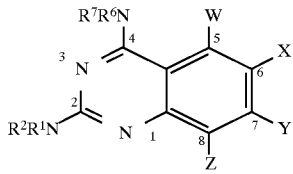

wherein $R^1$ is hydrogen, or lower alkyl;

$R^6$ is hydrogen;

$R^2$ and $R^7$ are independently hydrogen, lower alkyl, alkylcarbonyl, lower alkoxycarbonyl, lower haloalkylcarbonyl, alkoxyalkylcarbonyl, alkoxyalkoxyalkylcarbonyl, or alkoxyalkoxyalkoxyalkylcarbonyl;

or $R^1$ and $R^2$, taken together, form the group —$R^5$—O—$R^5$, wherein $R^5$ is lower alkylene;

W is selected from hydrogen, halogen, lower alkyl, lower haloalkyl, phenyl, and phenyl substituted with lower alkyl or lower haloalkyl, with the proviso that when X is phenyl, W is other than hydrogen;

Y and Z are selected from hydrogen, halogen, and phenyl; and

X is selected from (a) phenyl;

(b) substituted aryl, wherein the substituents are selected from one or more of halogens, lower alkyl, lower haloalkyl, lower alkoxy, lower alkylthio, lower alkylsulfonyl, formyl, lower alkoxycarbonyl, phenyl or phenyl substituted with one or more halogens or lower haloalkyl, phenoxy, or phenoxy substituted with one or more halogens, lower haloalkoxy, lower alkoxyalkyl, carboxy, cyano, nitro, aminocarbonyl, lower alkylcarbonylamino, lower alkylsulfonylamino;

or substituted phenyl of the formula

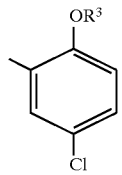

wherein $R^3$ is hydrogen; alkyl; tri(lower alkyl) silylalkyl; (4-halophenyl)lower alkyl; pentahalophenylalkyl; pyridin-2-ylalkyl; or 2-(4-alkylsulfonylphenoxy)ethyl;

(c) naphthyl;

(d) thienyl or thienyl substituted with halogen, lower alkyl, or haloalkyl;

(e) aroyl or substituted aroyl of the formula:

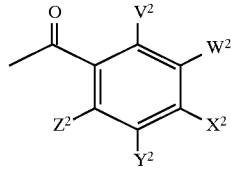

wherein $V^2$, $W^2$, $X^2$, $Y^2$, and $Z^2$ are independently selected from hydrogen, halogen, haloalkyl, cyano, carboxy, lower alkoxycarbonyl, and phenyl substituted with halogen or haloalkyl;

(f) (aryl)(halo)alkenyl of the formula:

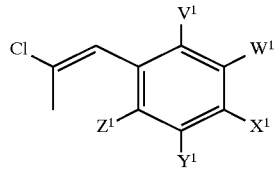

wherein $V^1$, $W^1$, $X^1$, $Y^1$, and $Z^1$ are independently selected from hydrogen, halogen, lower alkyl, lower haloalkyl, cyano, carboxy, lower alkoxycarbonyl, and aminocarbonyl; and (g) a benzo-fused oxygen-containing heterocycle of the formula:

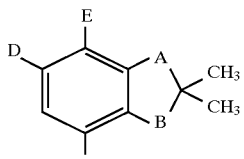

wherein A and B are independently selected from oxygen, methylene, and carbonyl; with the proviso that at least one of A or B is oxygen; D is hydrogen, halogen, lower alkyl, or lower haloalkyl; and E is hydrogen, hydroxy, or lower alkoxy; to form the corresponding heterocycle 2,3-dihydro-2,2-dimethylbenzofuran-4-yl, 2,3-dihydro-2,2-dimethylbenzofuran-7-yl, 6-halo-2,3-dihydro-2,2-dimethylbenzofuran-4-yl, 5-halo-2,3-dihydro-2,2-dimethylbenzofuran-7-yl, or 2,3-dihydro-2,2-dimethyl-3-benzofuranon-4-yl.

2. The compound of claim 1 wherein $R^1$, $R^2$, $R^6$, $R^7$, Y and Z are hydrogen; W is methyl; and X is (i) phenyl substituted with one or more of fluoro, chloro, or trifluoromethyl;

(ii) compounds of the formula

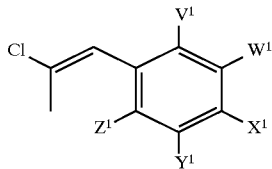

wherein $V^1$, $W^1$, $X^1$, $Y^1$, and $Z^1$ are independently selected from hydrogen, chloro, and trifluoromethyl; or (iii) a benzo-fused oxygen containing heterocycle of the formula:

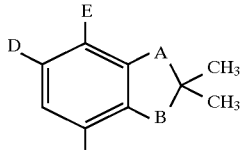

wherein A and B are independently selected from oxygen, methylene, and carbonyl; with the proviso that at least one of A or B is oxygen; D is hydrogen, halogen, lower alkyl, or lower haloalkyl; and E is hydrogen, hydroxy, or lower alkoxy; to form the corresponding heterocycle 2,3-dihydro-2,2-dimethylbenzofuran-4-yl, 2,3-dihydro-2,2-dimethylbenzofuran-7-yl, 6-halo-2,3-dihydro-2,2-dimethylbenzofuran-4-yl, 5-halo-2,3-dihydro-2,2-dimethylbenzofuran-7-yl, or 2,3-dihydro-2,2-dimethyl-3-benzofuranon-4-yl.

* * * * *

UNITED STATES PATENT AND TRADEMARK OFFICE
CERTIFICATE OF CORRECTION

PATENT NO. : 5,874,579

DATED : February 23, 1999

INVENTOR(S) : Robert N. Henrie II, et al.

It is certified that error appears in the above-identified patent and that said Letters Patent is hereby corrected as shown below:

```
On title page:
```
Item [54], the title should read --INSECTICIDAL SUBSTITUTED-2, 4-DIAMINOQUINAZOLINES--. (And column 1, lines 1-3 )

Signed and Sealed this

Sixth Day of April, 1999

*Attest:*

Q. TODD DICKINSON

*Attesting Officer*      Acting Commissioner of Patents and Trademarks